US012060578B2

(12) United States Patent
Wolf et al.

(10) Patent No.: US 12,060,578 B2
(45) Date of Patent: *Aug. 13, 2024

(54) SYSTEMS AND METHODS FOR ASSOCIATING COMPOUNDS WITH PHYSIOLOGICAL CONDITIONS USING FINGERPRINT ANALYSIS

(71) Applicant: Flagship Pioneering Innovations VI, LLC, Cambridge, MA (US)

(72) Inventors: Fabian Alexander Wolf, Munich (DE); Ragy Haddad, Cambridge, MA (US); Nicholas McCartney Plugis, Cambridge, MA (US)

(73) Assignee: FLAGSHIP PIONEERING INNOVATIONS VI, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,543

(22) Filed: Jun. 15, 2022

(65) Prior Publication Data
US 2022/0403335 A1 Dec. 22, 2022

Related U.S. Application Data

(60) Provisional application No. 63/210,930, filed on Jun. 15, 2021.

(51) Int. Cl.
*C12N 5/0789* (2010.01)
*A61K 35/12* (2015.01)
*A61K 35/28* (2015.01)
*G16C 20/30* (2019.01)
*G16C 20/70* (2019.01)

(52) U.S. Cl.
CPC ............ *C12N 5/0647* (2013.01); *A61K 35/28* (2013.01); *G16C 20/30* (2019.02); *G16C 20/70* (2019.02); *A61K 2035/124* (2013.01); *C12N 2501/125* (2013.01)

(58) Field of Classification Search
None
See application file for complete search history.

(56) References Cited

U.S. PATENT DOCUMENTS

2020/0020419 A1   1/2020   Kahvejian et al.

OTHER PUBLICATIONS

Lamb et al The Connectivity Map: Using Gene-Expression Signatures to Connect Small Molecules, Genes, and Disease. Science, vol. 313, No. 5795, 2006, pp. 1929-1935. (2006).*
U.S. Appl. No. 16/511,691 entitled "Methods of Analyzing Cells," filed Jul. 15, 2019.
Agresti, An Introduction to Categorical Data Analysis, 1996, Chapter 5, pp. 103-144, John Wiley & Son, New York.
Benjamini, Y., et al., Nucleic Acids Research 40(10):e72 (2012).
Borgelt and Meinl, 2006, "Full Perfect Extension Pruning for Frequent Graph Mining," Proc. Workshop on Mining Complex Data (MCD 2006 at ICDM 2006, Hong Kong, China, IEEE Press, Piscataway, NJ, USA.
Boser et al., 1992, "A training algorithm for optimal margin models," in Proceedings of the 5th Annual ACM Workshop on Computational Learning Theory, ACM Press, Pittsburgh, Pa., pp. 142-152.
Cristianini and Shawe-Taylor, 2000, "An Introduction to Support Vector Machines," Cambridge University Press, Cambridge.
Duan, 2016, "L1000CDS2: An ultra-fast Lincs L1000 Characteristic Direction Signature Search Engine," Systems Biology and Applications 2, article 16015.
Duda et al., 2001, Pattern Classification, Second Edition, John Wiley & Sons, Inc., New York.
Duvenaud et al., 2015, "Convolutional networks on graphs for learning molecular fingerprints," NeurIPS, 2224-2232.
Fernandes et al., 2017, "Transfer Learning with Partial Observability Applied to Cervical Cancer Screening," Pattern Recognition and Image Analysis: 8th Iberian Conference Proceedings, 243-250.
Franco, 2014, "The Use of 2D fingerprint methods to support the assessment of structural similarity in orphan drug legislation," J. Cheminform 6(5).
Gilmer et al., 2017, "Neural Message Passing for Quantum Chemistry," arXiv:1704.01212v2.
Hastie et al., 2001, The Elements of Statistical Learning, Springer-Verlag, New York,.
Honda et al., 2019, "SMILES Transformer: Pre-trained Molecular Fingerprint for Low Data Drug Discovery," arXiv:1911.04738.

(Continued)

*Primary Examiner* — Joseph Woitach

(57) ABSTRACT

Systems and methods for associating a compound with physiological conditions are provided. A fingerprint of a compound chemical structure is obtained and inputted to a model that outputs one or more calculated activation scores. Each activation score represents a cellular constituent module in a set of modules, where each module includes a subset of cellular constituents and a first module in the set of modules is associated with the physiological condition. When the activation score for the first module satisfies a threshold criterion, the compound is identified as associated with the physiological condition. In some aspects, each activation score represents a perturbation signature associated with the physiological condition and the compound is identified when the activation score for a first perturbation signature satisfies a threshold criterion. Systems and methods for training a model that associates compounds with physiological conditions are also provided.

30 Claims, 26 Drawing Sheets

(56) References Cited

OTHER PUBLICATIONS

Huang et al., 2016, "Modelling the Tox21 10 K chemical profiles for in vivo toxicity prediction and mechanism characterization," Nat Commun. 7, p. 10425.

Lipinski, 1997, Adv. Drug Del. Rev. 23, 3.

Meinl and Worlein, 2006 "Mining Molecular Datasets on Symmetric Processor Systems," International conference on Systems, man and Cybernetics 2, pp. 1269-1274.

Raymond and Willett, 2002, "Effectiveness of graph-based and fingerprint-based similarity measures for virtual screening of 2D chemical structure databases," Journal of Computer-Aided Molecular Design 16, 59-71.

Rensi and Altman, 2017, "Flexible Analog Search with Kernel PCA Embedded Molecule Vectors," Computational and Structural Biotechnology Journal, doi:10.1016/j.csbj.2017.03.003.

Rumelhart et al., 1988, "Neurocomputing: Foundations of research," ch. Learning Representations by Back-propagating Errors, pp. 696-699, Cambridge, MA, USA: Mit Press.

Schwartz et al., PLoS One 6(1):e16685 (2011).

Sumithra et al., 2015, "A Review of Various Linear and Non Linear Dimensionality Reduction Techniques," Int J Comp Sci and Inf Tech, 6(3), 2354-2360.

Vapnik, 1998, Statistical Learning Theory, Wiley, New York; Mount, 2001, Bioinformatics: sequence and genome analysis, Cold Spring Harbor Laboratory Press, Cold Spring Harbor, N.Y.

Wang et al., 2004, "Adaptive Manifold Learning," Advances in Neural Information Processing Systems 17.

Zeiler, 2012 "ADADELTA: an adaptive learning rate method," CoRR, vol. abs/1212.5701.

Duran-Frigola, M. et al., "Extending the small-molecule similarity principle to all levels of biology with the Chemical Checker", Nature Biotechnology, v. 38, No. 9, p. 1087-1096 (May 18, 2020).

Jo, J. et al., "The Message passing neural networks for chemical property prediction on SMILES", Methods, v. 179, p. 65-72, (May 21, 2020).

Lotfollahi, M. "Learning interpretable cellular responses to complex perturbations in high-throughput screens", BioRxiv, (Apr. 15, 2021), XP055962485.

* cited by examiner

| 200 A method of associating a plurality of cellular constituents with a physiological condition of interest. |
|---|

↓ 202

| Obtain one or more first datasets comprising or collectively comprising, for each respective cell in a first plurality of cells, for each respective cellular constituent in a plurality of cellular constituents, a corresponding abundance of the respective cellular constituent in the respective cell. The first plurality of cells comprises twenty or more cells and collectively represents a plurality of annotated cell states. The plurality of cellular constituents comprises 10 or more cellular constituents. |
|---|

↓ 204

| Access or form a plurality of vectors. Each respective vector in the plurality of vectors (i) corresponds to a respective cellular constituent in the plurality of constituents and (ii) comprises a corresponding plurality of elements. Each respective element in the corresponding plurality of elements has a corresponding count representing the corresponding abundance of the respective cellular constituent in a respective cell in the first plurality of cells. |
|---|

↓ 206

| Use the plurality of vectors to identify each cellular constituent module 132 in a plurality of cellular constituent modules. Each cellular constituent module in the plurality of cellular constituent modules includes a subset of the plurality of cellular constituents 134. The plurality of cellular constituent modules are arranged in a latent representation dimensioned by (i) the cellular constituent modules and (ii) the plurality of cellular constituents or a representation thereof. The plurality of cellular constituent modules comprises more than ten cellular constituent modules. |
|---|

↓ 208

| Obtain one or more second datasets comprising or collectively comprising, for each respective cell in a second plurality of cells, for each respective cellular constituent in the plurality of cellular constituents, a corresponding abundance of the respective cellular constituent in the respective cell, thereby obtaining a cellular constituent count data structure dimensioned by (i) the second plurality of cells and (ii) the plurality of cellular constituents or the representation thereof. The second plurality of cells comprises twenty or more cells and collectively represents a plurality of covariates informative of the physiological condition of interest. |
|---|

Figure 2A

Count Matrix 402

| | Cell 1 | Cell 2 | Cell 3 | Cell 4 | ... | Cell N |
|---|---|---|---|---|---|---|
| Cellular constituent 1 | Count$_{1-1}$ | Count$_{1-2}$ | Count$_{1-3}$ | Count$_{1-4}$ | ... | Count$_{1-N}$ |
| Cellular constituent 2 | Count$_{2-1}$ | Count$_{2-2}$ | Count$_{2-3}$ | Count$_{2-4}$ | ... | Count$_{2-N}$ |
| ... | ... | ... | ... | ... | ... | ... |
| Cellular constituent Z | Count$_{Z-1}$ | Count$_{Z-2}$ | Count$_{Z-3}$ | Count$_{Z-4}$ | ... | Count$_{Z-N}$ |

Cellular constituents →

Latent Representation 404 (using correlation model)

Weights are binary (e.g., a weight of "1" means cellular constituent is in a cellular constituent module, a weight of "0" means a cellular constituent is not in a cellular constituent module)

| | CC1 | CC2 | CC3 | CC4 | ... | CCZ |
|---|---|---|---|---|---|---|
| Cellular c. module 1 | Weight$_{1-1}$ | Weight$_{1-2}$ | Weight$_{1-3}$ | Weight$_{1-4}$ | ... | Weight$_{1-Z}$ |
| Cellular c. module 2 | Weight$_{2-1}$ | Weight$_{2-2}$ | Weight$_{2-3}$ | Weight$_{2-4}$ | ... | Weight$_{2-Z}$ |
| ... | ... | ... | ... | ... | ... | ... |
| Cellular c. module K | Weight$_{K-1}$ | Weight$_{K-2}$ | Weight$_{K-3}$ | Weight$_{K-4}$ | ... | Weight$_{K-Z}$ |

132-1, 132-K

Cellular constituents →
Cellular constituent modules ↓

Figure 4

Activation Data Structure 504

| Cellular c. modules | Cell 1 | ... | Cell G |
|---|---|---|---|
| Cellular c. module 1 | $Act_{1\text{-}1}$ | ... | $Act_{1\text{-}G}$ |
| Cellular c. module 2 | $Act_{2\text{-}1}$ | ... | $Act_{2\text{-}G}$ |
| Cellular c. module 3 | $Act_{3\text{-}1}$ | ... | $Act_{3\text{-}G}$ |
| ⋮ | ⋮ | ⋮ | ⋮ |
| Cellular c. module K | $Act_{K\text{-}1}$ | ... | $Act_{K\text{-}G}$ |

640

601

604-1

| CC modules | Cpd 1 | ... | Cpd W |
|---|---|---|---|
| CC module 1 | $Weight_{1\text{-}1}$ | ... | $Weight_{1\text{-}W}$ |
| CC module 2 | $Weight_{2\text{-}1}$ | ... | $Weight_{2\text{-}W}$ |
| ⋮ | ⋮ | ⋮ | ⋮ |
| CC module K | $Weight_{K\text{-}1}$ | ... | $Weight_{K\text{-}W}$ |

Cellular constituent model

604-K

602

| Cpd | Predicted | Actual |
|---|---|---|
| Cpd 1 | $Pred.\ Value_1$ | $Act.\ Value_2$ |
| Cpd 2 | $Pred.\ Value_2$ | $Act.\ Value_2$ |
| ⋮ | ⋮ | ⋮ |
| Cpd W | $Pred.\ Value_W$ | $Act.\ Value_W$ |

Figure 6

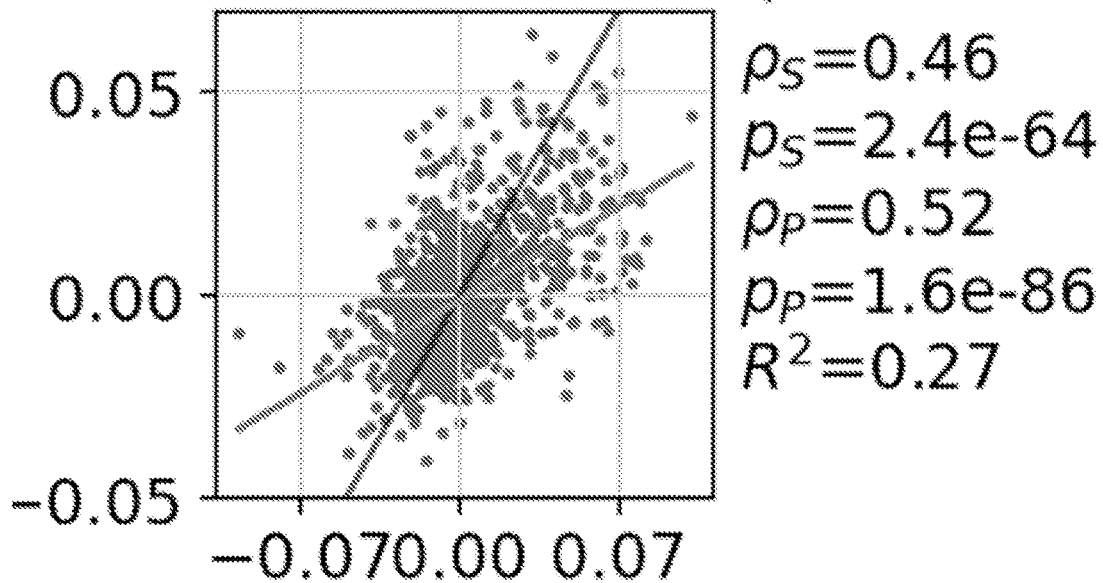
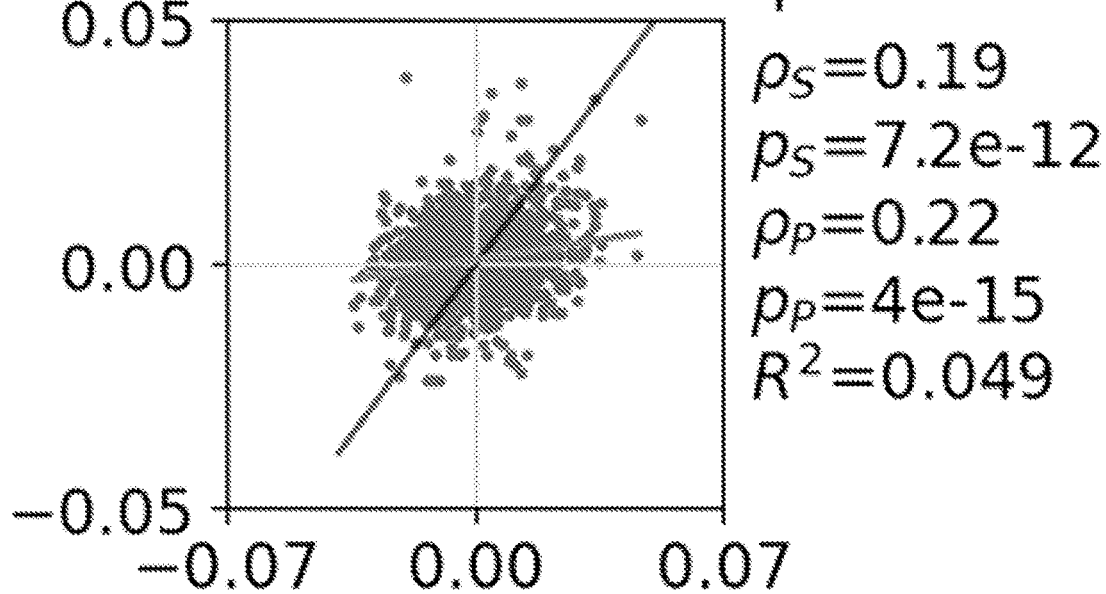
Figure 10C

SYSTEMS AND METHODS FOR ASSOCIATING COMPOUNDS WITH PHYSIOLOGICAL CONDITIONS USING FINGERPRINT ANALYSIS

CROSS REFERENCE TO RELATED APPLICATIONS

This application claims priority to U.S. Provisional Patent Application Nos. 63/210,736, entitled "SYSTEMS AND METHODS FOR ASSOCIATING COMPOUNDS WITH PROPERTIES USING CLIQUE ANALYSIS OF CELL-BASED DATA," filed Jun. 15, 2021; which is hereby incorporated by reference in its entirety.

TECHNICAL FIELD

The present invention relates generally to systems and methods for associating compounds with physiological conditions.

BACKGROUND

The study of cellular mechanisms is important for understanding disease.

Biological tissues are dynamic and highly networked multicellular systems. Dysfunction in subcellular networks in specific cells shift the entire landscape of cell behaviors and leads to disease states. Existing drug discovery efforts seek to characterize the molecular mechanisms that cause cells to transition from healthy to disease states, and to identify pharmacological approaches to reverse or inhibit these transitions. Past efforts have also sought to identify molecular signatures characterizing these transitions, and to identify pharmacological approaches that reverse these signatures.

Molecular data on bulk collections of cells, in tissues or cells enriched by surface markers, mask the phenotypic and molecular diversity of individual cells in a population. The heterogeneity of cells in these bulk collections of cells causes the results of current efforts aimed at elucidating disease-driving mechanisms to be misleading or even wholly incorrect. New approaches, such as single-cell RNA sequencing, can characterize individual cells at the molecular level. These data provide a substrate for understanding varied cell states at higher resolution and reveal the rich and remarkable diversity of states that cells possess.

Significant challenges exist when interpreting single cell data, namely the sparsity of these data, overlooking the presence of molecules present in cells, and noise, with uncertainty in the accuracy of these molecular measurements. Accordingly, new approaches are required to derive insight into pharmacological approaches for controlling individual cell state, and to correspondingly resolve disease.

In addition, complex diseases often cannot be broken down to a single or a few molecular targets. In spite of recent advances in high-throughput imaging technology and high-throughput screening for in vitro disease models, translating candidate targets generated from in vitro-based screening approaches into efficacious drugs is a considerable task that often involves a return to the comparatively slow and inefficient molecular target-based drug discovery approach.

Given the above background, what is needed in the art are systems and methods for identification of candidate compounds for drug discovery.

SUMMARY

The present disclosure addresses the above-identified shortcomings. The present disclosure addresses these shortcomings, at least in part, with cellular constituent data (e.g., abundances of genes and/or perturbation signatures) corresponding to physiological conditions of interest (e.g., phenotypes, diseases, cell states, and/or cellular processes of interest), and using latent representations and machine learning to determine associations (e.g., weights and/or correlations) between modules (e.g., subsets) of cellular constituents and the physiological condition of interest. In particular, the present disclosure provides systems and methods for elucidating molecular mechanisms underlying various physiological conditions, such as disease.

An aspect of the present disclosure provides a method of associating a test chemical compound with a physiological condition of interest. The method comprises (A) obtaining a fingerprint of a chemical structure of the test chemical compound.

The method further comprises (B) accessing a set of cellular constituent modules. Each respective cellular constituent module in the set of cellular constituent modules includes a respective independent subset of a plurality of cellular constituents. A corresponding plurality of cell-based assay abundance values for each respective independent subset of the plurality of cellular constituents separately correlate across a plurality of different states associated with the physiological condition. A first cellular constituent module in the set of cellular constituent modules is associated with the physiological condition of interest.

The method further comprises (C) responsive to inputting the fingerprint of the chemical structure into a model retrieving, as output from the model, a respective activation score for each cellular constituent module in the set of cellular constituent modules. In some embodiments, the model comprises 50 or more parameters, 100 or more parameters, 1000 or more parameters, or 10,000 or more parameters.

The method further comprises (D) associating the test chemical compound with the physiological condition of interest when the activation score for the first cellular constituent module satisfies a first threshold criterion.

In some embodiments, the cell-based assay abundance values are of cells of an organ. In some such embodiments, the organ is heart, liver, lung, muscle, brain, pancreas, spleen, kidney, small intestine, uterus, or bladder.

In some embodiments, the cell-based assay abundance values are of cells of a tissue. In some embodiments, the tissue is bone, cartilage, joint, tracheae, spinal cord, cornea, eye, skin, or blood vessel.

In some embodiments, the cell-based assay abundance values are of cells of a plurality of stem cells. In some embodiments, the plurality of stem cells is a plurality of embryonic stem cells, a plurality of adult stem cells, or a plurality of induced pluripotent stem cells (iPSC).

In some embodiments, the cell-based assay abundance values are of cells of a plurality of primary human cells. In some such embodiments, the plurality of primary human cells are a plurality of CD34+ cells, a plurality of CD34+ hematopoietic stems, a plurality of progenitor cells (HSPC), a plurality of T-cells, a plurality of mesenchymal stem cells (MSC), a plurality of airway basal stem cells, or a plurality of induced pluripotent stem cells.

In some embodiments, the cell-based assay abundance values are of cells in umbilical cord blood, in peripheral blood, or in bone marrow.

In some embodiments, the cell-based assay abundance values are of cells in a solid tissue. In some such embodiments, the solid tissue is placenta, liver, heart, brain, kidney, or gastrointestinal tract.

In some embodiments, the cell-based assay abundance values are of a plurality of differentiated cells. In some such embodiments the plurality of differentiated cells is a plurality of megakaryocytes, a plurality of osteoblasts, a plurality of chondrocytes, a plurality of adipocytes, a plurality of hepatocytes, a plurality of hepatic mesothelial cells, a plurality of biliary epithelial cells, a plurality of hepatic stellate cells, a plurality of hepatic sinusoid endothelial cells, a plurality of Kupffer cells, a plurality of pit cells, a plurality of vascular endothelial cells, a plurality of pancreatic duct epithelial cells, a plurality of pancreatic duct cells, a plurality of centroacinous cells, a plurality of acinar cells, a plurality of islets of Langerhans, a plurality of cardiac muscle cells, a plurality of fibroblasts, a plurality of keratinocytes, a plurality of smooth muscle cells, a plurality of type I alveolar epithelial cells, a plurality of type II alveolar epithelial cells, a plurality of Clara cells, a plurality of ciliated epithelial cells, a plurality of basal cells, a plurality of goblet cells, a plurality of neuroendocrine cells, a plurality of kultschitzky cells, a plurality of renal tubular epithelial cells, a plurality of urothelial cells, a plurality of columnar epithelial cells, a plurality of glomerular epithelial cells, a plurality of glomerular endothelial cells, a plurality of podocytes, a plurality of mesangium cells, a plurality of nerve cells, a plurality of astrocytes, a plurality of microglia, or a plurality of oligodendrocytes.

In some embodiments, the corresponding plurality of cell-based assay abundance values is single-cell ribonucleic acid (RNA) sequencing (scRNA-seq) data of a plurality of cells. In some such embodiments, the plurality of different states associated with the physiological condition is derived by exposing different aliquots of cells to one or more reference compounds known to affect the physiological condition in addition to a control state in which an aliquot of cells is not free of exposure to a compound known to affect the physiological condition.

In some embodiments, the corresponding plurality of cell-based assay abundance values is from bulk RNA sequences.

In some embodiments, the corresponding plurality of cell-based assay abundance values is from single cell RNA sequencing.

In some embodiments, the set of cellular constituent modules consists of the first cellular constituent module.

In some embodiments, the set of cellular constituent modules comprises a plurality of cellular constituent modules and the model is an ensemble model comprising a plurality of component models. Each component model in the plurality of component models provides an activation score for a different cellular constituent module in the set of cellular constituent modules responsive to inputting the fingerprint of the chemical structure into each component model in the plurality of component models.

In some embodiments, the method further comprises calculating the fingerprint from a simplified molecular-input line-entry system (SMILES) string representation of the test chemical compound.

In some such embodiments, each component model in the plurality of component models is a corresponding neural network (e.g., a fully connected neural network, a message passing neural network, or a combination thereof). In some embodiments, the corresponding neural network is a combination of a corresponding fully connected neural network and a corresponding message passing neural network, a first output of the corresponding fully connected neural network and a second output of the corresponding message passing neural network is combined, responsive to inputting the fingerprint of the chemical structure into the corresponding fully connected neural network and the corresponding message passing neural network, to determine an activation score in the one or more calculated activation scores for the corresponding cellular constituent module in the set of cellular constituent modules.

In some such embodiments a component model in the plurality of component models is a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the set of cellular constituent modules is a plurality of cellular constituent modules, a first subset of the plurality of cellular constituent modules, including the first cellular constituent module, is associated with the physiological condition of interest, a second subset of the plurality of cellular constituent modules is not associated with the physiological condition of interest, and the test chemical compound is identified with the physiological condition of interest when the respective calculated activation score for the first cellular constituent module satisfies the first threshold criterion and the respective calculated activation score for a cellular constituent module in the second subset of the plurality of cellular constituent modules satisfies a second threshold criterion, other than the first threshold criterion.

In some embodiments, the method further comprise identifying the first cellular constituent module by a process comprising: obtaining one or more first datasets in electronic form, the one or more first datasets comprising or collectively comprising: for each respective cell in a first plurality of cells, wherein the first plurality of cells comprises twenty or more cells and collectively represents a plurality of annotated cell states: for each respective cellular constituent in the plurality of cellular constituents (e.g., at least 10, 20, 30, 100, or 1000 or more cellular constituents: a corresponding abundance of the respective cellular constituent in the respective cell, thereby accessing or forming a plurality of vectors, each respective vector in the plurality of vectors (i) corresponding to a respective cellular constituent in the plurality of constituents and (ii) comprising a corresponding plurality of elements, each respective element in the corresponding plurality of elements having a corresponding count representing the corresponding abundance of the respective cellular constituent in the respective cell in the first plurality of cells. The method further comprises using the plurality of vectors to identify each candidate cellular constituent module in a plurality of candidate cellular constituent modules, each candidate cellular constituent module in the plurality of candidate cellular constituent modules including a subset of the plurality of cellular constituents, where the plurality of cellular constituent modules are arranged in a latent representation dimensioned by (i) the plurality of candidate cellular constituent modules and (ii) the plurality of cellular constituents or a representation thereof, and wherein the plurality of cellular constituent modules comprises more than ten cellular constituent modules. The method further comprise obtaining one or more second datasets in electronic form, the one or more second datasets comprising or collectively comprises for each respective cell in a second plurality of cells, wherein the second plurality of cells comprises twenty or more cells and collectively represents a plurality of covariates informative of the physiological condition of interest: for each respective cellular constituent in the plurality of cellular constituents: a corresponding abundance of the respective cellular constituent in the respective cell, thereby obtaining a cellular constituent count data structure dimensioned by (i) the second plurality of cells and (ii) the plurality of cellular constituents or the representation thereof. The method further comprises forming an activation data structure by combining the cellular constituent count data structure and the latent representation using the plurality of cellular constituents or the representation thereof as a common dimension, wherein the activation data structure comprises, for each cellular constituent module in the plurality of cellular constituent modules: for each cell in the second plurality of cells, a respective activation weight; and training a candidate cellular constituent model using, for each respective covariate in the plurality of covariates, a difference between (i) a calculated activation against each cellular constituent module represented by the candidate cellular constituent model upon input of a fingerprint of the covariate into the candidate cellular constituent model and (ii) actual activation against each cellular constituent module represented by the candidate cellular constituent model, wherein the training adjusts a plurality of covariate parameters associated with the candidate cellular constituent model responsive to the difference. In some such embodiments, the plurality of covariate parameters comprises: for each respective cellular constituent module in the plurality of cellular constituent modules: for each respective covariate: a corresponding parameter indicating whether the respective covariate correlates, across the second plurality of cells, with the respective cellular constituent module; and the method further comprises: identifying, using the plurality of covariate parameters upon training the candidate cellular constituent model, the first cellular constituent module in the plurality of candidate cellular constituent modules. In some such embodiments the method further comprises an annotated cell state in the plurality of annotated cell states is an exposure (e.g., a duration of exposure, a concentration of the compound, or a combination of a duration of exposure and a concentration of the compound) of a cell in the first plurality of cells to a compound under an exposure condition.

In some embodiments, each cellular constituent in the plurality of cellular constituents is a particular gene, a particular mRNA associated with a gene, a carbohydrate, a lipid, an epigenetic feature, a metabolite, a protein, or a combination thereof.

In some embodiments each cellular constituent in the plurality of cellular constituents is a particular gene, a particular mRNA associated with a gene, a carbohydrate, a lipid, an epigenetic feature, a metabolite, a protein, or a combination thereof, and the corresponding abundance of the respective cellular constituent in the respective cell in the first or second plurality of cells is determined by a colorimetric measurement, a fluorescence measurement, a luminescence measurement, or a resonance energy transfer (FRET) measurement.

In some embodiments each cellular constituent in the plurality of cellular constituents is a particular gene, a particular mRNA associated with a gene, a carbohydrate, a lipid, an epigenetic feature, a metabolite, a protein, or a combination thereof, and the corresponding abundance of the respective cellular constituent in the respective cell in the first or second plurality of cells is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Ab-seq, miRNA-seq, CITE-seq, or any combination thereof.

In some embodiments the using the plurality of vectors to identify each candidate cellular constituent module in the plurality of candidate cellular constituent modules comprises application of a correlation model to the plurality of vectors using each corresponding plurality of elements of each vector in the plurality of vectors. In some such embodiments, the correlation model includes a graph clustering (e.g., Leiden clustering on a Pearson-correlation-based distance metric, Louvain clustering, etc.).

In some embodiments, the plurality of cellular constituent modules consists of between 10 and 2000 cellular constituent modules, or between 100 and 8,000 cellular constituents. In some embodiments, each candidate cellular constituent module in the plurality of constituent modules consists of between two and three hundred cellular constituents.

In some embodiments, the physiological condition of interest is a disease.

In some embodiments the physiological condition of interest is a disease, and the first plurality of cells includes cells that are representative of the disease and cells that are not representative of the disease as indicated by the plurality of annotated cell states.

In some embodiments, the plurality of covariates comprises cell batch, cell donor, cell type, disease status, exposure to a chemical compound, or any combination thereof.

In some embodiments, the training the candidate cellular constituent model is performed using a categorical cross-entropy loss in a multi-task formulation, in which each covariate in the plurality of covariates corresponds to a cost function in plurality of cost functions and each respective cost function in the plurality of cost functions has a common weighting factor.

In some embodiments the test chemical compound is an organic compound having a molecular weight of less than 2000 Daltons. In some such embodiments, the test chemical compound is an organic compound that satisfies each of the Lipinski rule of five criteria. In some embodiments, the test chemical compound is an organic compound that satisfies at least three criteria of the Lipinski rule of five criteria. In some embodiments, the model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the method further comprises generating the fingerprint from a chemical structure of the test chemical compound using Daylight, BCI, ECFP4, EcFC, MDL, APFP, TTFP, UNITY 2D fingerprint, RNNS2S, or GraphConv.

In some embodiments, the set of cellular constituent modules comprises five or more cellular constituent modules, ten or more cellular constituent modules, or 100 or more cellular constituent modules.

In some embodiments, the independent subset of the plurality of cellular constituents in the respective cellular constituent module comprises five or more cellular constituents.

In some embodiments the independent subset of the plurality of cellular constituents in the respective cellular constituent module consists of between two and 20 cellular constituents in a molecular pathway associated with the physiological condition of interest.

In some embodiments, first threshold criterion is a requirement that the first cellular constituent module have a threshold activation score.

Another aspect of the present disclosure provides a method of associating a test chemical compound with a physiological condition of interest.

The method comprises (A) obtaining a fingerprint of a chemical structure of the test chemical compound.

The method further comprises (B) accessing a set of perturbation signatures, where each respective perturbation signature in the set of perturbation signature includes a respective independent subset of a plurality of cellular constituents, each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound.

The method further comprises (C) inputting the fingerprint into a model, where the model comprises 50, 100, 500, 1000, or 10,000 or more parameters, the model outputs one or more calculated activation scores responsive to the inputting of the fingerprint into the model, each respective calculated activation score in the one or more calculated activation scores represents a corresponding perturbation signature in the set of perturbation signatures.

The method further comprises (D) associating the chemical compound with the physiological condition of interest when the respective calculated activation score for a first perturbation signature in the set of perturbation signatures satisfies a first threshold criterion.

In some embodiments, the method further comprising calculating the fingerprint from a simplified molecular-input line-entry system (SMILES) string representation of the test chemical compound.

In some embodiments the model comprises a neural network. In some such embodiments, the neural network is a fully connected neural network, a message passing neural network, or a combination thereof.

In some embodiments the model is an ensemble model comprising a plurality of component models, and each component model in the plurality of component models provides an activation score for a different perturbation signature in the set of perturbation signatures responsive to inputting the fingerprint of the chemical structure into each component model in the set of plurality of component models.

In some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, each component model in the plurality of component models is a corresponding neural network (e.g., the corresponding neural network is a fully connected neural network, a message passing neural network, or a combination thereof).

In some embodiments, a component model in the plurality of component models is a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the corresponding neural network is a combination of a fully connected neural network and a message passing neural network, and a first output of the first neural network and a second output of the second neural network is combined, responsive to inputting the fingerprint of the chemical structure into the fully connected neural network and the message passing neural network, to determine an activation score in the one or more calculated activation scores for a first perturbation signature in the set of perturbation signatures.

In some embodiments, the set of perturbation signatures is a plurality of perturbation signatures, a first subset of the plurality of perturbation signatures, including the first perturbation signature, is associated with the physiological condition of interest, a second subset of the plurality of perturbation signatures is not associated with the physiological condition of interest, and the test chemical compound is identified with the physiological condition of interest when the respective calculated activation score for the first perturbation signature satisfies the first threshold criterion and the respective calculated activation score for a perturbation signature in the second subset of the plurality of perturbation signatures satisfies a second threshold criterion, other than the first threshold criterion.

In some embodiments, the physiological condition of interest is a disease.

In some embodiments, the test chemical compound is an organic compound having a molecular weight of less than 2000 Daltons.

In some embodiments, the test chemical compound is an organic compound that satisfies each of the Lipinski rule of five criteria. In some such embodiments, the test chemical compound is an organic compound that satisfies at least three criteria of the Lipinski rule of five criteria.

In some embodiments, the model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments the method further comprises generating the fingerprint from a chemical structure of the test chemical compound using using Daylight, BCI, ECFP4, EcFC, MDL, APFP, TTFP, UNITY 2D fingerprint, RNNS2S, or GraphConv.

In some embodiments, the set of perturbation signatures consists of the first perturbation signature.

In some embodiments, the set of perturbation signature comprises five or more perturbation signatures, ten or more perturbation signatures or 100 or more perturbation signatures.

In some embodiments, the first threshold criterion is a requirement that the first perturbation signature have a threshold activation score.

Another aspect of the present disclosure provides a method of associating chemical compounds with a physiological condition of interest.

The method comprises at a computer system comprising a memory and one or more processors: (A) obtaining, in electronic form, a respective fingerprint of a corresponding chemical structure of each respective compound in a plurality of compounds, thereby obtaining a plurality of fingerprints.

The method further comprises (B) obtaining, in electronic form, a respective numerical activation score of each cellular constituent module in a set of cellular constituent modules for each compound in the plurality of compounds, where each respective cellular constituent module in the set of cellular constituent modules includes an independent subset of a plurality of cellular constituents.

The method further comprises (C) training an untrained model using for each respective chemical structure of each respective compound in the plurality of compounds, for each respective cellular constituent module in the set of cellular constituent modules, a respective difference between: (i) a respective calculated activation score for the respective cellular constituent module upon input of the fingerprint of the chemical structure of the respective compound into the untrained model and (ii) the respective numerical activation score of the respective cellular constituent module for the respective compound in the set of cellular constituent modules, where the training (C) adjusts a plurality of parameters associated with the untrained model responsive to the difference, and where the plurality of parameters comprises 50, 100, 200, 500, 1000, or 10,000 or more parameters, thereby obtaining a trained model that associates chemical compounds with the physiological condition of interest.

In some embodiments, the set of cellular constituent modules consists of a single cellular constituent module.

In some embodiments, set of cellular constituent modules comprises a plurality of cellular constituent modules.

In some embodiments, the set of cellular constituent modules consists of between two and five hundred cellular constituent modules.

In some embodiments, the plurality of compounds consists of between 10 and $1 \times 10^6$ compounds.

In some embodiments, the plurality of compounds consists of between 100 and 100,000 compounds.

In some embodiments, the plurality of compounds consists of between 1000 and 100,000 compounds.

In some embodiments, the training (C) adjusts the plurality of parameters associated with the untrained model responsive to each difference associated with each respective compound for each respective cellular constituent module in the set of cellular constituent modules in accordance with a regression algorithm. In some such embodiments, the regression algorithm optimizes a least square error of each difference associated with each respective compound for each respective cellular constituent module in the set of cellular constituent modules.

In some embodiments, the trained model comprises a neural network (e.g., a fully connected neural network, a message passing neural network, or a combination thereof).

In some embodiments, the trained model is an ensemble model of a plurality of component models and each respective component model in the plurality of component models outputs a calculated activation score for a different cellular constituent module in the plurality of cellular constituent modules. In some such embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, each component model in the plurality of component models is a corresponding neural network. In some such embodiments, the corresponding neural network is a fully connected neural network, a message passing neural network, or a combination thereof.

In some embodiments, the set of cellular constituent modules is a plurality of cellular constituent modules, a first subset of the plurality of cellular constituent modules is associated with the physiological condition of interest, and a second subset of the plurality of cellular constituent modules is not associated with the physiological condition of interest.

In some embodiments, the method further comprises identifying a cellular constituent module in the plurality of cellular constituent modules by a process comprising: obtaining one or more first datasets in electronic form, the one or more first datasets comprising or collectively comprising: for each respective cell in a first plurality of cells, wherein the first plurality of cells comprises twenty or more cells and collectively represents a plurality of annotated cell states: for each respective cellular constituent in the plurality of cellular constituents, where the plurality of cellular constituents comprises 5, 10, 15, 20, 25, 50, or 100 or more cellular constituents: a corresponding abundance of the respective cellular constituent in the respective cell, thereby accessing or forming a plurality of vectors. Each respective vector in the plurality of vectors (i) corresponds to a respective cellular constituent in the plurality of constituents and (ii) comprises a corresponding plurality of elements. Each respective element in the corresponding plurality of elements has a corresponding count representing the corresponding abundance of the respective cellular constituent in the respective cell in the first plurality of cells. The plurality of vectors are used to identify each candidate cellular constituent module in a plurality of candidate cellular constituent modules, each candidate cellular constituent module in the plurality of candidate cellular constituent modules including a subset of the plurality of cellular constituents. The plurality of cellular constituent modules are arranged in a latent representation dimensioned by (i) the plurality of candidate cellular constituent modules and (ii) the plurality of cellular constituents or a representation thereof, and the plurality of cellular constituent modules comprises more than 3, 5, 10, 15, 20, or 100 cellular constituent modules. One or more second datasets are obtained in electronic form, the one or more second datasets comprising or collectively comprising: for each respective cell in a second plurality of cells, where the second plurality of cells comprises twenty or more cells and collectively represents a plurality of covariates informative of the physiological condition of interest: for each respective cellular constituent in the plurality of cellular constituents: a corresponding abundance of the respective cellular constituent in the respective cell, thereby obtaining cellular constituent count data structure dimensioned by (i) the second plurality of cells and (ii) the plurality of cellular constituents or the representation thereof. An activation data structure is formed by combining the cellular constituent count data structure and the latent representation using the plurality of cellular constituents or the representation thereof as a common dimension, where the activation data structure comprises, for each cellular constituent module in the plurality of cellular constituent modules: for each cell in the second plurality of cells, a respective activation weight. A candidate cellular constituent model is trained using a difference between (i) a prediction of an absence or presence of each covariate in the plurality of covariates in each cellular constituent module represented in the activation data structure upon input of the activation data structure into the candidate model and (ii) actual absence or presence of each covariate in each cellular constituent module. This training adjusts a plurality of covariate parameters associated with the candidate cellular constituent model responsive to the difference.

In some embodiments, the plurality of covariate parameters comprises: for each respective cellular constituent module in the plurality of cellular constituent modules: for each respective covariate: a corresponding parameter indicating whether the respective covariate correlates, across the second plurality of cells, with the respective cellular constituent module, and there is identified, using the plurality of covariate parameters upon training the candidate cellular constituent model, the cellular constituent module in the plurality of candidate cellular constituent modules.

In some embodiments, an annotated cell state in the plurality of annotated cell states is an exposure of a cell in the first plurality of cells to a compound under an exposure condition.

In some embodiments, the exposure condition is a duration of exposure, a concentration of the compound, or a combination of a duration of exposure and a concentration of the compound.

In some embodiments, each cellular constituent in the plurality of cellular constituents is a particular gene, a particular mRNA associated with a gene, a carbohydrate, a lipid, an epigenetic feature, a metabolite, a protein, or a combination thereof.

In some embodiments, the corresponding abundance of the respective cellular constituent in the respective cell in the first or second plurality of cells is determined by a colorimetric measurement, a fluorescence measurement, a luminescence measurement, or a resonance energy transfer (FRET) measurement.

In some embodiments, the corresponding abundance of the respective cellular constituent in the respective cell in the first or second plurality of cells is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Ab-seq, miRNA-seq, CITE-seq, or any combination thereof.

In some embodiments, the using the plurality of vectors to identify each candidate cellular constituent module in the plurality of candidate cellular constituent modules comprises application of a correlation model to the plurality of vectors using each corresponding plurality of elements of each vector in the plurality of vectors. In some such embodiments, the correlation model includes graph clustering (e.g., Leiden clustering on a Pearson-correlation-based distance metric or is Louvain clustering).

In some embodiments, the plurality of cellular constituents consists of between 100 and 8,000 cellular constituents.

In some embodiments, each candidate cellular constituent module in the plurality of constituent modules consists of between two and three hundred cellular constituents.

In some embodiments, the physiological condition of interest is a disease.

In some embodiments, the physiological condition is a disease, and the first plurality of cells includes cells that are representative of the disease and cells that are not representative of the disease as indicated by the plurality of annotated cell states.

In some embodiments, the plurality of covariates comprises cell batch, cell donor, cell type, disease status, or exposure to a chemical compound.

In some embodiments, the training the candidate cellular constituent model is performed using a categorical cross-entropy loss in a multi-task formulation, in which each covariate in the plurality of covariates corresponds to a cost function in plurality of cost functions and each respective cost function in the plurality of cost functions has a common weighting factor.

In some embodiments, each chemical compound in the plurality of chemical compounds is an organic compound having a molecular weight of less than 2000 Daltons.

In some embodiments, each chemical compound in the plurality of chemical compounds satisfies each of the Lipinski rule of five criteria. In some such embodiments, each chemical compound in the plurality of chemical compounds satisfies at least three criteria of the Lipinski rule of five criteria.

In some embodiments, the trained model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the method further comprising generating each respective fingerprint from the corresponding chemical structure using Daylight, BCI, ECFP4, EcFC, MDL, APFP, TTFP, UNITY 2D fingerprint, RNNS2S, or GraphConv.

In some embodiments, the set of cellular constituent modules comprises five or more cellular constituent modules, ten or more cellular constituent modules, or 100 or more cellular constituent modules.

Another aspect of the present disclosure provides a method of associating chemical compounds with a physiological condition of interest. The method for example can be performed at a computer system comprising a memory and one or more processors.

The method comprises (A) obtaining, in electronic form, a respective fingerprint of a corresponding chemical structure of each respective compound in a plurality of compounds, thereby obtaining a plurality of fingerprints.

The method further comprises (B) obtaining, in electronic form, a respective numerical activation score of each respective perturbation signature in a set of perturbation signatures for each corresponding compound in the plurality of compounds, where each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state. One of the respective first cell state and second cell state is an unperturbed cell state and the other of the respective first cell state and the second cell state is a respective perturbed cell state caused by exposure of cells to the corresponding compound.

The method further comprises (C) training an untrained model using for each respective chemical structure of each respective compound in the plurality of compounds, for each respective perturbation signature in the set of perturbation signature, a respective difference between: (i) a respective calculated activation score for the respective perturbation signature upon input of the fingerprint of the chemical structure of the respective compound into the untrained model and (ii) the respective numerical activation score of the respective perturbation signature for the corresponding compound in the set of perturbation signatures. The training (C) adjusts a plurality of parameters associated with the untrained model responsive to the difference thereby obtaining a trained model that associates chemical compounds with the physiological condition of interest. In some embodiments, the plurality of parameters comprises 50, 100, 200, 500, 1000, 10,000, or $1 \times 10^6$ or more parameters.

In some embodiments, the set of perturbation signatures consists of a single perturbation signature.

In some embodiments, the set of perturbation signatures consists of between two and five hundred perturbation signatures.

In some embodiments, the plurality of compounds consists of between 10 and $1 \times 10^6$ compounds. In some embodiments, the plurality of compounds consists of between 100 and 100,000 compounds. In some embodiments, the plurality of compounds consists of between 1000 and 100,000 compounds.

In some embodiments, the training (C) adjusts the plurality of parameters associated with the untrained model responsive to each difference associated with each corresponding compound for each respective perturbation signature in the set of perturbation signatures in accordance with a regression algorithm. In some such embodiments, the regression algorithm optimizes a least square error of each difference associated with each corresponding compound for each respective perturbation signature in the set of perturbation signatures.

In some embodiments, the trained model comprises a neural network (e.g., a fully connected neural network, a message passing neural network, or a combination thereof).

In some embodiments, the trained model is an ensemble model of a plurality of component models and each respective component model in the plurality of component models outputs a calculated activation score for a different set of perturbation signature in the plurality of set of perturbation signatures responsive to inputting a fingerprint of a respective chemical structure into each component model in the set of plurality of component models. In some such embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, each component model in the plurality of component models is a corresponding neural network (e.g., a fully connected neural network, a message passing neural network, or a combination thereof).

In some embodiments, the set of perturbation signatures comprises a plurality of perturbation signature, a first subset of the plurality of perturbation signatures is associated with the physiological condition of interest, and a second subset of the plurality of perturbation signatures is not associated with the physiological condition of interest.

In some embodiments, the physiological condition of interest is a disease.

In some embodiments, each chemical compound in the plurality of chemical compounds is an organic compound having a molecular weight of less than 2000 Daltons.

In some embodiments, each chemical compound in the plurality of chemical compounds satisfies each of the Lipinski rule of five criteria.

In some embodiments, each chemical compound in the plurality of chemical compounds satisfies at least three criteria of the Lipinski rule of five criteria.

In some embodiments, the trained model comprises a logistic regression model, a neural network model, a support vector machine, a Naive Bayes model, a nearest neighbor model, a boosted trees model, a random forest model, a decision tree model, a multinomial logistic regression model, a linear model, or a linear regression model.

In some embodiments, the method further comprising generating each respective fingerprint from the corresponding chemical structure using Daylight, BCI, ECFP4, EcFC, MDL, APFP, TTFP, UNITY 2D fingerprint, RNNS2S, or GraphConv.

In some embodiments, the set of perturbation signatures comprises five or more perturbation signatures, ten or more perturbation signatures, or 100 or more perturbation signatures.

In some embodiments, the method further comprises obtaining a respective numerical activation score of a respective perturbation signature in the set of perturbation signatures by a procedure comprising: accessing, in electronic form, a single-cell transition signature representing a measure of differential cellular constituent abundance between an unaltered cell state and an altered cell state, where the altered cell state occurs through the cellular transition from the unaltered cell state to the altered cell state, at least one of (i) the unaltered cell state, (ii) the altered cell state, and (iii) the transition from the unaltered cell state to the altered cell state is associated with the physiological condition of interest, and the single-cell transition signature comprises an identification of a reference plurality of cellular constituents and, for each respective cellular constituents in the plurality of reference cellular constituents, a corresponding first significance score that quantifies an association between a change in abundance of the respective cellular constituent and a change in cell state between the unaltered cell state and the altered cell state. Further, the single-cell transition signature and the respective perturbation signature are compared thereby determining the respective numerical activation score of the respective perturbation signature.

In some embodiments, the comparing the single-cell transition signature and the perturbation signature to determine the respective numerical activation score of the respective perturbation signature comprises comparing, for each respective cellular constituent in the reference plurality of cellular constituents of the single-cell transition signature: the first significance score of the respective cellular constituent to the corresponding significance score of the corresponding cellular constituent in the respective perturbation signature.

In some embodiments, the activation score of the respective perturbation signature is a relative ranking of a relevance of the respective perturbation signature, relative to other perturbation signatures in the set of perturbations signatures, to the single-cell transition signature.

In some embodiments, the relative ranking is determined by a Wilcoxon rank-sum test, a t-test, a logistic regression, or a generalized linear model.

In some embodiments, the unaltered cell state of the single-cell transition signature is the same as the first cell state or the second cell state of the respective perturbation signature.

In some embodiments, the unaltered cell state of the single-cell transition signature is different than both the first cell state and the second cell state of the respective perturbation signature.

In some embodiments, the method further comprises: pruning the reference plurality of cellular constituents of the single-cell transition signature and the respective plurality of cellular constituents of the respective perturbation signature to limit the comparing to transcription factors.

In some embodiments, the perturbed cell state of a respective perturbation signature in the plurality of perturbation signature is represented by control cells that have not been exposed to a compound in the plurality of compounds.

In some embodiments, the perturbed cell state of a respective perturbation signature in the plurality of perturbation signature is represented by an average across unrelated perturbed cells that have been exposed to chemical compounds in the plurality of chemical compounds other than the compound associated with the respective perturbation signature.

In some of the disclosed embodiments, the model is a regressor.

Another aspect of the present disclosure provides a computer system having one or more processors, and memory storing one or more programs for execution by the one or more processors, the one or more programs comprising instructions for performing any of the methods and/or embodiments disclosed herein.

Another aspect of the present disclosure provides a non-transitory computer readable storage medium storing one or more programs configured for execution by a computer, the one or more programs comprising instructions for carrying out any of the methods and/or embodiments disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIGS. 2A and 2B collectively provide a flow chart of processes and features of an example method for associating a plurality of cellular constituents with a physiological condition of interest, in accordance with various embodiments of the present disclosure.

FIG. 4 illustrates an example of a plurality of vectors of cellular constituents and an example of a latent representation of cellular constituent modules, in accordance with some embodiments of the present disclosure.

FIG. 6 illustrates an example of a method of training a model to adjust a plurality of compound weights, in accordance with some embodiments of the present disclosure.

FIGS. 10A, 10B, 10C, 10D, and 10E illustrate performance and 4-fold validation of an example method for predicting chemical structures for the activation of a fatty acid-related cellular program, in accordance with an embodiment of the present disclosure. FIG. 10A illustrates a schematic of a model architecture for predicting chemical structures. FIG. 10B illustrates performance on a test set of 1,200 randomly selected compounds. FIG. 10C illustrates performance on a test set of 1,200 compounds with different scaffolds than the training set. FIG. 10D illustrates validation for beigeing-related modules based on transcriptional activation in an in vitro preadipocyte assay. FIG. 10E illustrates optimization of predicted compounds drawn out of a database of 5 million compounds against a target module.

DETAILED DESCRIPTION

Introduction

Figure 1:
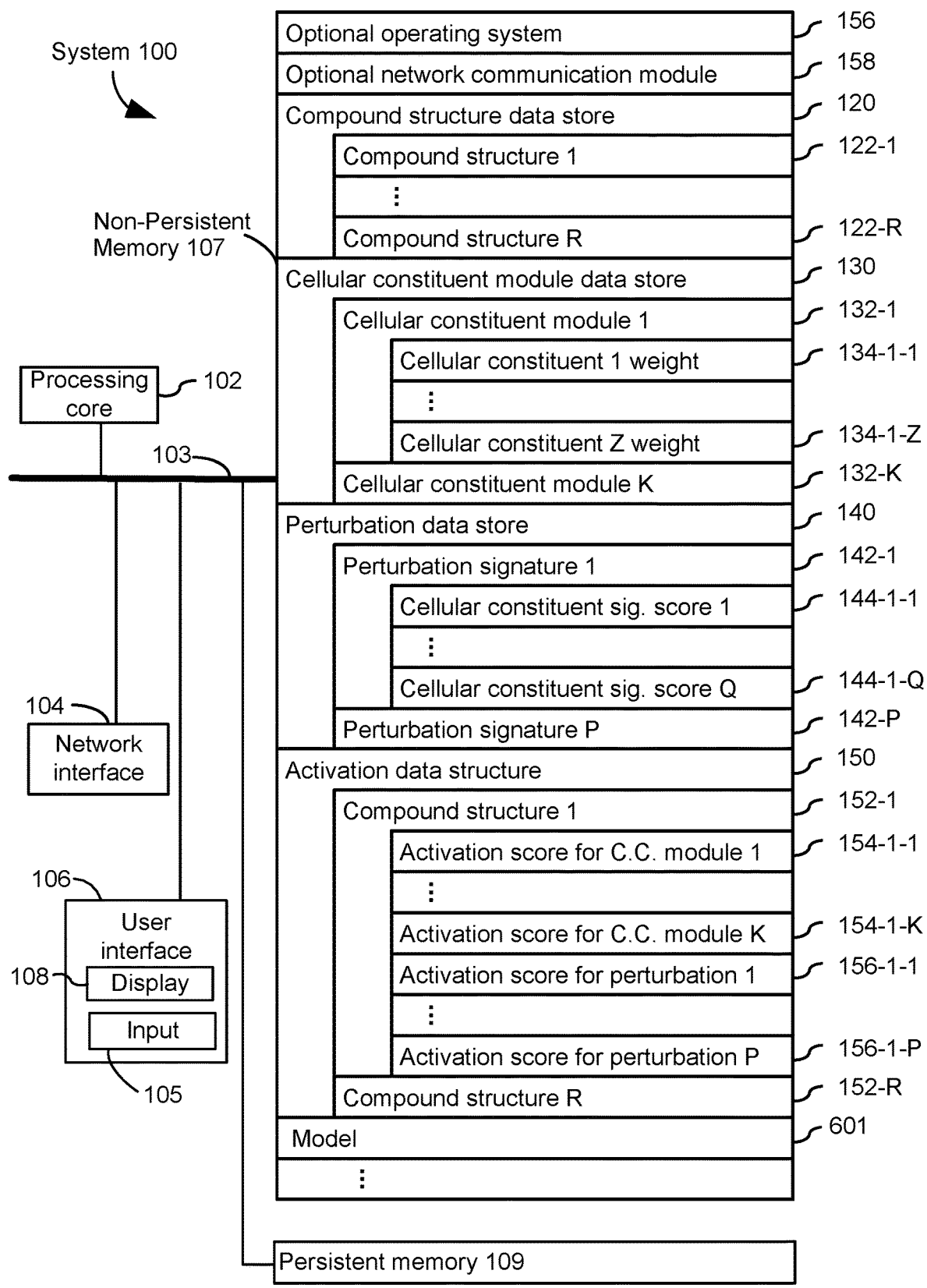
FIG. 1 illustrates a block diagram of an exemplary system and computing device, in accordance with an embodiment of the present disclosure.

Given the above background, the present disclosure describes an approach to drug discovery that targets cellular processes and programs that are critical to disease. This approach is realized, in some aspects, by predicting chemical structure-related modalities and their properties using computationally engineered representations of physiological conditions (e.g., cellular programs, cellular processes, and/or cell states) and the chemical structures of compounds. Encoded chemical structures can then be mapped onto the representations of cellular programs and/or cell states, thus associating compounds with physiological conditions.

For example, in some aspects, the present disclosure provides systems and methods for obtaining associations between molecular profiles (e.g., gene modules) and biological processes of interest (e.g., cellular programs and/or cell states) and chemical structures of compounds. These associations can be used to predict new chemical structures, such as those having similar functional or structural properties, for drug discovery.

In some embodiments, a computational modeling architecture with predictive capabilities is used to discover these associations, through the generation of latent representations of physiologically relevant chemical structures across one or more domains and/or data types. Associations can be derived, for example, from perturbational data that provides profiles of cellular behaviors, such as differential gene expression or cell state transitions in response to exposure of a cell to one or more compounds. In some implementations, the method combines and determines correlations between a variety of domains (e.g., molecular, cellular, clinical, in vivo, in vitro, knowledge-based, etc.) and/or a variety of data types (transcriptional, genetic, epigenetic, covariate, etc.) using latent representations and machine learning to predict physiologically relevant chemical structures.

In an example embodiment, the present disclosure provides a modeling approach using latent representations for compounds. For each respective compound in a plurality of compounds, the method includes generating a latent representation that stores a vector representing the likelihood that the respective compound induces each physiological condition in a plurality of physiological conditions. Physiological conditions can include cell state transitions and/or cellular constituent modules (e.g., gene modules) associated with a particular phenotype, cellular process, and/or disease. The method thus generates a matrix representation that serves as the multi-task training labels for the model, dimensioned by compounds and physiological conditions (e.g., cell states and/or gene modules), denoted, for instance, as n_compounds×n_cell_states or n_compounds×n_gene_modules.

The input for the machine learning model for associating compounds with physiological conditions includes the canonical isomeric SMILES representation and/or graph-based representations of each compound, which encodes the chemical structure of the compound, and is further used to train the model. Training labels are provided as numerical activation scores that associate each compound with each physiological condition. For instance, the vector for each compound can include a plurality of associated weights, where each weight indicates a likelihood that the compound induces a respective physiological condition, such as a respective cell state, cell state transition, perturbation signature, and/or activation of a respective gene module.

Upon receiving the matrix representation as input, the model is trained to learn cell state (e.g., perturbation signatures) and/or gene module activations from chemical structures by solving a regression problem. Two example model architectures are used to solve the regression problem. The first model utilizes a fully connected network on standard fingerprints of the SMILES strings, where the network architecture is a 3-layer network with ReLU activations. The second model includes an MPNN network out of the DGL library. Each of these models are trained independently from one another by optimizing a least square error of the regression prediction. Upon test time, the predictions of these models are averaged, thus forming an ensemble model including the first and the second models. The ensemble model can then be used to determine associations between compounds and physiological conditions, which can be further applied to obtain predictions of likely physiological activations from chemical structures and/or predictions of chemical structures likely to induce particular physiological conditions.

Advantageously, the systems and methods disclosed herein address the shortcomings described above by providing a systematic, scalable approach for drug discovery. For example, conventional machine learning approaches related to drug discovery utilize in silico target screening capabilities using 3D protein and chemical structure representation paired with deep learning methods and high-performance computing to compute a candidate compound's method of action towards a library of targets. These approaches, however, fall under the target-focused screening paradigm, which does not adequately address the complexity of dynamic and highly networked multicellular systems underlying biological processes. Other conventional methods for drug discovery use machine learning approaches to model how single cells and cell lines respond to perturbations, based on transcriptomic data or imaging data. In such methods, high-throughput datasets are used to learn phenotypic representations of disease and compound perturbations of cellular in vitro systems. These are used to predict compounds that would induce or counteract phenotypic disease responses. Traditional high-throughput data modeling approaches, however, are nevertheless disadvantaged by a lack of curation and a potential for the identification of large numbers of candidate targets. Validation of each potential candidate obtained from high-throughput screening is a laborious process, often requiring molecular target-based optimization or synthesis of hundreds or even thousands or compounds for in vitro screening.

In contrast to these approaches, the present disclosure advantageously provides systems and methods for obtaining representations chemical structure data (e.g., cellular responses to compound treatment), which are then mapped across representations of cell states, perturbation signatures and/or cellular constituents associated with biological processes (e.g., gene modules or perturbation signatures involved in physiological conditions of interest). This target-agnostic approach nevertheless allows for the systematic curation and optimization of candidate targets, thus bridging the considerable gap between target discovery to predictive translation across systems.

For example, as illustrated in the Examples below, a candidate pharmacophore involved in fatty acid metabolism was identified using an embodiment of the systems and methods disclosed herein. As further illustrated in Example 4, predictive translation based on the candidate pharmacophore generated 6 new chemical entities, all of which were found to activate a gene module involved in a fatty acid-related cellular process when tested on human adipocytes. Identification of the candidate pharmacophore and design of the 6 new chemical entities was performed without the need for high-throughput screening, identification or optimization against a protein target, or synthesis of hundreds or thousands of new compounds. Thus, the systems and methods provided herein improve the ease and efficiency of the drug discovery and development process over conventionally molecular target-based or phenotype-based approaches, from target discovery to predictive translation and validation.

Advantageously, the present disclosure further provides various systems and methods that improve the association of compounds with physiological conditions, by improving the training and use of a model for targeted determination of associations (e.g., weights and/or correlations) between compounds and physiological conditions. The complexity of a machine learning model includes time complexity (running time, or the measure of the speed of an algorithm for a given input size n), space complexity (space requirements, or the amount of computing power or memory needed to execute an algorithm for a given input size n), or both. Complexity (and subsequent computational burden) applies to both training of and prediction by a given model.

In some instances, computational complexity is impacted by implementation, incorporation of additional algorithms or cross-validation methods, and/or one or more parameters (e.g., weights and/or hyperparameters). In some instances, computational complexity is expressed as a function of input size n, where input data is the number of instances (e.g., the number of training samples), dimensions p (e.g., the number of features), the number of trees $nt_{rees}$ (e.g., for methods based on trees), the number of support vectors $n_{sv}$ (e.g., for methods based on support vectors), the number of neighbors k (e.g., for k nearest neighbor models), the number of classes c, and/or the number of neurons $n_i$ at a layer i (e.g., for neural networks). With respect to input size n, then, an approximation of computational complexity (e.g., in Big O notation) denotes how running time and/or space requirements increase as input size increases. Functions can increase in complexity at slower or faster rates relative to an increase in input size. Various approximations of computational complexity include but are not limited to constant (e.g., $O(1)$), logarithmic (e.g., $O(\log n)$), linear (e.g., $O(n)$), log linear (e.g., $O(n \log n)$), quadratic (e.g., $O(n^2)$), polynomial (e.g., $O(n^c)$), exponential (e.g., $O(c^n)$), and/or factorial (e.g., $O(n!)$). In some instances, simpler functions are accompanied by lower levels of computational complexity as input sizes increase, as in the case of constant functions, whereas more complex functions such as factorial functions can exhibit substantial increases in complexity in response to slight increases in input size.

Computational complexity of machine learning models can similarly be represented by functions (e.g., in Big O notation), and complexity may vary depending on the type of model, the size of one or more inputs or dimensions, usage (e.g., training and/or prediction), and/or whether time or space complexity is being assessed. For example, complexity in decision tree models is approximated as $O(n^2 p)$ for training and $O(p)$ for predictions, while complexity in linear regression models is approximated as $O(p^2 n + p^3)$ for training and $O(p)$ for predictions. For random forest models, training complexity is approximated as $O(n^2 p n_{trees})$ and prediction complexity is approximated as $O(p n_{trees})$. For gradient boosting models, complexity is approximated as $O(npn_{trees})$ for training and $O(pn_{trees})$ for predictions. For kernel support vector machines, complexity is approximated as $O(n^2 p + n^3)$ for training and $O(n_{sv} p)$ for predictions. For naïve Bayes models, complexity is represented as $O(np)$ for training and $O(p)$ for predictions, and for neural networks, complexity is approximated as $O(pn_1 + n_1 n_2 + \ldots)$ for predictions. Complexity in K nearest neighbors models is approximated as $O(knp)$ for time and $O(np)$ for space. For logistic regression models, complexity is approximated as $O(np)$ for time and $O(p)$ for space. For logistic regression models, complexity is approximated as $O(np)$ for time and $O(p)$ for space.

As described above, for machine learning models, computational complexity determines the scalability and therefore the overall effectiveness and usability of a model (e.g., a regressor) for increasing input, feature, and/or class sizes, as well as for variations in model architecture. In the context of large-scale datasets, as in the case of gene expression datasets comprising abundances of at least 10, at least 100, at least 1000 or more genes obtained for at least 10, at least 100, at least 1000 or more cells, the computational complexity of functions performed on such large datasets may strain the capabilities of many existing systems. In addition, as the number of input features (e.g., number of cellular constituents (e.g., genes) and/or number of compounds) and/or the number of instances (e.g., number of cells, cell state annotations, perturbation signatures, modules, and/or covariates) increases together with technological advancements, increasing availability of annotations, and expanding downstream applications and possibilities, the computational complexity of any given classification model can quickly overwhelm the time and space capacities provided by the specifications of a respective system.

Thus, by using a machine learning model with a minimum input size (e.g., at least 10, at least 100, at least 1000 or more compounds; at least 10, at least 50, at least 100 or more cellular constituents for a respective cellular constituent module; at least 5, at least 10, at least 100 or more perturbation signatures; and/or at least 5, at least 10, at least 100 or more cellular constituent modules) and/or a corresponding minimum number of parameters (e.g., at least 50, at least 100, or at least 1000 parameters and/or parameters corresponding to every possible pairing of all of the features input to the machine learning model) for the associating compounds with physiological conditions, the computational complexity is proportionally increased such that it cannot be mentally performed, and the method addresses a computational problem. For example, in an embodiment of the present disclosure, obtaining an activation score matrix dimensioned by a plurality of at least 10 cellular constituent modules and a plurality of at least 50 compounds comprises obtaining at least 500 parameters (e.g., weights). In another embodiment of the present disclosure, obtaining a respective activation weight for each compound in a plurality of at least 50 compounds, for each perturbation signature in a plurality of at least 10 perturbation signatures comprises obtaining at least 500 activation weights. Imposing similar minimums for additional input features and/or instances, including but not limited to number of cell state transitions, cellular constituents, cells, compounds, covariates, samples, time points, replicates, and/or batches, will similarly affect the computational complexity of the method.

Additional details on computational complexity in machine learning models are provided in "Computational complexity of machine learning algorithms," published Apr. 16, 2018, available online at: thekerneltrip.com/machine/learning/computational-complexity-learning-algorithms; Hastie, 2001, The Elements of Statistical Learning, Springer, New York; and Arora and Barak, 2009, Computational Complexity: A Modern Approach, Cambridge University Press, New York; each of which is hereby incorporated herein by reference in its entirety.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Plural instances may be provided for components, operations or structures described herein as a single instance. Finally, boundaries between various components, operations, and data stores are somewhat arbitrary, and particular operations are illustrated in the context of specific illustrative configurations. Other forms of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first dataset could be termed a second dataset, and, similarly, a second dataset could be termed a first dataset, without departing from the scope of the present invention. The first dataset and the second dataset are both datasets, but they are not the same dataset.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

Furthermore, when a reference number is given an "$i^{th}$" denotation, the reference number refers to a generic component, set, or embodiment. For instance, a cellular-component termed "cellular-component i" refers to the $i^{th}$ cellular-component in a plurality of cellular-components.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

Definitions

As used herein, the term "about" or "approximately" means within an acceptable error range for the particular value as determined by one of ordinary skill in the art, which depends in part on how the value is measured or determined, e.g., the limitations of the measurement system. For example, in some embodiments "about" means within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value can be assumed. All numerical values within the detailed description herein are modified by "about" the indicated value, and consider experimental error and variations that would be expected by a person having ordinary skill in the art. The term "about" can have the meaning as commonly understood by one of ordinary skill in the art. In some embodiments, the term "about" refers to ±10%. In some embodiments, the term "about" refers to ±5%.

As used herein, the terms "abundance," "abundance level," or "expression level" refers to an amount of a cellular constituent (e.g., a gene product such as an RNA species, e.g., mRNA or miRNA, or a protein molecule) present in one or more cells, or an average amount of a cellular constituent present across multiple cells. When referring to mRNA or protein expression, the term generally refers to the amount of any RNA or protein species corresponding to a particular genomic locus, e.g., a particular gene. However, in some embodiments, an abundance can refer to the amount of a particular isoform of an mRNA or protein corresponding to a particular gene that gives rise to multiple mRNA or protein isoforms. The genomic locus can be identified using a gene name, a chromosomal location, or any other genetic mapping metric.

As used interchangeably herein, a "cell state" or "biological state" refers to a state or phenotype of a cell or a population of cells. For example, a cell state can be healthy or diseased. A cell state can be one of a plurality of diseases. A cell state can be a response to a compound treatment and/or a differentiated cell lineage. A cell state can be characterized by a measure (e.g., an activation, expression, and/or measure of abundance) of one or more cellular constituents, including but not limited to one or more genes, one or more proteins, and/or one or more biological pathways.

As used herein, a "cell state transition" or "cellular transition" refers to a transition in a cell's state from a first cell state to a second cell state. In some embodiments, the second cell state is an altered cell state (e.g., a healthy cell state to a diseased cell state). In some embodiments, one of the respective first cell state and second cell state is an unperturbed state and the other of the respective first cell state and second cell state is a perturbed state caused by an exposure of the cell to a condition. The perturbed state can be caused by exposure of the cell to a compound. A cell state transition can be marked by a change in cellular constituent abundance in the cell, and thus by the identity and quantity of cellular constituents (e.g., mRNA, transcription factors) produced by the cell (e.g., a perturbation signature).

As used herein, the term "dataset" in reference to cellular constituent abundance measurements for a cell or a plurality of cells can refer to a high-dimensional set of data collected from a single cell (e.g., a single-cell cellular constituent abundance dataset) in some contexts. In other contexts, the term "dataset" can refer to a plurality of high-dimensional sets of data collected from single cells (e.g., a plurality of single-cell cellular constituent abundance datasets), each set of data of the plurality collected from one cell of a plurality of cells.

As used herein, the term "differential abundance" or "differential expression" refers to differences in the quantity and/or the frequency of a cellular constituent present in a first entity (e.g., a first cell, plurality of cells, and/or sample) as compared to a second entity (e.g., a second cell, plurality of cells, and/or sample). In some embodiments, a first entity is a sample characterized by a first cell state (e.g., a diseased phenotype) and a second entity is a sample characterized by a second cell state (e.g., a normal or healthy phenotype). For example, a cellular constituent can be a polynucleotide (e.g., an mRNA transcript) which is present at an elevated level or at a decreased level in entities characterized by a first cell state compared to entities characterized by a second cell state. In some embodiments, a cellular constituent can be a polynucleotide which is detected at a higher frequency or at a lower frequency in entities characterized by a first cell state compared to entities characterized by a second cell state. A cellular constituent can be differentially abundant in terms of quantity, frequency or both. In some instances, a cellular constituent is differentially abundant between two entities if the amount of the cellular constituent in one entity is statistically significantly different from the amount of the cellular constituent in the other entity. For example, a cellular constituent is differentially abundant in two entities if it is present at least about 120%, at least about 130%, at least about 150%, at least about 180%, at least about 200%, at least about 300%, at least about 500%, at least about 700%, at least about 900%, or at least about 1000% greater in one entity than it is present in the other entity, or if it is detectable in one entity and not detectable in the other. In some instances, a cellular constituent is differentially expressed in two sets of entities if the frequency of detecting the cellular constituent in a first subset of entities (e.g., cells representing a first subset of annotated cell states) is statistically significantly higher or lower than in a second subset of entities (e.g., cells representing a second subset of annotated cell states). For example, a cellular constituent is differentially expressed in two sets of entities if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of entities than the other set of entities.

As used herein, the term "healthy" refers to a sample characterized by a healthy state (e.g., obtained from a subject possessing good health). A healthy subject can demonstrate an absence of any malignant or non-malignant disease. A "healthy" individual can have other diseases or conditions, unrelated to the condition being assayed, which can normally not be considered "healthy."

As used herein, the term "perturbation" in reference to a cell (e.g., a perturbation of a cell or a cellular perturbation) refers to any exposure of the cell to one or more conditions, such as a treatment by one or more compounds. These compounds can be referred to as "perturbagens." In some embodiments, the perturbagen can include, e.g., a small molecule, a biologic, a therapeutic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other gene editing system), or any combination of any of the foregoing. A perturbation can induce or be characterized by a change in the phenotype of the cell and/or a change in the expression or abundance level of one or more cellular constituents in the cell (e.g., a perturbation signature). For instance, a perturbation can be characterized by a change in the transcriptional profile of the cell.

As used herein, the term "sample," "biological sample," or "patient sample," refers to any sample taken from a subject, which can reflect a biological state associated with the subject. Examples of samples include, but are not limited to, blood, whole blood, plasma, serum, urine, cerebrospinal fluid, fecal, saliva, sweat, tears, pleural fluid, pericardial fluid, or peritoneal fluid of the subject. A sample can include any tissue or material derived from a living or dead subject. A sample can be a cell-free sample. A sample can comprise one or more cellular constituents. For instance, a sample can comprise a nucleic acid (e.g., DNA or RNA) or a fragment thereof, or a protein. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A sample can be a bodily fluid. A sample can be a stool sample. A sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein the term "fingerprint" as in a fingerprint of a compound is a digital digest of the compound. Nonlimiting examples of such a digital digest include Daylight fingerprints, a BCI fingerprint, an ECFC4 fingerprint, an ECFP4 fingerprint, an EcFC fingerprint, an MDL fingerprint, an atom pair fingerprint (APFP fingerprint), a topological torsion fingerprint (TTFP) fingerprint, a UNITY 2D fingerprint, an RNNS2S fingerprint, or a GraphConv fingerprint. See Franco, 2014, "The Use of 2D fingerprint methods to support the assessment of structural similarity in orphan drug legislation," J. Cheminform 6, p. 5, and Rensi and Altman, 2017, "Flexible Analog Search with Kernel PCA Embedded Molecule Vectors," Computational and Structural Biotechnology Journal, doi:10.1016/j.csbj.2017.03.003, each of which is hereby incorporated by reference. See also Raymond and Willett, 2002, "Effectiveness of graph-based and fingerprint-based similarity measures for virtual screening of 2D chemical structure databases," Journal of Computer-Aided Molecular Design 16, 59-71, and Franco et al., 2014, "The use of 2D fingerprint methods to support the assessment of structural similarity in orphan drug legislation" Journal of chemoinformatics 6(5), each of which is hereby incorporated by reference.

As used herein the term "classification" can refer to any number(s) or other characters(s) that are associated with a particular property (e.g., a cellular process, a covariate, a cell state annotation, etc.) of an entity (e.g., a cell, a sample, a cellular constituent, a cellular constituent modules, etc.). For example, a "+" symbol (or the word "positive") can signify that an entity is classified as positive for a particular property (e.g., a cellular constituent module is positively associated with a cellular process of interest). In another example, the term "classification" can refer to a determination of correlation between an entity and a particular property (e.g., a correlation between a respective covariate and a respective cellular constituent module). In some embodiments, the classification is a correlation coefficient and/or a weight. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff value can refer to a value above which entities are excluded. A threshold value can be a value above or below which a particular classification applies. Either of these terms can be used in either of these contexts.

As used interchangeably herein, the term "classifier", "model", algorithm, "regressor", and/"or classifier" refers to a machine learning model or algorithm. In some embodiments, a model is an unsupervised learning algorithm. One example of an unsupervised learning algorithm is cluster analysis.

In some embodiments, a model is supervised machine learning. Nonlimiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level model). In some embodiments, a classifier or model of the present disclosure has 25 or more, 100 or more, 1000 or more 10,000 or more, 100,000 or more or $1 \times 10^6$ or more parameters and thus the calculations of the model cannot be mentally performed.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$, $n \geq 1 \times 10^6$, $n \geq 5 \times 10^6$, or $n \geq 1 \times 10^7$. As such, the algorithms, models, regressors, and/or classifiers of the present disclosure cannot be mentally performed. In some embodiments, n is between 10,000 and $1 \times 10^7$, between 100,000 and $5 \times 10^6$, or between 500,000 and $1 \times 10^6$. In some embodiments, the algorithms, models, regressors, and/or classifier of the present disclosure operate in a k-dimensional space, where k is a positive integer of 5 or greater (e.g., 5, 6, 7, 8, 9, 10, etc.). As such, the algorithms, models, regressors, and/or classifiers of the present disclosure cannot be mentally performed.

Neural networks. In some embodiments, the model is a neural network (e.g., a convolutional neural network and/or a residual neural network). Neural network models, also known as artificial neural networks (ANNs), include convolutional and/or residual neural network models (deep learning models). Neural networks can be machine learning models that may be trained to map an input data set to an output data set, where the neural network comprises an interconnected group of nodes organized into multiple layers of nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning model (DNN) can be a neural network comprising a plurality of hidden layers, e.g., two or more hidden layers. Each layer of the neural network can comprise a number of nodes (or "neurons"). A node can receive input that comes either directly from the input data or the output of nodes in previous layers, and perform a specific operation, e.g., a summation operation. In some embodiments, a connection from an input to a node is associated with a parameter (e.g., a weight and/or weighting factor). In some embodiments, the node may sum up the products of all pairs of inputs, xi, and their associated parameters. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in analyzing an image of a subject. Examples can include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. Convolutional and/or residual neural networks can be used for analyzing an image of a subject in accordance with the present disclosure.

For instance, a deep neural network model comprises an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference.

Neural network models, including convolutional neural network models, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, New York, each of which is hereby incorporated by reference in its entirety.

Support vector machines. In some embodiments, the model is a support vector machine (SVM). SVM models suitable for use as models are described in, for example, Cristianini and Shawe-Taylor, 2000, "An Introduction to Support Vector Machines," Cambridge University Press, Cambridge; Boser et al., 1992, "A training algorithm for optimal margin models," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes models. In some embodiments, the model is a Naive Bayes model. Naïve Bayes models suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference. A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference.

Nearest neighbor models. In some embodiments, a model is a nearest neighbor model. Nearest neighbor models can be memory-based and include no model to be fit. For nearest neighbors, given a query point xo (a test subject), the k training points $x_{(r)}$, r, . . . , k (here the training subjects) closest in distance to xo are identified and then the point xo is classified using the k nearest neighbors. Here, the distance to these neighbors is a function of the abundance values of the discriminating gene set. In some embodiments, Euclidean distance in feature space is used to determine distance as $d_{(i)}=\|x_{(i)}-x_{(O)}\|$. Typically, when the nearest neighbor model is used, the abundance data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference. In some embodiments, the number of distance calculations needed to solve the k-nearest neighbor model is such that a computer is used to solve the model for a given input because it cannot be mentally performed.

Random forest, decision tree, and boosted tree models. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific model that can be used is a classification and regression tree (CART). Other specific decision tree models include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses regression. The regression algorithm can be any type of regression. For example, in some embodiments, the regression is logistic regression. In some embodiments, the regression is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression is disclosed in Agresti, *An Introduction to Categorical Data Analysis*, 1996, Chapter 5, pp. 103-144, John Wiley & Son, New York, which is hereby incorporated by reference. In some embodiments, the model makes use of a regression model disclosed in Hastie et al., 2001, *The Elements of Statistical Learning*, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the model (linear model) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in the training set. If distance is a good measure of similarity, then the distance between reference entities in the same cluster can be significantly less than the distance between the reference entities in different clusters. However, clustering may not use of a distance metric. For example, a nonmetric similarity function $s(x, x')$ can be used to compare two vectors $x$ and $x'$. $s(x, x')$ can be a symmetric function whose value is large when $x$ and $x'$ are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering, and Jarvis-Patrick clustering. In some embodiments, the clustering comprises unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

As used herein, the term "untrained model" (e.g., "untrained regressor" and/or "untrained classifier") refers to a machine learning model such as a regressor or a classifier that has not been trained on a training dataset. As used herein, the term "training a model" refers to the process of training an untrained or partially trained model. For instance, in some embodiments, training a model comprises obtaining a plurality of cellular constituent modules arranged in a latent representation and a cellular constituent count data structure discussed below. The plurality of cellular constituent modules arranged in a latent representation and the cellular constituent count data structure are combined to form an activation data structure that is applied as collective input to an untrained or partially trained model, in conjunction with the actual absence of present of each covariate in a plurality of covariates for the plurality of cellular constituent modules in the activation data structure, (hereinafter "primary training dataset") to train the untrained or partially trained model on covariate-module correlation, thereby obtaining a trained model. Moreover, it will be appreciated that the term "untrained model" does not exclude the possibility that transfer learning techniques are used in such training of the untrained model. For instance, Fernandes et al., 2017, "Transfer Learning with Partial Observability Applied to Cervical Cancer Screening," Pattern Recognition and Image Analysis: $8^{th}$ Iberian Conference Proceedings, 243-250, which is hereby incorporated by reference, provides non-limiting examples of such transfer learning. In instances where transfer learning is used, the untrained model described above is provided with additional data over and beyond that of the primary training dataset. That is, in non-limiting examples of transfer learning embodiments, the untrained model receives (i) the primary training dataset and (ii) additional data. Typically, this additional data is in the form of coefficients (e.g., regression coefficients) that were learned from another, auxiliary training dataset. Moreover, while a description of a single auxiliary training dataset has been disclosed, it will be appreciated that there is no limit on the number of auxiliary training datasets that may be used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The coefficients learned from the first auxiliary training dataset (by application of a model such as regression to the first auxiliary training dataset) may be applied to the second auxiliary training dataset using transfer learning techniques (e.g., two-dimensional matrix multiplication), which in turn may result in a trained intermediate model whose coefficients are then applied to the primary training dataset and this, in conjunction with the primary training dataset itself, is applied to the untrained model. Alternatively, a first set of coefficients learned from the first auxiliary training dataset (by application of a model such as regression to the first auxiliary training dataset) and a second set of coefficients learned from the second auxiliary training dataset (by application of a model such as regression to the second auxiliary training dataset) may each individually be applied to a separate instance of the primary training dataset (e.g., by separate independent matrix multiplications) and both such applications of the coefficients to separate instances of the primary training dataset in conjunction with the primary training dataset itself (or some reduced form of the primary training dataset such as principal components or regression coefficients learned from the primary training set) may then be applied to the untrained model in order to train the untrained model. In either example, knowledge regarding covariate-module correlations (e.g., additional cell state annotations, additional covariates, and/or cellular constituent abundances thereof, etc.) derived from the first and second auxiliary training datasets is used, in conjunction with the covariate-labeled primary training dataset, to train the untrained model.

As used interchangeably herein, the term "neuron," "node," "unit," "hidden neuron," "hidden unit," or the like, refers to a unit of a neural network that accepts input and provides an output via an activation function and one or more parameters (e.g., coefficients and/or weights). For example, a hidden neuron can accept one or more inputs from a prior layer and provide an output that serves as an input for a subsequent layer. In some embodiments, a neural network comprises only one output neuron. In some embodiments, a neural network comprises a plurality of output neurons. Generally, the output is a prediction value, such as a probability or likelihood, a binary determination (e.g., a presence or absence, a positive or negative result), and/or a label (e.g., a classification and/or a correlation coefficient) of a condition of interest such as a covariate, a cell state annotation, or a cellular process of interest. For single-class classification models, the output can be a likelihood (e.g., a correlation coefficient and/or a weight) of an input feature (e.g., one or more cellular constituent modules) having a condition (e.g., a covariate, a cell state annotation, and/or a cellular process of interest). For multi-class classification models, multiple prediction values can be generated, with each prediction value indicating the likelihood of an input feature for each condition of interest.

As used herein, the term "parameter" refers to any coefficient or, similarly, any value of an internal or external element (e.g., weight and/or hyperparameter) in a model, classifier, or algorithm that can affect (e.g., modify, tailor, and/or adjust) one or more inputs, outputs, and/or functions in the model, classifier, or algorithm. In some embodiments, parameters are coefficients (e.g., weights) that modulate one or more inputs, outputs, or functions in a model. For instance, a value of a parameter can be used to upweight or down-weight the influence of an input (e.g., a feature) to a model. Features can be associated with parameters, such as in a logistic regression, SVM, or naïve Bayes model. A value of a parameter can, alternately or additionally, be used to upweight or down-weight the influence of a node in a neural network (e.g., where the node comprises one or more activation functions that define the transformation of an input to an output), a class, or an instance (e.g., of a cell in a plurality of cells). Assignment of parameters to specific inputs, outputs, functions, or features is not limited to any one paradigm for a given model but can be used in any suitable model architecture for optimal performance. In some instances, reference to the parameters (e.g., coefficients) associated with the inputs, outputs, functions, or features of a model can similarly be used as an indicator of the number, performance, or optimization of the same, such as in the context of the computational complexity of machine learning models. In some embodiments, a parameter has a fixed value. In some embodiments, a value of a parameter is manually and/or automatically adjustable (e.g., using a hyperparameter optimization method). In some embodiments, a value of a parameter is modified by a model validation and/or training process (e.g., by error minimization and/or backpropagation methods, as described elsewhere herein).

As used herein, the term "vector" is an enumerated list of elements, such as an array of elements, where each element has an assigned meaning. As such, the term "vector" as used in the present disclosure is interchangeable with the term "tensor." As an example, if a vector comprises the abundance counts, in a plurality of cells, for a respective cellular constituent, there exists a predetermined element in the vector for each one of the plurality of cells. For ease of presentation, in some instances a vector may be described as being one-dimensional. However, the present disclosure is not so limited. A vector of any dimension may be used in the present disclosure provided that a description of what each element in the vector represents is defined (e.g., that element 1 represents abundance count of cell 1 of a plurality of cells, etc.).

I. EXEMPLARY SYSTEM EMBODIMENTS

Now that an overview of some aspects of the present disclosure and some definitions used in the present disclosure have been provided, details of an exemplary system are described in conjunction with FIG. 1.

FIG. 1 provides a block diagram illustrating a system 100 in accordance with some embodiments of the present disclosure. The system 100 provides a determination of one or more cellular constituent modules in a plurality of cellular constituent modules that is associated with a cellular process of interest. In FIG. 1, the system 100 is illustrated as a computing device. Other topologies of the computer system 100 are possible. For instance, in some embodiments, the system 100 can in fact constitute several computer systems that are linked together in a network, or be a virtual machine or a container in a cloud computing environment. As such, the exemplary topology shown in FIG. 1 merely serves to describe the features of an embodiment of the present disclosure in a manner that will be readily understood to one of skill in the art.

Referring to FIG. 1, in some embodiments a computer system 100 (e.g., a computing device) includes a network interface 104. In some embodiments, the network interface 104 interconnects the system 100 computing devices within the system with each other, as well as optional external systems and devices, through one or more communication networks (e.g., through network communication module 158). In some embodiments, the network interface 104 optionally provides communication through network communication module 158 via the Internet, one or more local area networks (LANs), one or more wide area networks (WANs), other types of networks, or a combination of such networks.

Examples of networks include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

The system 100 in some embodiments includes one or more processing units (CPU(s)) 102 (e.g., a processor, a processing core, etc.), one or more network interfaces 104, a user interface 106 including (optionally) a display 108 and an input system 105 (e.g., an input/output interface, a keyboard, a mouse, etc.) for use by the user, memory (e.g., non-persistent memory 107, persistent memory 109), and one or more communication buses 103 for interconnecting the aforementioned components. The one or more communication buses 103 optionally include circuitry (sometimes called a chipset) that interconnects and controls communications between system components. The non-persistent memory 107 typically includes high-speed random access memory, such as DRAM, SRAM, DDR RAM, ROM, EEPROM, flash memory, whereas the persistent memory 109 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 109 optionally includes one or more storage devices remotely located from the CPU(s) 102. The persistent memory 109, and the non-volatile memory device(s) within the non-persistent memory 109, include non-transitory computer readable storage medium. In some embodiments, the non-persistent memory 107 or alternatively the non-transitory computer readable storage medium stores the following programs, modules and data structures, or a subset thereof, sometimes in conjunction with the persistent memory 109:

- an optional operating system 156 (e.g., ANDROID, iOS, DARWIN, RTXC, LINUX, UNIX, OS X, WINDOWS, or an embedded operating system such as VxWorks), which includes procedures for handling various basic system services and for performing hardware dependent tasks;
- an optional network communication module (or instructions) 158 for connecting the system 100 with other devices and/or a communication network 104;
- a compound structure data store 120 comprising a respective chemical structure 122 (e.g., 122-1, ... 122-R) or a representation thereof (e.g., a fingerprint of a chemical structure) for each compound in a plurality of compounds;
- a cellular constituent module data store 130 comprising a set of cellular constituent modules 132 (e.g., 132-1, ... 132-K), each respective cellular constituent module in the set of cellular constituent modules including a subset of a plurality of cellular constituents 134 (e.g., 134-1-1, ... 134-1-Z);
- a perturbation data store 140 comprising a set of perturbation signatures 142 (e.g., 142-1, ... 142-P), each respective perturbation signature in the set of perturbation signatures including an identification of a respective plurality of cellular constituents and, for each respective cellular constituent in the respective plurality of cellular constituents, a corresponding significance score 144 (e.g., 144-1-1, ... 144-1-Q) that quantifies an association between a change in abundance of the respective cellular constituent and a change in cell state between a respective first cell state and a respective second cell state;
- an activation data structure 150 comprising, for each respective chemical structure 152 (e.g., 152-1, ... 152-R) for each respective compound in the plurality of compounds:
  - optionally, for each respective cellular constituent module in the set of cellular constituent modules, a respective numerical activation score 154 (e.g., 154-1-1, ... 154-1-K), and/or
  - optionally, for each respective perturbation signature in the set of perturbation signatures, a respective numerical activation score 156 (e.g., 156-1-1, ... 156-1-P); and
- a model including a plurality of parameters (e.g., 100 or more parameters), where the plurality of parameters is adjusted responsive to the difference between calculated activation scores and the numerical activation scores for a respective chemical structure.

In various embodiments, one or more of the above identified elements are stored in one or more of the previously mentioned memory devices and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 107 optionally stores a subset of the modules and data structures identified above. Furthermore, in some embodiments, the memory stores additional modules and data structures not described above. In some embodiments, one or more of the above identified elements is stored in a computer system, other than that of the system 100, that is addressable by the system 100 so that the system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 107, some or all of these data and modules instead may be stored in persistent memory 109 or in more than one memory. For example, in some embodiments, at least compound structure data store 120 and activation data structure 150 are stored in a remote storage device which can be a part of a cloud-based infrastructure. In some embodiments, at least compound structure data store 120 and activation data structure 150 are stored on a cloud-based infrastructure. In some embodiments, compound structure data store 120 and activation data structure 150 can also be stored in the remote storage device(s).

While a system in accordance with the present disclosure has been disclosed with reference to FIG. 1, methods 200, 300, 700, 800, 900, and 1500 in accordance with the present disclosure are now detailed with reference to FIGS. 2, 3, 7, 8, 9, and 14.

II. METHODS OF ASSOCIATING A TEST CHEMICAL COMPOUND WITH A PHYSIOLOGICAL CONDITION OF INTEREST

Physiological Conditions.

Referring to FIGS. 3A-3E, one aspect of the present disclosure provides a method 300 of associating a test chemical compound with a physiological condition of interest.

In some embodiments, the physiological condition of interest is a disease.

In some embodiments, the disease is selected from the group consisting of infectious or parasitic diseases; neoplasms; diseases of the blood or blood-forming organs; diseases of the immune system; endocrine, nutritional or metabolic diseases; mental, behavioral or neurodevelopmental disorders; sleep-wake disorders; diseases of the nervous system; diseases of the visual system; diseases of the ear or mastoid process; diseases of the circulatory system; diseases of the respiratory system; diseases of the digestive system; diseases of the skin; diseases of the musculoskeletal system or connective tissue; diseases of the genitourinary system; conditions related to sexual health; diseases related to pregnancy, childbirth or the puerperium; certain conditions originating in the perinatal period; and developmental anomalies. In some embodiments, the disease is one or more entries of the ICD-11 MMS, or the International Classification of Disease. The ICD provides a method of classifying diseases, injuries, and causes of death. The World Health Organization (WHO) publishes the ICDs to standardize the methods of recording and tracking instances of diagnosed disease.

In some embodiments, the physiological condition of interest is a disease stimulant such as a disease precondition or comorbidity.

In some embodiments, the physiological condition of interest occurs in, or is measured in the context of, a cell system. In some embodiments, the physiological condition of interest occurs in, or is measured in the context of, one or more cells, where the one or more cells includes single cells, cell lines, biopsy sample cells, and/or cultured primary cells. In some embodiments, the physiological condition of interest is a physiological condition occurring in human cells. In some embodiments, the physiological condition of interest is a physiological condition occurring in a sample, such as any of the samples described herein (see, for example, Definitions: Samples). In some embodiments, the physiological condition of interest is a physiological condition occurring in a subject, such as a human or an animal.

In some embodiments, the physiological condition of interest is, or is related to, a cellular process of interest.

In some embodiments, the cellular process of interest is an aberrant cell process. In some embodiments, the cellular process of interest is a cell process associated with a disease. For example, as described above, in some embodiments, the method provides for the targeting and elucidation of cellular processes and programs that are critical to disease. In some embodiments, the cellular process of interest is indicative of or related to a mechanism underlying any of the characteristics of disease, including but not limited to onset, progression, symptoms, severity, and/or resolution of disease. In some embodiments, the cellular process of interest is a functional pathway. In some embodiments, the cellular process of interest is a signaling pathway. In some embodiments, the cellular process of interest is a mechanism of action (e.g., of a compound, a small molecule, and/or a therapeutic). In some embodiments, the cellular process of interest is characterized and/or modulated by a transcriptional network (e.g., a gene regulatory network). In some embodiments, the cellular process of interest is a cellular process that occurs during a transition between a first cell state and a second cell state.

In some embodiments, the cellular process of interest is an annotation, such as a gene set enrichment assay (GSEA) annotation, a gene ontology annotation, a functional and/or signaling pathway annotation, and/or a cellular signature annotation. Annotations can be obtained from any public knowledge database, including but not limited to the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, the Gene Ontology project, and/or any disease-specific database.

Thus, in some embodiments, the physiological condition of interest is any respective disease, functional pathway, signaling pathway, mechanism of action, transcriptional network, discrepancy, and/or cellular or biological process as described herein.

In some embodiments, the physiological condition of interest is a phenotype. For instance, in some embodiments, the physiological condition of interest is a physiological manifestation of a compound, a small molecule, and/or a therapeutic, such as toxicity and/or resolution of a disease. In some embodiments, the physiological condition is a phenotype measured using experimental data including, but not limited to, flow cytometry readouts, imaging and microscopy annotations (e.g., H&E slides, IHC slides, radiology images, and/or other medical imaging), and/or cellular constituent data.

In some embodiments, the physiological condition of interest is a measure of toxicity. In some embodiments, the physiological condition is inhibition or activation of a nuclear receptor, and/or an amount of inhibition or an amount of activation of a nuclear receptor. In some embodiments, the physiological condition is inhibition or activation, and/or an amount of inhibition or an amount of activation of a biological pathway (e.g., a stress response pathway). Example nuclear receptors and example stress response pathways, as well as inhibition or activation data for these nuclear receptors and example stress response pathways that can be used in the present disclosure, are described for approximately 10,000 compounds as described in Huang et al., 2016, "Modelling the Tox21 10 K chemical profiles for in vivo toxicity prediction and mechanism characterization," Nat Commun. 7, p. 10425, which is hereby incorporated by reference.

In some embodiments, the physiological condition of interest is characterized by an activation of a set of cellular constituents (e.g., a cellular constituent module) and/or a perturbation signature (e.g., a differential expression profile of a plurality of analytes in response to a perturbation).

For example, in some embodiments the physiological condition of interest is a cellular constituent module comprising a set of cellular constituents. Any type of analyte (e.g., a gene, a transcript, a carbohydrate, a lipid, an epigenetic feature, a metabolite, a protein, or a combination thereof) is contemplated for use in the set of cellular constituents in a respective cellular constituent module. In some embodiments, the cellular constituent module is associated with any cellular or biological process known in the art, as well as any aberrations thereof, as will be apparent to one skilled in the art. Cellular constituent modules suitable for use with the presently disclosed systems and methods are further described in the section entitled "Cellular constituents and cellular constituent modules," below.

In some embodiments, the physiological condition of interest is a perturbation signature characterized by a discrepancy between a first cell state and a second cell state (e.g., a cell state transition signature).

In some such embodiments, the physiological condition of interest is identified by a discrepancy between a diseased state (e.g., a cell obtained from a diseased subject and/or a diseased tissue) and a healthy state (e.g., a cell obtained from a healthy or control subject and/or tissue). For instance, in some embodiments, a diseased state is identified by loss of a function of a cell, gain of a function of a cell, progression of a cell (e.g., transition of the cell into a differentiated state), stasis of a cell (e.g., inability of the cell to transition into a differentiated state), intrusion of a cell (e.g., emergence of the cell in an abnormal location), disappearance of a cell (e.g., absence of the cell in a location where the cell is normally present), disorder of a cell (e.g., a structural, morphological, and/or spatial change within and/or around the cell), loss of network of a cell (e.g., a change in the cell that eliminates normal effects in progeny cells or cells downstream of the cell), a gain of network of a cell (e.g., a change in the cell that triggers new downstream effects in progeny cells of cells downstream of the cell), a surplus of a cell (e.g., an overabundance of the cell), a deficit of a cell (e.g., a density of the cell being below a critical threshold), a difference in cellular constituent ratio and/or quantity in a cell, a difference in the rate of transitions in a cell, or any combination thereof.

Perturbation signatures suitable for use with the presently disclosed systems and methods are further described in the section entitled "Perturbation signatures," below.

In some embodiments, the physiological condition of interest includes a plurality of physiological conditions (e.g., cellular processes, cellular constituent modules, and/or perturbation signatures). In some embodiments, the physiological condition of interest includes at least 3, at least 4, at least 5, at least 6, at least 7, at least 8, at least 9, at least 10, at least 15, at least 20, at least 30, at least 40, at least 50, at least 60, at least 70, at least 80, at least 90, or at least 100 physiological conditions. In some embodiments, the physiological condition of interest includes no more than 200, no more than 100, no more than 90, no more than 80, no more than 70, no more than 60, no more than 50, no more than 20, or no more than 10 physiological conditions. In some embodiments, the physiological condition of interest comprises from 1 to 5, from 5 to 10, from 2 to 20, from 10 to 50, or from 20 to 100 physiological conditions. In some embodiments, the physiological condition of interest includes a plurality of physiological conditions that falls within another range starting no lower than 3 physiological conditions and ending no higher than 200 physiological conditions.

In some embodiments a compound of the present disclosure is a chemical compound that satisfies the Lipinski rule of five criterion. In some embodiments, a compound of the present disclosure is an organic compounds that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, Adv. Drug Del. Rev. 23, 3, which is hereby incorporated herein by reference in its entirety. In some embodiments, a compound of the present disclosure satisfies one or more criteria in addition to Lipinski's Rule of Five. For example, in some embodiments, a compound of the present disclosure has five or fewer aromatic rings, four or fewer aromatic rings, three or fewer aromatic rings, or two or fewer aromatic rings.

Referring to Block 302, the method 300 includes obtaining a fingerprint of a chemical structure of the test chemical compound.

For instance, in some implementations, application of the test chemical compound to a machine learning approach includes transforming molecular data (e.g., the chemical structure of the compound) into a format that can be read and manipulated by the machine learning model.

Figure 3A:
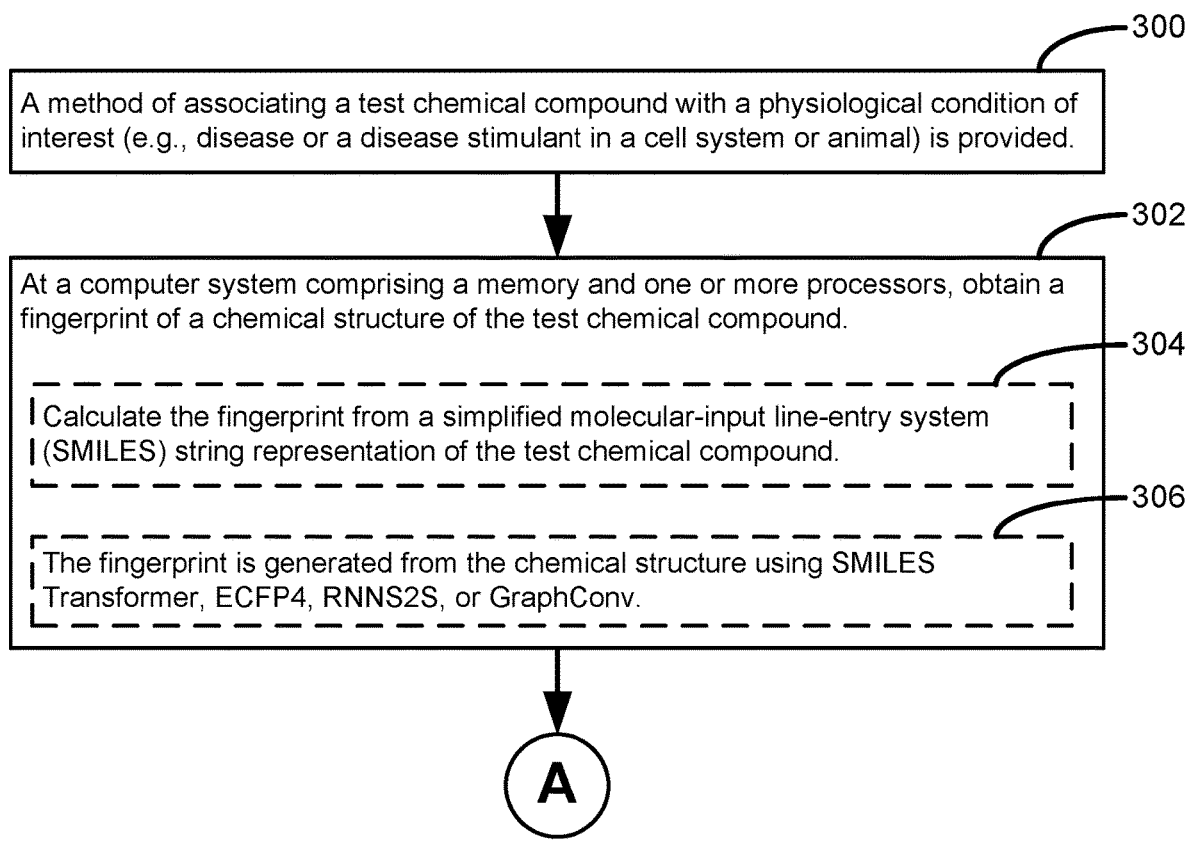
FIGS. 3A, 3B, 3C, 3D, and 3E provide a flow chart of processes and features of an example method for associating a test chemical compound with a physiological condition of interest, in which dashed boxes represent optional elements, in accordance with various embodiments of the present disclosure.

Referring to Block 304 of FIG. 3A, one approach to transforming chemical structures into machine learning-readable formats includes determining a "fingerprint" of the chemical structure using a simplified molecular-input line-entry system (SMILES), which represents molecules as a string of text. Thus, in some embodiments, the method further comprises calculating the fingerprint from a simplified molecular-input line-entry system (SMILES) string representation of the test chemical compound. Molecular fingerprinting using SMILES strings is further described, for example, in Honda et al., 2019, "SMILES Transformer: Pre-trained Molecular Fingerprint for Low Data Drug Discovery," arXiv:1911.04738, which is hereby incorporated herein by reference in its entirety.

Another approach to transforming chemical structures into machine-learning readable formats includes determining a graph-based molecular fingerprint. In graph-based molecular fingerprinting, the original molecular structure is represented by a graph, in which nodes represent individual atoms and edges represent bonds between atoms. Graph-based approaches provide several advantages, including the ability to efficiently encode multiple substructures with lower size requirements and thus lower computational burden, as well as the ability to encode indications of structural similarity between fingerprints. Graph-based fingerprinting is further described, for instance, in Duvenaud et al., 2015, "Convolutional networks on graphs for learning molecular fingerprints," NeurIPS, 2224-2232, which is hereby incorporated herein by reference in its entirety. In some embodiments, the fingerprint is generated from a graph convolutional network. In some embodiments, the fingerprint is generated from a spatial graph convolutional network, such as a graph attention network (GAT), a graph isomorphism network (GIN), or a graph substructure index-based approximate graph (SAGA). In some embodiments, the fingerprint is generated from a spectral graph convolutional network, such as a spectral graph convolution using Chebyshev polynomial filtering.

Referring to Block 306 of FIG. 3A, in some embodiments, the fingerprint is generated from the chemical structure using SMILES Transformer, ECFP4, RNNS2S, and/or GraphConv.

Model Architectures.

Figure 3B:
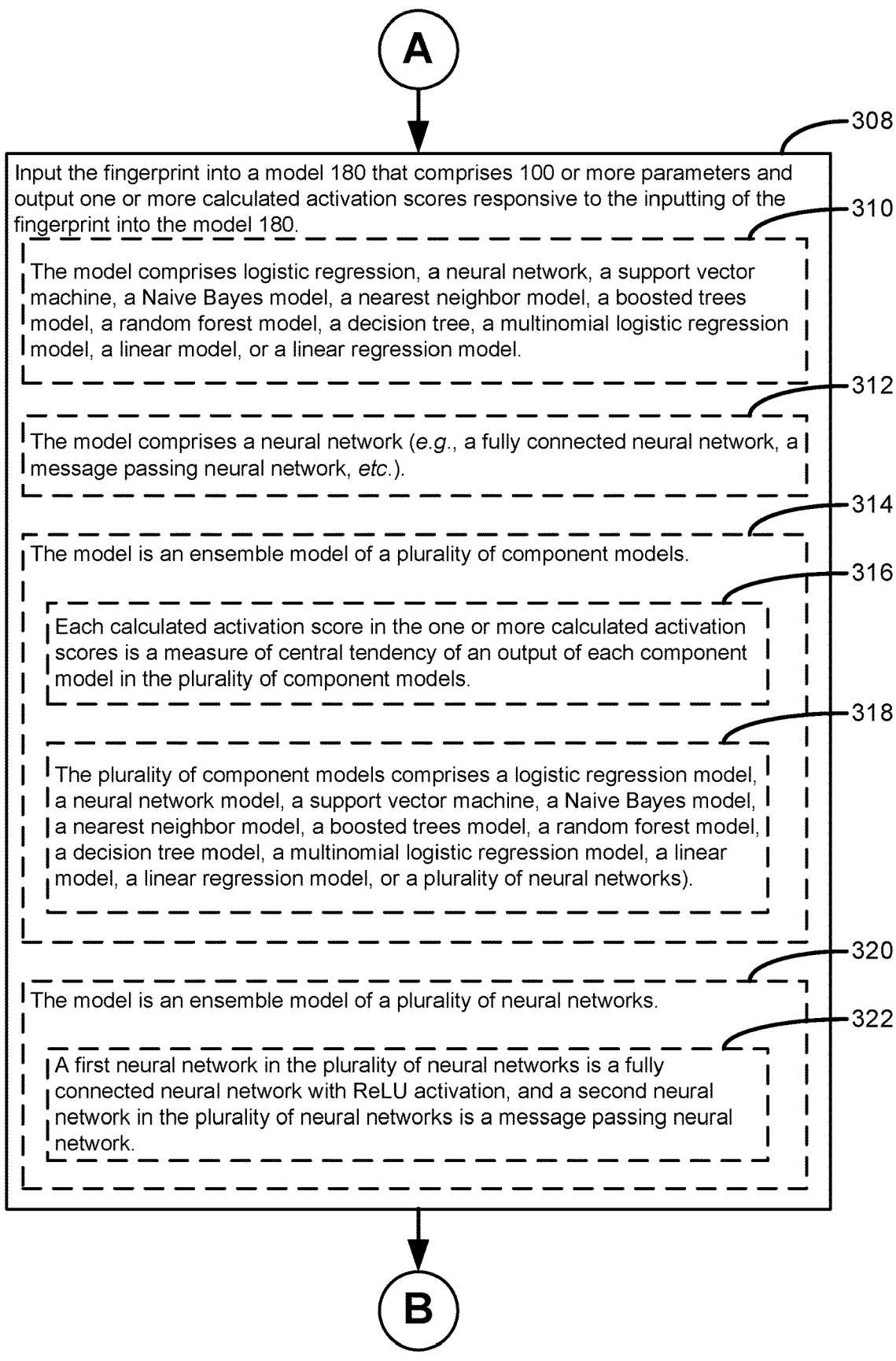

Referring to Block 308 of FIG. 3B, the method includes inputting the fingerprint into a model. In some embodiments the model comprises a plurality (e.g., 100, 200, 300, 500, 1000, 10,000 or more) of parameters.

In some embodiments, the model comprises a plurality of parameters (e.g., weights and/or hyperparameters). In some embodiments, the plurality of parameters for the model comprises at least 10, at least 50, at least 100, at least 500, at least 1000, at least 2000, at least 5000, at least 10,000, at least 20,000, at least 50,000, at least 100,000, at least 200,000, at least 500,000, at least 1 million, at least 2 million, at least 3 million, at least 4 million or at least 5 million parameters. In some embodiments, the plurality of parameters for the model comprises no more than 8 million, no more than 5 million, no more than 4 million, no more than 1 million, no more than 500,000, no more than 100,000, no more than 50,000, no more than 10,000, no more than 5000, no more than 1000, or no more than 500 parameters. In some embodiments, the plurality of parameters for the model comprises from 10 to 5000, from 500 to 10,000, from 10,000 to 500,000, from 20,000 to 1 million, or from 1 million to 5 million parameters. In some embodiments, the plurality of parameters for the model falls within another range starting no lower than 10 parameters and ending no higher than 8 million parameters.

In some embodiments, the training of the model is further characterized by one or more hyperparameters (e.g., one or more values that may be tuned during training). In some embodiments, the hyperparameter values are tuned (e.g., adjusted) during training. In some embodiments, the hyperparameter values are determined based on the specific elements of the training dataset and/or one or more inputs (e.g., cells, cellular constituent modules, covariates, etc.). In some embodiments, the hyperparameter values are determined using experimental optimization. In some embodiments, the hyperparameter values are determined using a hyperparameter sweep. In some embodiments, the hyperparameter values are assigned based on prior template or default values.

In some embodiments, a respective hyperparameter of the one or more hyperparameters comprises a learning rate. In some embodiments, the learning rate is at least 0.0001, at least 0.0005, at least 0.001, at least 0.005, at least 0.01, at least 0.05, at least 0.1, at least 0.2, at least 0.3, at least 0.4, at least 0.5, at least 0.6, at least 0.7, at least 0.8, at least 0.9, or at least 1. In some embodiments, the learning rate is no more than 1, no more than 0.9, no more than 0.8, no more than 0.7, no more than 0.6, no more than 0.5, no more than 0.4, no more than 0.3, no more than 0.2, no more than 0.1 no more than 0.05, no more than 0.01, or less. In some embodiments, the learning rate is from 0.0001 to 0.01, from 0.001 to 0.5, from 0.001 to 0.01, from 0.005 to 0.8, or from 0.005 to 1. In some embodiments, the learning rate falls within another range starting no lower than 0.0001 and ending no higher than 1. In some embodiments, the one or more hyperparameters further include regularization strength (e.g., L2 weight penalty, dropout rate, etc.). For instance, in some embodiments, the model (e.g., a neural network) is trained using a regularization on a corresponding parameter (e.g., weight) of each hidden neuron in the plurality of hidden neurons. In some embodiments, the regularization includes an L1 or L2 penalty.

In some embodiments, a respective hyperparameter of the one or more hyperparameters is a loss function. In some embodiments, the loss function is mean square error, flattened mean square error, quadratic loss, mean absolute error, mean bias error, hinge, multi-class support vector machine, and/or cross-entropy. In some embodiments, the loss function is a gradient descent algorithm and/or a minimization function.

In some embodiments, the model is associated with one or more activation functions. In some embodiments, an activation function in the one or more activation functions is tan h, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, swish, mish, Gaussian error linear unit (GeLU), and/or thin plate spline. The model outputs one or more calculated activation scores responsive to the inputting of the fingerprint into the model.

Referring to Block 310 of FIG. 3B, in some embodiments, the model comprises a logistic regression model, a neural network model, a support vector machine model, a Naive Bayes model, a nearest neighbor model, a boosted trees model, a random forest model, a decision tree model, a multinomial logistic regression model, a linear model, and/or a linear regression model. In some embodiments, the model is a regressor. In some embodiments, the model is any of the models disclosed herein (see, for example, Definitions: Models).

Referring to Block 312 of FIG. 3B, in some embodiments, the model comprises a neural network.

In some embodiments, the neural network is a fully connected neural network with ReLU activation. For instance, in some embodiments, the model is a neural network comprising a corresponding one or more inputs, where each input in the corresponding one or more inputs is for a chemical structure for a test chemical compound, a corresponding first hidden layer comprising a corresponding plurality of hidden neurons, where each hidden neuron in the corresponding plurality of hidden neurons (i) is fully connected to each input in the plurality of inputs, (ii) is associated with a first activation function type, and (iii) is associated with a corresponding parameter (e.g., weight) in a plurality of parameters for the neural network, and one or more corresponding neural network outputs, where each respective neural network output in the corresponding one or more neural network outputs (i) directly or indirectly receives, as input, an output of each hidden neuron in the corresponding plurality of hidden neurons, and (ii) is associated with a second activation function type. In some such embodiments, the neural network is a fully connected network.

In some embodiments, the neural network comprises a plurality of hidden layers. As described above, hidden layers are located between input and output layers (e.g., to capture additional complexity). In some embodiments, where there is a plurality of hidden layers, each hidden layer may have a same or a different respective number of neurons.

In some embodiments, each hidden neuron (e.g., in a respective hidden layer in a neural network) is associated with an activation function that performs a function on the input data (e.g., a linear or non-linear function). Generally, the purpose of the activation function is to introduce non-linearity into the data such that the neural network is trained on representations of the original data and can subsequently "fit" or generate additional representations of new (e.g., previously unseen) data. Selection of activation functions (e.g., a first and/or a second activation function) is dependent on the use case of the neural network, as certain activation functions can lead to saturation at the extreme ends of a dataset (e.g., tan h and/or sigmoid functions). For instance, in some embodiments, an activation function (e.g., a first and/or a second activation function) is selected from any suitable activation functions known in the art, including but not limited to any activation function disclosed herein.

In some embodiments, each hidden neuron is further associated with a parameter (e.g., a weight and/or a bias value) that contributes to the output of the neural network, determined based on the activation function. In some embodiments, the hidden neuron is initialized with arbitrary parameters (e.g., randomized weights). In some alternative embodiments, the hidden neuron is initialized with a predetermined set of parameters.

In some embodiments, the plurality of hidden neurons in a neural network (e.g., across one or more hidden layers) is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, or at least 500 neurons. In some embodiments, the plurality of hidden neurons is at least 100, at least 500, at least 800, at least 1000, at least 2000, at least 3000, at least 4000, at least 5000, at least 6000, at least 7000, at least 8000, at least 9000, at least 10,000, at least 15,000, at least 20,000, or at least 30,000 neurons. In some embodiments, the plurality of hidden neurons is no more than 30,000, no more than 20,000, no more than 15,000, no more than 10,000, no more than 9000, no more than 8000, no more than 7000, no more than 6000, no more than 5000, no more than 4000, no more than 3000, no more than 2000, no more than 1000, no more than 900, no more than 800, no more than 700, no more than 600, no more than 500, no more than 400, no more than 300, no more than 200, no more than 100, or no more than 50 neurons. In some embodiments, the plurality of hidden neurons is from 2 to 20, from 2 to 200, from 2 to 1000, from 10 to 50, from 10 to 200, from 20 to 500, from 100 to 800, from 50 to 1000, from 500 to 2000, from 1000 to 5000, from 5000 to 10,000, from 10,000 to 15,000, from 15,000 to 20,000, or from 20,000 to 30,000 neurons. In some embodiments, the plurality of hidden neurons falls within another range starting no lower than 2 neurons and ending no higher than 30,000 neurons.

In some embodiments, the neural network comprises from 1 to 50 hidden layers. In some embodiments, the neural network comprises from 1 to 20 hidden layers. In some embodiments, the neural network comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, or at least 100 hidden layers. In some embodiments, the neural network comprises no more than 100, no more than 90, no more than 80, no more than 70, no more than 60, no more than 50, no more than 40, no more than 30, no more than 20, no more than 10, no more than 9, no more than 8, no more than 7, no more than 6, or no more than 5 hidden layers. In some embodiments, the neural network comprises from 1 to 5, from 1 to 10, from 1 to 20, from 10 to 50, from 2 to 80, from 5 to 100, from 10 to 100, from 50 to 100, or from 3 to 30 hidden layers. In some embodiments, the neural network comprises a plurality of hidden layers that falls within another range starting no lower than 1 layer and ending no higher than 100 layers.

In some embodiments, the neural network comprises a shallow neural network. A shallow neural network refers to a neural network with a small number of hidden layers. In some embodiments, such neural network architectures improve the efficiency of neural network training and conserve computational power due to the reduced number of layers involved in the training. In some embodiments, the neural network comprises one hidden layer. In some embodiments, the neural network comprises two, three, four, or five hidden layers.

In some embodiments, the neural network is a message passing neural network. A message passing neural network refers to a framework for supervised learning on graphs (e.g., graph-based representations of chemical structures), where nodes represent atoms and edges represent bonds between atoms. Generally, a message passing neural network comprises two phases in the forward pass, a message passing phase and a readout phase. The message passing phase runs for a period of T intervals and comprises updating hidden states at each node in the graph in accordance with message functions Mt and vertex update functions $U_t$. The readout phase computes a feature vector for the graph using a readout function R. In some embodiments, the message passing neural network comprises a convolutional network (e.g., a spatial graph convolutional network and/or a spectral graph convolutional network), a gated graph neural network (GG-NN), an interaction network, a molecular graph convolution, a deep tensor neural network, and/or a Laplacian-based method. See, for example, Gilmer et al., 2017, "Neural Message Passing for Quantum Chemistry," arXiv:1704.01212v2, which is hereby incorporated herein by reference in its entirety.

Referring to Block 314 of FIG. 3B, in some embodiments, the model is an ensemble model of a plurality of component models. For instance, referring to Block 316, in some embodiments each calculated activation score in the one or more calculated activation scores is measure of central tendency of an output of each component model in the plurality of component models.

Referring to Block 318 of FIG. 3B, in some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, a linear regression model, or a plurality of neural networks.

In some embodiments, the ensemble model comprises at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, or at least 500 component models. In some embodiments, the ensemble model comprises no more than 500, no more than 400, no more than 300, no more than 200, or no more than 100 component models. In some embodiments, the ensemble model comprises no more than 100, no more than 50, no more than 40, no more than 30, or no more than 20 component models. In some embodiments, the ensemble model comprises between 1 and 50, between 2 and 20, between 5 and 50, between 10 and 80, between 5 and 15, between 3 and 30, between 10 and 500, between 2 and 100, or between 50 and 100 component models. In some embodiments, the ensemble model comprises another range of component models starting no lower than 2 component models and ending no higher than 500 component models.

In some embodiments, the ensemble model is formed by combining a plurality of outputs (e.g., activation scores) obtained from the plurality of component models. In some embodiments, the plurality of outputs (e.g., activation scores) from the classifiers is combined using any measure of central tendency known in the art, including but not limited to a mean, median, mode, weighted mean, weighted median, weighted mode, arithmetic mean, midrange, midhinge, trimean, and/or Winsorized mean. For instance, the final determination from the ensemble model can be obtained based on the average of the outputs across all component models in the ensemble model.

In some embodiments, the plurality of outputs is combined using a voting method. For example, in some embodiments, the plurality of outputs is combined by tallying the number of outputs (e.g., activation scores), from each component model in the ensemble model, that indicate an association between a respective chemical structure and a respective physiological condition of interest. In some embodiments, the plurality of outputs (e.g., activation scores) from the component models is combined using a majority vote. In some such embodiments, the plurality of outputs from the component models is combined by determining an association between a respective chemical structure and a respective physiological condition of interest when the tally of outputs indicating an association (e.g., tally of activation scores that exceed a threshold criterion) is greater than a voting threshold. In some embodiments, the voting threshold is at least 50% of total votes from the plurality of component models in the ensemble model. In some embodiments, the voting threshold is at least 20%, at least 30%, at least 40%, at least 50%, at least 60%, at least 70%, at least 80%, at least 90%, or at least 95% of total votes from the plurality of component models in the ensemble model.

In some embodiments, each component model in the ensemble model is unweighted (e.g., each component model has one vote in the ensemble model). In some embodiments, one or more component models in the ensemble model is further weighted (e.g., has greater than 1 vote in the ensemble model).

In some embodiments, the method comprises obtaining a single ensemble model or a plurality of ensemble models. Any architecture known in the art is contemplated for the ensemble model. For instance, in some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, and/or a linear regression model. In some embodiments, the plurality of component models comprises a plurality of neural networks.

Referring to Block 320 of FIG. 3B, in some embodiments, the model is an ensemble model of a plurality of neural networks. Referring to Block 322 of FIG. 3B, in some embodiments, the model is an ensemble model comprising a plurality of neural networks, where a first neural network in the plurality of neural networks is a fully connected neural network with ReLU activation, and a second neural network in the plurality of neural networks is a message passing neural network. In some such embodiments, the first neural network is a fully connected 3-layer neural network that accepts, as input, a molecular fingerprint for a chemical structure as a SMILES representation. In some embodiments, the second neural network is a message passing neural network (MPNN) that accepts, as input, a molecular fingerprint for a chemical structure as a graph-based representation.

Cellular Constituents and Cellular Constituent Modules.

As described above, referring again to Block 308, responsive to the inputting of a fingerprint for a chemical structure into the model, the model outputs one or more calculated activation scores for a set of cellular constituent modules. Referring to Block 326 of FIG. 3C, each respective calculated activation score in the one or more calculated activation scores represents a corresponding cellular constituent module in a set of cellular constituent modules.

Figure 3C:
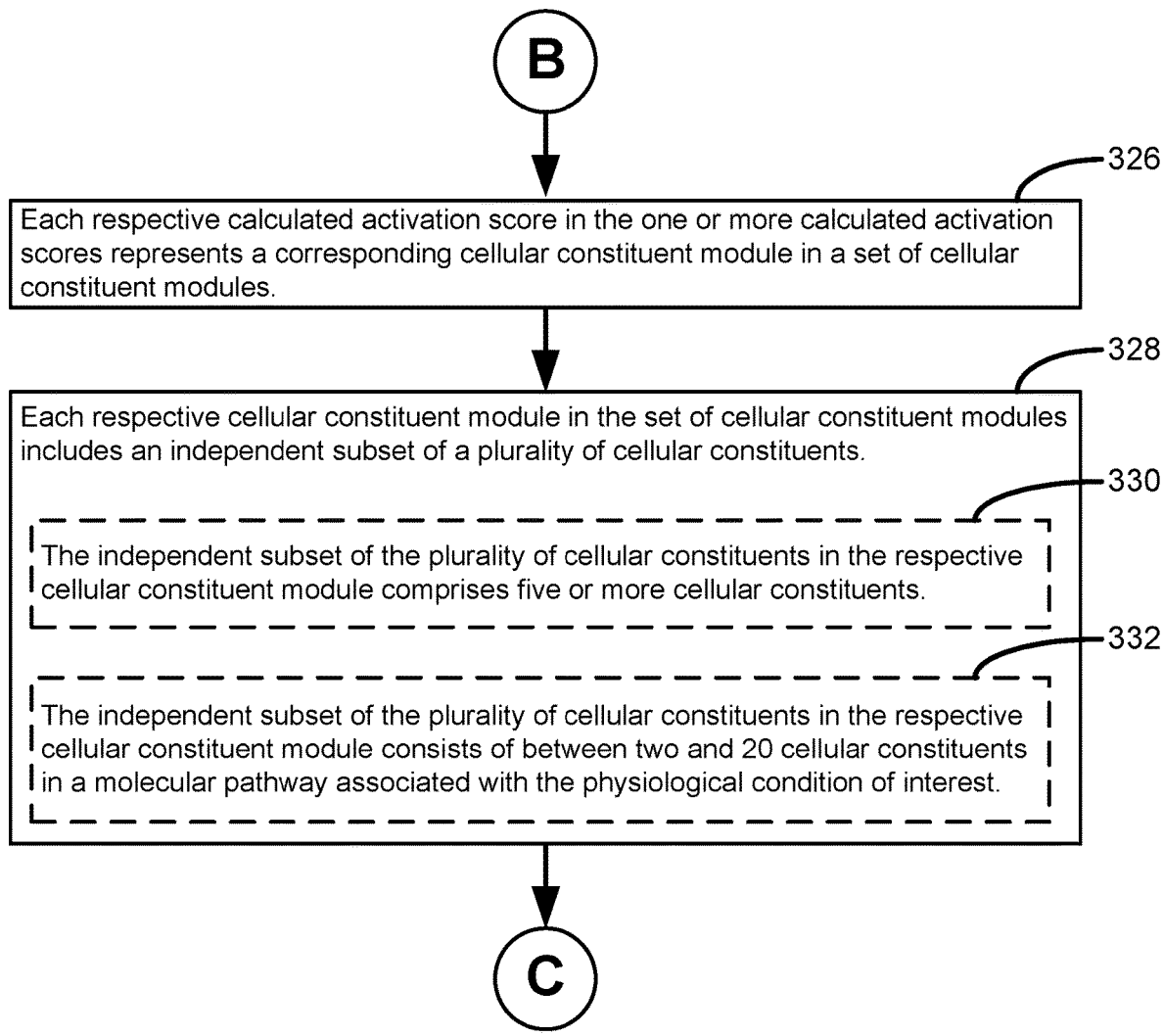

Referring to Block 328 of FIG. 3C, each respective cellular constituent module in the set of cellular constituent modules includes an independent subset of a plurality of cellular constituents.

In some embodiments, a cellular constituent is a gene, a gene product (e.g., an mRNA and/or a protein), a carbohydrate, a lipid, an epigenetic feature, a metabolite, and/or a combination thereof. In some embodiments, each cellular constituent in the plurality of cellular constituents is a particular gene, a particular mRNA associated with a gene, a carbohydrate, a lipid, an epigenetic feature, a metabolite, a protein, or a combination thereof. In some embodiments, the plurality of cellular constituents includes nucleic acids, including DNA, modified (e.g., methylated) DNA, RNA, including coding (e.g., mRNAs) or non-coding RNA (e.g., sncRNAs), proteins, including post-transcriptionally modified protein (e.g., phosphorylated, glycosylated, myristilated, etc. proteins), lipids, carbohydrates, nucleotides (e.g., adenosine triphosphate (ATP), adenosine diphosphate (ADP) and adenosine monophosphate (AMP)) including cyclic nucleotides such as cyclic adenosine monophosphate (cAMP) and cyclic guanosine monophosphate (cGMP), other small molecule cellular constituents such as oxidized and reduced forms of nicotinamide adenine dinucleotide (NADP/NADPH), and any combinations thereof.

In some embodiments, the plurality of cellular constituents comprises at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 20,000, at least 30,000, at least 50,000, or more than 50,000 cellular constituents. In some embodiments, the plurality of cellular constituents comprises no more than 70,000, no more than 50,000, no more than 30,000, no more than 10,000, no more than 5000, no more than 1000, no more than 500, no more than 200, no more than 100, no more than 90, no more than 80, no more than 70, no more than 60, no more than 50, or no more than 40 cellular constituents. In some embodiments, the plurality of cellular constituents consists of between twenty and 10,000 cellular constituents. In some embodiments, the plurality of cellular constituents consists of between 100 and 8,000 cellular constituents. In some embodiments, the plurality of cellular constituents comprises from 5 to 20, from 20 to 50, from 50 to 100, from 100 to 200, from 200 to 500, from 500 to 1000, from 1000 to 5000, from 5000 to 10,000, or from 10,000 to 50,000 cellular constituents. In some embodiments, the plurality of cellular constituents falls within another range starting no lower than 5 cellular constituents and ending no higher than 70,000 cellular constituents.

As an example, in some embodiments, the plurality of cellular constituents comprises a plurality of genes, optionally measured at the RNA level. In some embodiments, the plurality of genes comprises at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, or at least 1000 genes. In some embodiments, the plurality of genes comprises at least 1000, at least 2000, at least 3000, at least 4000, at least 5000, at least 10,000, at least 30,000, at least 50,000, or more than 50,000 genes. In some embodiments, the plurality of genes comprises from 5 to 20, from 20 to 50, from 50 to 100, from 100 to 200, from 200 to 500, from 500 to 1000, from 1000 to 5000, from 5000 to 10,000, or from 10,000 to 50,000 genes.

As another example, in some embodiments, the plurality of cellular constituents comprises a plurality of proteins. In some embodiments, the plurality of proteins comprises at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, or at least 1000 proteins. In some embodiments, the plurality of proteins comprises at least 1000, at least 2000, at least 3000, at least 4000, at least 5000, at least 10,000, at least 30,000, at least 50,000, or more than 50,000 proteins. In some embodiments, the plurality of proteins comprises from 5 to 20, from 20 to 50, from 50 to 100, from 100 to 200, from 200 to 500, from 500 to 1000, from 1000 to 5000, from 5000 to 10,000, or from 10,000 to 50,000 proteins.

There is no requirement that each cellular constituent in a cellular constituent module be unique. For instance, consider the case in which cellular constituent module A contains cellular constituents, 1, 3 and 10. Other cellular constituent modules in the set of cellular constituent modules can contain these cellular constituents as well. Here, the term "independent" means that the subset of the plurality of cellular constituents in a particular cellular constituent module is unique as a whole. Thus, considering the example cellular constituent module A above, another cellular constituent module in the set of cellular constituent modules may contain cellular constituents, 1, 3 and 10 provided that it further contains other cellular constituents that cellular constituent module A does not contain. Further considering the example cellular constituent module A above, another cellular constituent module in the set of cellular constituent modules may be limited to a subset of cellular constituents, 1, 3 and 10 provided with no requirement that it further contain other cellular constituents that cellular constituent module A does not contain (however, it could have such additional cellular constituents as well).

In some embodiments, each cellular constituent module in the set of cellular constituent modules comprises the same or a different number of cellular constituents in the respective independent subset of the plurality of cellular constituents. In some embodiments, each respective independent subset of cellular constituents corresponding to each respective cellular constituent module is a unique subset of cellular constituents (e.g., non-overlapping, where each cellular constituent in the plurality of cellular constituents is grouped into no more than one module). In some embodiments, a first cellular constituent module has a first subset of cellular constituents that overlaps a second subset of cellular constituents corresponding to a second cellular constituent module (e.g., overlapping, where at least one cellular constituent in the plurality of cellular constituents is common to two or more different modules).

Referring to Block 330 of FIG. 3C, in some embodiments, the independent subset of the plurality of cellular constituents in the respective cellular constituent module comprises five or more cellular constituents. In some embodiments, the independent subset of the plurality of cellular constituents in a respective cellular constituent module in the plurality of cellular constituent modules comprises at least 2, at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, or at least 3000 cellular constituents. In some embodiments, the independent subset of the plurality of cellular constituents comprises no more than 5000, no more than 3000, no more than 1000, no more than 500, no more than 200, no more than 100, no more than 90, no more than 80, no more than 70, no more than 60, or no more than 50 cellular constituents. In some embodiments, the independent subset of the plurality of cellular constituents comprises from 5 to 100, from 2 to 300, from 20 to 500, from 200 to 1000, or from 1000 to 5000 cellular constituents. In some embodiments, the independent subset of the plurality of cellular constituents falls within another range starting no lower than 2 cellular constituents and ending no higher than 5000 cellular constituents.

In some embodiments, the independent subset of the plurality of cellular constituents in the respective cellular constituent module consists of cellular constituents in a cellular process (e.g., a molecular pathway) associated with the physiological condition of interest. For instance, referring to Block 332 of FIG. 3C, in some embodiments, the independent subset of the plurality of cellular constituents in the respective cellular constituent module consists of between two and 20 cellular constituents in a molecular pathway associated with the physiological condition of interest.

Figure 3D:
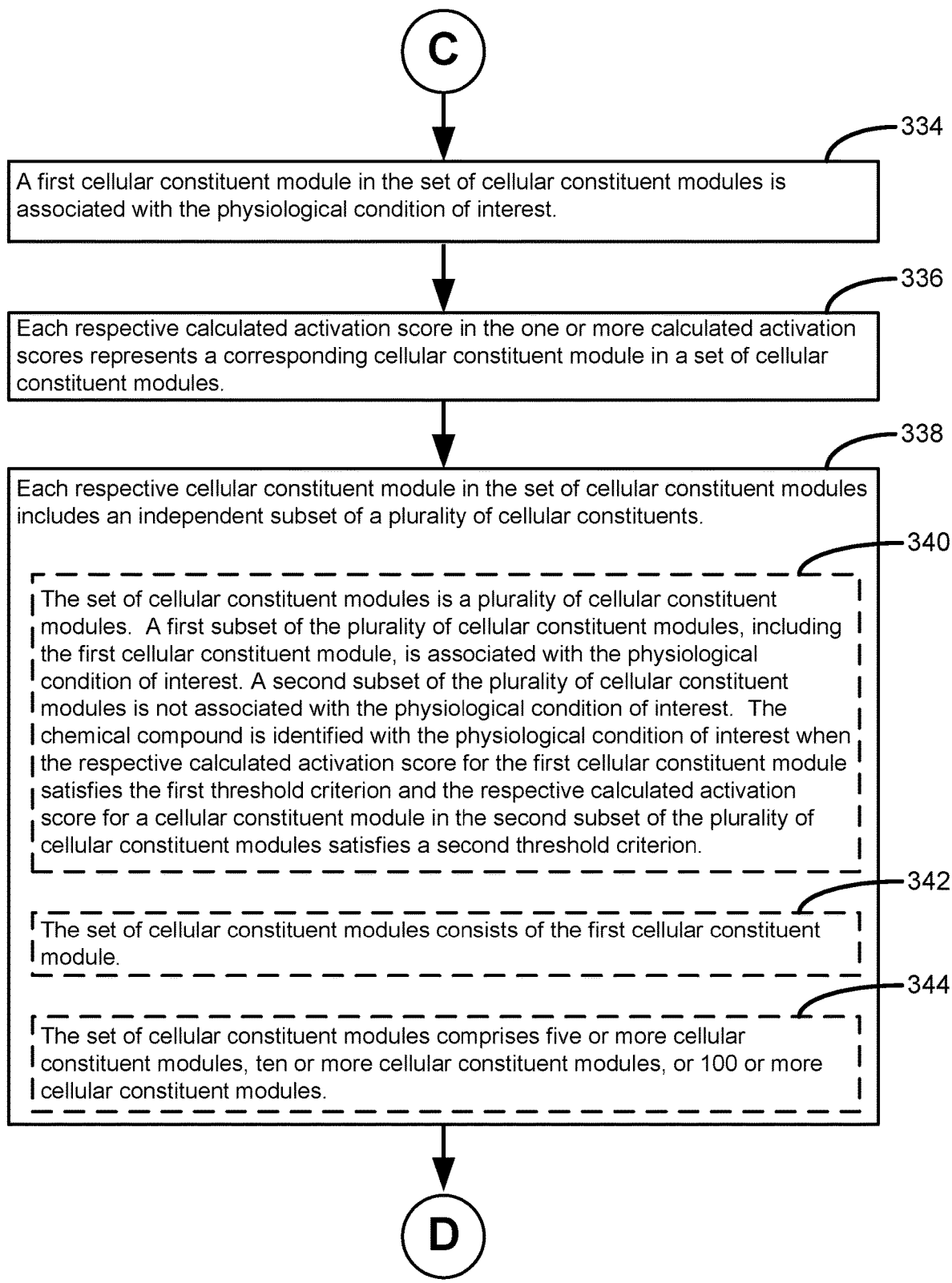

Referring to Block 334 of FIG. 3D, at least a first cellular constituent module in the set of cellular constituent modules is associated with the physiological condition of interest. In fact, numerous of the cellular constituent modules may be associated with the physiological condition of interest.

Referring to Block 336 of FIG. 3D, each respective calculated activation score in the one or more calculated activation scores represents a corresponding cellular constituent module in a set of cellular constituent modules.

Referring to Block 338 of FIG. 3D, each respective cellular constituent module in the set of cellular constituent modules includes an independent subset of a plurality of cellular constituents.

Referring to Block 340 of FIG. 3D, in some embodiments, the set of cellular constituent modules is a plurality of cellular constituent modules. A first subset of the plurality of cellular constituent modules, including the first cellular constituent module, is associated with the physiological condition of interest. That is, such cellular constituent modules represent the cellular constituents that are involved in the physiological condition of interest. For instance, such cellular constituents of such cellular constituent modules can be down-regulated or up-regulated in cells that represent the physiological condition of interest relative to cells in some baseline, wild-type state. Moreover, a second subset of the plurality of cellular constituent modules is not associated with the physiological condition of interest. That is, the cellular constituents of such cellular constituent modules represent the cellular constituents that are not involved in the physiological condition of interest. For instance, such cellular constituents are not down-regulated or up-regulated in cells representing the physiological condition of interest relative to cells in some baseline, wild-type state. In such embodiments, the chemical compound is identified with the physiological condition of interest when the respective calculated activation score for the first cellular constituent module (which is in the first subset of cellular constituent modules) satisfies a first threshold criterion and the respective calculated activation score for a cellular constituent module in the second subset of the plurality of cellular constituent modules satisfies a second threshold criterion. Example first threshold criterion are discussed below with respect to Block 348 of FIG. 3E. In general, what is sought are chemical compounds that identify (as demonstrated by having a calculated activation score satisfying the first threshold) with the cellular constituent modules in the first subset of cellular constituent modules but do not identify (as demonstrated by having a calculated activation score satisfying the second threshold) with the cellular constituent modules in the second subset of cellular constituent modules. For instance, in some embodiments, satisfaction of the first threshold requires an activation score above a first predetermined numerical value, whereas satisfaction of the second threshold requires an activation score below a second predetermined numerical value, where the exact first and second predetermined numerical values are application dependent.

As indicated above, in some implementations, the method comprises using one or more types of molecular data (e.g., cellular constituents) to characterize a physiological condition of interest (e.g., a cellular process). Such molecular data can comprise any analyte having a measurable attribute (e.g., an abundance and/or an expression level), such as omics profiling (e.g., transcriptomics, proteomics, metabolomics, etc.).

Generally, when associated with a cellular process, cellular constituent modules of cellular constituents (e.g., genes) can be thought to arise from a sequence of switching events, where cellular constituents (e.g., genes) that switch at similar times form a module together. Thus, for instance, in some embodiments, a respective cellular constituent module comprises a respective subset of the plurality of cellular constituents, where the subset of cellular constituents are grouped based upon a similarity of behavior associated with a respective physiological condition of interest (e.g., a cellular process of interest). In an example, a cellular constituent module associated with a respective physiological condition of interest can comprise a subset of genes that behaves similarly (e.g., exhibits similar expression profiles) across a plurality of cell types having the respective physiological condition.

Referring to Block 342 of FIG. 3D, in some embodiments, the set of cellular constituent modules consists of the first cellular constituent module.

Referring to Block 344 of FIG. 3D, in some embodiments, the set of cellular constituent modules comprises five or more cellular constituent modules. In some embodiments, the set of cellular constituent modules comprises 20 or more, 30 or more, 40 or more, 50 or more, 60 or more, 70 or more, 80 or more 90 or more, or 100 or more cellular constituent modules.

In some embodiments, the set of cellular constituent modules comprises at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or at least 5000 cellular constituent modules. In some embodiments, the set of cellular constituent modules comprises no more than 10,000, no more than 5000, no more than 2000, no more than 1000, no more than 500, no more than 300, no more than 200, no more than 100, no more than 90, no more than 80, no more than 70, no more than 60, or no more than 50 cellular constituent modules. In some embodiments, the set of cellular constituent modules consists of between 10 and 2000 cellular constituent modules. In some embodiments, the set of cellular constituent modules consists of between 50 and 500 cellular constituent modules. In some embodiments, the set of cellular constituent modules comprises from 5 to 20, from 20 to 50, from 50 to 100, from 100 to 200, from 200 to 500, from 500 to 1000, from 1000 to 5000, or from 5000 to 10,000 cellular constituent modules. In some embodiments, the set of cellular constituent modules falls within another range starting no lower than 5 cellular constituent modules and ending no higher than 10,000 cellular constituent modules.

In some embodiments, the method further comprises identifying cellular constituent modules associated with the physiological condition of interest. Such methods are discussed below in the section entitled Identifying cellular constituent modules in conjunction with FIGS. 14A-14D. Activation Scores.

As described in Block 308 of FIG. 3B, the model outputs one or more calculated activation scores responsive to the inputting of the fingerprint into the model. Generally, the output of a trained model (the model of Block 308) is defined through a process of learning on a training dataset including labels (e.g., numerical activation scores) and adjusting a plurality of parameters until the output of the trained model satisfies a minimum level of performance, such as through a validation step. Training models is further disclosed below in the section entitled, "Model training."

In some embodiments, an activation score in the one or more calculated activation scores is a respective activation weight for a respective cellular constituent module corresponding to a respective compound. For instance, in some embodiments, an activation score is an activation weight obtained as described in the section below entitled, "Identifying Cellular Constituent Modules," with reference to FIGS. 2A-B and 14A-D and illustrated in the activation data structure in FIG. 5, where the activation score indicates the activation (e.g., inducement and/or differential expression) of the respective (e.g., first) cellular constituent module, correlating to and/or in response to treatment with the respective compound.

Thus, in some such embodiments, the trained model provides, as output, the calculated activation score that indicates an association of the test chemical compound with the physiological condition of interest (e.g., the first cellular constituent module associated with the physiological condition of interest). Referring then to Block 348 of FIG. 3E, the method includes identifying (e.g., determining an association for) the chemical compound with the physiological condition of interest when the respective calculated activation score for the first cellular constituent module satisfies a first threshold criterion.

Figure 3E:
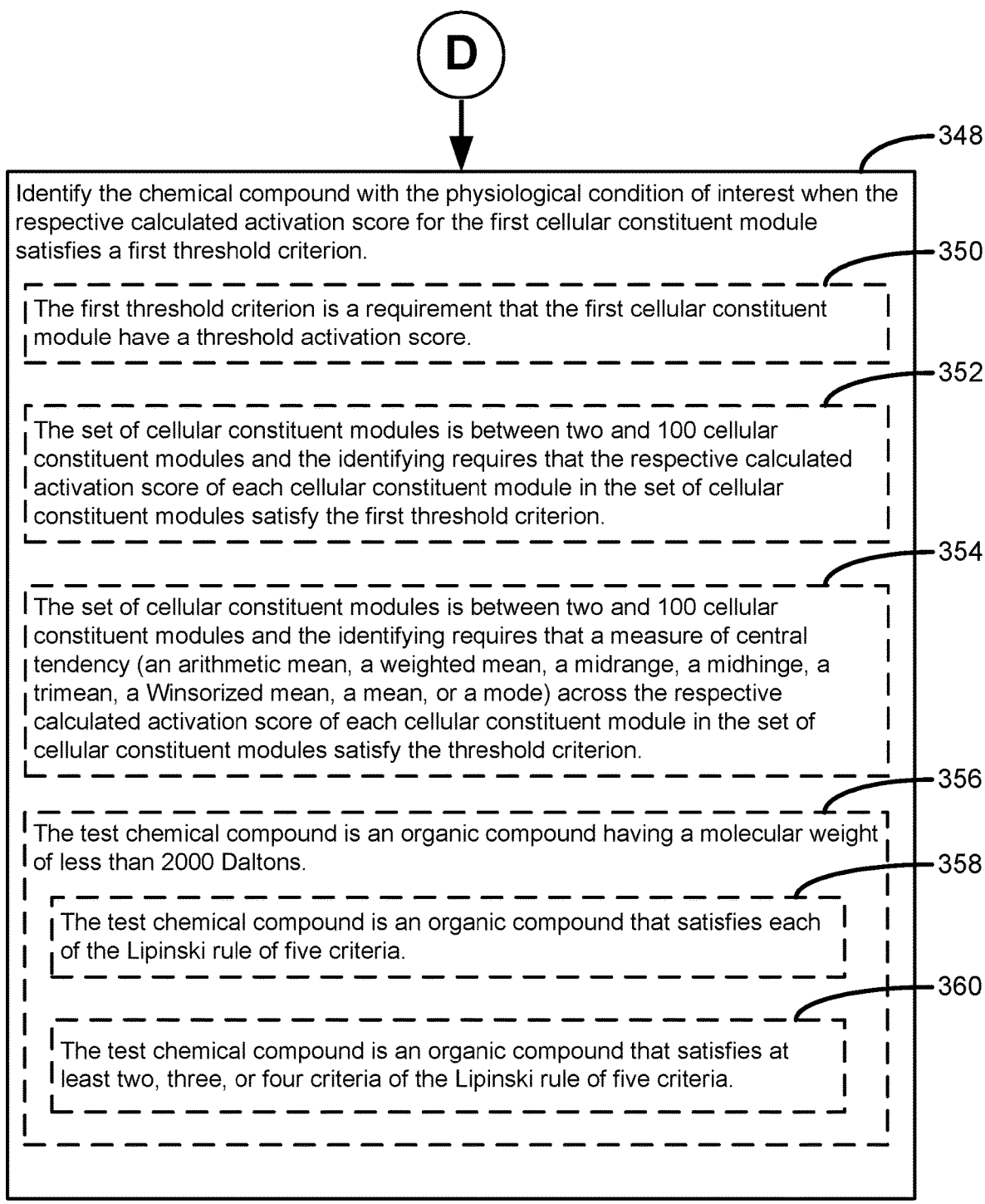

Referring to Block 350 of FIG. 3E, in some embodiments, the first threshold criterion is a requirement that the first cellular constituent module have a threshold activation score. In general, what is sought is a chemical compound that identifies (as demonstrated by having a calculated activation score satisfying the first threshold) with the physiological condition of interest. For instance, in some embodiments, satisfaction of the first threshold requires an activation score above a first predetermined numerical value.

For instance, in some embodiments the activation score is expressed as a normalized continuous value between "0" and "1" (or some other range "A" to "B" where A and B are two different numbers), where values closer to "1" (e.g., 0.89, 0.90, 0.91, 0.92, etc.) indicate a strong association between a cellular constituent module (and the chemical compound the cellular constituent module represents) and the physiological condition of interest. Values closer to "0" (e.g., 0.01, 0.02, 0.03, 0.04, etc.) indicate no association between the cellular constituent module (and the chemical compound the cellular constituent represents) and the physiological condition of interest. In such instances, a first threshold is chosen between "0" and "1" (or some other range "A" to "B" where A and B are two different numbers) and the cellular constituent module (and the chemical structures it represents) is deemed to be associated with the physiological condition of interest when the activation score is above the first threshold whereas the cellular constituent module (and the chemical structures it represents) is deemed to not be associated with the physiological condition of interest when the activation score is below the first threshold. In some such embodiments, the activation score is expressed as a normalized value in a continuous scale between "0" and "1" (or some other range "A" to "B" where A and B are two different numbers) and the first threshold is a value between 0 and 1, between 0.10 and 0.90, between 0.20 and 0.80, between 0.30 and 0.70, between 0.50 and 0.99, between 0.60 and 0.99, between 0.70 and 0.99, between 0.80 and 0.99, or between 0.90 and 0.99.

As another example, in some embodiments the activation score is expressed as a normalized value on continuous scale between "0" and "1" (or some other range "A" to "B" where A and B are two different numbers), where values closer to "1" (e.g., 0.89, 0.90, 0.91, 0.92, etc.) indicate no association between a cellular constituent module (and the chemical compound the cellular constituent module represents) and the physiological condition of interest. Values closer to "0" (e.g., 0.01, 0.02, 0.03, 0.04, etc.) indicate association between the cellular constituent module (and the chemical compound the cellular constituent represents) and the physiological condition of interest. In such instances, a first threshold is chosen between "0" and "1" (or some other range "A" to "B" where A and B are two different numbers) and the cellular constituent module (and the chemical structures it represents) is deemed to be associated with the physiological condition of interest when the activation score is below the first threshold whereas the cellular constituent module (and the chemical structures it represents) is deemed to not be associated with the physiological condition of interest when the activation score is above the first threshold. In some such embodiments, the activation score is expressed as a normalized value on a continuous scale between "0" and "1" (or some other range "A" to "B" where A and B are two different numbers) and the first threshold is a value between 0 and 1, between 0.10 and 0.90, between 0.20 and 0.80, between 0.30 and 0.70, between 0.50 and 0.99, between 0.60 and 0.99, between 0.70 and 0.99, between 0.80 and 0.99, or between 0.90 and 0.99.

Referring to block 352 of FIG. 3E, in some embodiments the set of cellular constituent modules is a plurality of cellular constituent modules (e.g., between two and 1000, between 10 and 100, between 2 and 100, between 4 and 50 cellular constituent modules), and the identifying of Block 348 requires that the respective calculated activation score of each cellular constituent module in the set of cellular constituent modules satisfy the first threshold criterion. For example, consider the case in which the set of cellular constituent modules consists of two cellular constituent modules: A and B. Block 352 of FIG. 3E requires that the activation score of cellular constituent modules A and B each satisfy the first threshold condition. For instance, consider the case in which cellular constituent module A has a calculated activation score of 0.25, cellular constituent module B has a calculated activation score of 0.75, and satisfaction of the first threshold condition requires that each activation score be greater than 0.4. In this instance the set of cellular constituent modules does not satisfy the requirements of Block 352 of FIG. 3E because each activation score is not greater than the 0.4 threshold requirement.

Referring to Block 354 of FIG. 3E, in some embodiments the set of cellular constituent modules is a plurality of cellular constituent modules (e.g., between two and 1000, between 10 and 100, between 2 and 100, between 4 and 50 cellular constituent modules) and the identifying of Block 348 requires that a measure of central tendency across the respective calculated activation score of each cellular constituent module in the set of cellular constituent modules satisfy the first threshold criterion. For example, consider the case in which the set of cellular constituent modules consists of two cellular constituent modules: A and B. Block 354 of FIG. 3E requires that some measure of central tendency of the activation score of cellular constituent modules A and B satisfy the first threshold condition. For instance, consider the case in which the measure of central tendency is averaging, cellular constituent module A has a calculated activation score of 0.25, cellular constituent module B has a calculated activation score of 0.75, and satisfaction of the first threshold condition requires that the average activation score be greater than 0.4. In this instance the set of cellular constituent modules satisfies the requirements of Block 354 of FIG. 3E because they have an average activation score of 0.25+0.75/2 or 0.5 which is greater than the 0.4 threshold requirement. In some embodiments, the measure of central tendency is an arithmetic mean, a weighted mean, a midrange, a midhinge, a trimean, a Winsorized mean, a mean, or a mode of each respective calculated activation score of each cellular constituent module in the set of cellular constituent modules.

Compounds.

In some embodiments, the test chemical compound is a small molecule, a biologic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other cellular-component editing system), and/or any combination of any of the foregoing.

In some embodiments, the test chemical compound is inorganic or organic.

For instance, with reference to Block 356 of FIG. 3E, in some embodiments, the test chemical compound is an organic compound having a molecular weight of less than 2000 Daltons (Da). In some embodiments, the test chemical compound has a molecular weight of at least 10 Da, at least 20 Da, at least 50 Da, at least 100 Da, at least 200 Da, at least 500 Da, at least 1 kDa, at least 2 kDa, at least 3 kDa, at least 5 kDa, at least 10 kDa, at least 20 kDa, at least 30 kDa, at least 50 kDa, at least 100 kDa, or at least 500 kDa. In some embodiments, the test chemical compound has a molecular weight of no more than 1000 kDa, no more than 500 kDa, no more than 100 kDa, no more than 50 kDa, no more than 10 kDa, no more than 5 kDa, no more than 2 kDa, no more than 1 kDa, no more than 500 Da, no more than 300 Da, no more than 100 Da, or no more than 50 Da. In some embodiments, the test chemical compound has a molecular weight of from 10 Da to 900 Da, from 50 Da to 1000 Da, from 100 Da to 2000 Da, from 1 kDa to 10 kDa, from 5 kDa to 500 kDa, or from 100 kDa to 1000 kDa. In some embodiments, the test chemical compound has a molecular weight that falls within another range starting no lower than 10 Daltons and ending no higher than 1000 kDa.

With reference to Block 358 of FIG. 3E, in some embodiments, the test chemical compound is an organic compound that satisfies each of the Lipinski rule of five criteria. The Lipinski rule of five (e.g., RO5) criteria are a set of guidelines used to evaluate druglikeness, such as to determine whether a respective compound with a respective pharmacological or biological activity has corresponding chemical or physical properties suitable for administration in humans. Lipinski's rule of five includes the following criteria for determining the druglikeness of a compound: (i) a molecular mass less than 500 Da, (ii) no more than 5 hydrogen bond donors, (iii) no more than 10 hydrogen bond acceptors, and (iv) an octanol-water partition coefficient log P not greater than 5.

With reference to Block 360 of FIG. 3E, in some embodiments, the test chemical compound is an organic compound that satisfies at least two, three or four criteria of the Lipinski rule of five criteria. In some embodiments, the test chemical compound is an organic compound that satisfies zero, one, two, three, or all four criteria of the Lipinski rule of five criteria.

In some embodiments, the test chemical compound is selected from a database. Examples of suitable compound databases that provide results from drug screens, annotations, and/or general information such as compound targets and chemical properties of compounds include, but are not limited to, the Genomics of Drug Sensitivity in Cancer, the Cancer Therapeutics Response Portal, the Connectivity Map, PharmacoDB, the Base of Bioisosterically Exchangeable Replacements (BoBER), and/or DrugBank. In some embodiments, the test chemical compound is selected from a database that provides information on genes and gene products, perturbation-induced cellular constituent signatures, and/or pathway annotations. Examples of suitable databases include, but are not limited to, the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

Using the Result of Method 300 in Practical Applications.

In some embodiments method 300 described above in conjunction with FIG. 3 is used to evaluate a plurality of test compounds against a physiological condition of interest. In such embodiments, each test compound in the plurality of test compounds is run through the method 300 of FIG. 3. Thus, if there are 100 test compounds and one physiological condition of interest, in such embodiments, method 300 is run 100 times, where each instance in the 100 times is for a different one of the test compounds.

Moreover, in some embodiments, method 300 described above in conjunction with FIG. 3 is used to evaluate a plurality of compounds against a plurality of physiological condition of interests. In such embodiments, for each physiological condition of interest, each respective each test compound in the plurality of test compounds is run through the method 300 of FIG. 3. Thus, if there are 100 test compounds and two physiological conditions of interest, in such embodiments, method 300 is run 200 times, where each instance in the 200 times is for a different one of the test compounds against either the first or the second physiological condition of interest.

In some embodiments, the plurality of test compounds includes at least 5, at least 10, at least 15, at least 20, at least 30, at least 40, at least 50, at least 100, at least 200, at least 300, at least 400, at least 500, at least 800, at least 1000, at least 2000, at least 3000, at least 4000, at least 5000, at least 8000, at least 10,000, at least 20,000, at least 30,000, at least 50,000, at least 80,000, at least 100,000, at least 200,000, at least 500,000, at least 800,000, at least 1 million, or at least 2 million test compounds and there is a single physiological condition of interest. In some such embodiments, method 300 is run at least 5, at least 10, at least 15, at least 20, at least 30, at least 40, at least 50, at least 100, at least 200, at least 300, at least 400, at least 500, at least 800, at least 1000, at least 2000, at least 3000, at least 4000, at least 5000, at least 8000, at least 10,000, at least 20,000, at least 30,000, at least 50,000, at least 80,000, at least 100,000, at least 200,000, at least 500,000, at least 800,000, at least 1 million, or at least 2 million times to realize at least 5, at least 10, at least 15, at least 20, at least 30, at least 40, at least 50, at least 100, at least 200, at least 300, at least 400, at least 500, at least 800, at least 1000, at least 2000, at least 3000, at least 4000, at least 5000, at least 8000, at least 10,000, at least 20,000, at least 30,000, at least 50,000, at least 80,000, at least 100,000, at least 200,000, at least 500,000, at least 800,000, at least 1 million, or at least 2 million activation scores, one for each test compound.

In some embodiments, the plurality of compounds includes no more than 10 million, no more than 5 million, no more than 1 million, no more than 500,000, no more than 100,000, no more than 50,000, no more than 10,000, no more than 8000, no more than 5000, no more than 2000, no more than 1000, no more than 800, no more than 500, no more than 200, or no more than 100 test compounds. In some embodiments, the plurality of compounds consists of from 10 to 500, from 100 to 10,000, from 5000 to 200,000, or from 10,000 to 1 million test compounds.

In some embodiments, the plurality of test compounds is between 10 and $1 \times 10^6$ test compounds. In some embodiments, the plurality of test compounds is between 100 and 100,000 test compounds. In some embodiments, the plurality of test compounds is between 1000 and 100,000 test compounds.

Thus, method 300 can be used to obtain activation scores for a large number of test compounds. Application of the first threshold against these activation scores can be used to identify test compounds, from among the many test compounds tested that are associated with a physiological condition of interest. In typical embodiments, a select number of the test compounds have activation scores that indicate that they are associated with the physiological condition of interest whereas the others do not. Analysis of the select number of the test compounds can be used to determine the molecular properties to test compounds that result in association with the physiological condition of interest. For instance, the chemical structures of the select number of the test compounds that have activation scores that indicate that they are associated with the physiological condition of interest can be visually inspected for similarities in their structure that differentiate them from test compounds that do not associate with the physiological condition of interest. Such molecular properties can then be incorporated into new test molecules that were not included in the original test molecules evaluated by the model 601, and that were not used to train the model 601.

Moreover, more formal approaches can be used to analyze the test compounds (both that do and do not satisfy the first threshold imposed by method 300). For instance, substructure mining can be used to identify the sub-structures within the test compounds that cause such compounds to associate with the physiological condition of interest. Examples of substructure mining include, but are not limited to MOSS (Borgetl and Meinl, 2006, "Full Perfect Extension Pruning for Frequent Graph Mining," Proc. Workshop on Mining Complex Data (MCD 2006 at ICDM 2006, Hong Kong, China, IEEE Press, Piscataway, NJ, USA, which is hereby incorporated by reference, and MOFA (Meinl and Worlein, 2006 "Mining Molecular Datasets on Symmetric Processor Systems," International conference on Systems, man and Cybernetics 2, pp. 1269-1274, which is hereby incorporated by reference).

Also, maximum common substructure (MCS) analysis can be used to identify the sub-structures within the test compounds that cause such compounds to associate with the physiological condition of interest. Examples of MCS analysis include, but are not limited to LIBMCS (Chemaxon, Library MCS, 2008), MCSS (OEChem TK version 2.0.0, OpenEye Scientific Software, Santa Fe, NM http://www.eyesopen.com), and CncMCS (http://www.chemnavigator.com/cnc/products/downloads.asp).

Also, SMARTS can be used to identify the sub-structures within the test compounds that cause such compounds to associate with the physiological condition of interest. An Example of SMART analysis is the CDK Descriptor GUI.

Also Frequent Subgraph Mining can be used to identify the sub-structures within the test compounds that cause such compounds to associate with the physiological condition of interest. An example of Frequent Subgraph Mining is Par-Mol (Uni Erlangen).

Also graph and chemical mining can be used to identify the sub-structures within the test compounds that cause such compounds to associate with the physiological condition of interest. An example of graph and chemical mining is PAFI/AFGen (Karypis Lab UMN).

Perturbation Signatures.

As described above, in some embodiments, the physiological condition of interest is a perturbation signature (e.g., characterized by a discrepancy between a first cell state and a second cell state in response to a perturbation). Accordingly, another aspect of the present disclosure provides a method 700 of associating a test chemical compound with a physiological condition of interest. In some embodiments, the physiological condition of interest is a disease.

Referring to Block 702, the method includes obtaining a fingerprint of a chemical structure of the test chemical compound. Any suitable embodiments of physiological conditions, compounds, fingerprints, and/or methods of obtaining fingerprints, as disclosed in the above sections entitled "Physiological conditions" and "Compounds," are contemplated, including any substitutions, modifications, additions, deletions, and/or combinations thereof, as will be apparent to one skilled in the art.

For instance, in some embodiments, the test chemical compound is an organic compound having a molecular weight of less than 2000 Daltons. In some embodiments, the test chemical compound is an organic compound that satisfies each of the Lipinski rule of five criteria. In some embodiments, the test chemical compound is an organic compound that satisfies at least three criteria of the Lipinski rule of five criteria. In some embodiments, method further comprising calculating the fingerprint from a simplified molecular-input line-entry system (SMILES) string representation of the test chemical compound. In some embodiments, the fingerprint is generated from the chemical structure using SMILES Transformer, ECFP4, RNNS2S, or GraphConv.

Referring to Block 704, the method further includes inputting the fingerprint into a model, where the model comprises 100 or more parameters, the model outputs one or more calculated activation scores responsive to the inputting of the fingerprint into the model, and each respective calculated activation score in the one or more calculated activation scores represents a corresponding perturbation signature in a set of perturbation signatures.

Any suitable embodiments of models, such as those as disclosed in the above section entitled "Model architectures," are contemplated, and any substitutions, modifications, additions, deletions, and/or combinations thereof, as will be apparent to one skilled in the art. For instance, in some embodiments, the model comprises a neural network. In some such embodiments, the neural network is a fully connected neural network with ReLU activation. In some embodiments, the neural network is a message passing neural network.

In some embodiments, the model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the model is an ensemble model of a plurality of component models, and each calculated activation score in the one or more calculated activation scores is measure of central tendency of an output of each component model in the plurality of component models.

In some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the plurality of component models comprises a plurality of neural networks. In some such embodiments, a first neural network in the plurality of neural networks is a fully connected neural network with ReLU activation, and a second neural network in the plurality of neural networks is a message passing neural network.

As defined above, a perturbation refers to any exposure of the cell to one or more conditions, such as a treatment by one or more compounds. In some embodiments, a perturbation signature is a change in the expression or abundance level of one or more cellular constituents in the cell induced by a perturbation.

Example perturbations include, but are not limited to, gene knockdowns, cellular responses to stimuli, tissue growth and regeneration, and/or treatment with or exposure to compounds. Example perturbagens include, but are not limited to, a small molecule, a biologic, a therapeutic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other gene editing system), or any combination of any of the foregoing.

In some embodiments, perturbations are characterized at the systems level (e.g., binding or docking activity) and/or with respect to downstream effects and organ-level phenotypes. In some embodiments, perturbations are characterized as a function of the mechanisms driving or underlying the responses to perturbagens at the molecular, cellular, and/or tissue level (e.g., by identifying or measuring biomarkers, cell viability, and/or drug-protein interactions before or after perturbation). For instance, measurements of perturbations can include phenotypic measurements (e.g., IC50 values) and/or cellular constituent signatures (e.g., omics profiling).

In some embodiments, a respective perturbation and/or a corresponding perturbation signature is obtained from a publicly available database, such as the Genomics of Drug Sensitivity in Cancer, the Cancer Therapeutics Response Portal, the Connectivity Map, PharmacoDB, Base of Bio-isosterically Exchangeable Replacements (BoBER), DrugBank, the Human Cell Atlas, the Molecular Signatures Database (MSigDB), and/or Enrichr. Other suitable databases from which perturbation data can be obtained include NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

Methods of obtaining perturbation data include measurements of cellular constituent data using, for example, perturb-seq, CRISP-seq, CROP-seq, CRISPRi, TAP-seq, CRIS-PRa, perturb-CITE-seq, sci-Plex, multiplexed, MIX-seq, CyTOF, and/or scRNA-seq. Methods of obtaining perturbation data further include any method of obtaining omics data, including mass spectrometry (e.g., LCMS, GCMS), flow cytometry, quantitative polymerase chain reaction (qPCR), gel electrophoresis, gene-chip analysis, microarray, cytofluorimetric analysis, fluorescence microscopy, confocal laser scanning microscopy, laser scanning cytometry, affinity chromatography, manual batch mode separation, electric field suspension, sequencing, and/or any combination thereof. In some embodiments, any of the methods for obtaining cellular constituent abundance values disclosed herein are contemplated for use in obtaining perturbation data (e.g., for perturbation signatures).

In some embodiments, the set of perturbation signatures consists of the first perturbation signature. In some embodiments, the set of perturbation signature comprises five or more perturbation signatures. In some embodiments, the set of perturbation signatures comprises ten or more perturbation signatures. In some embodiments, the set of perturbation signature comprises 100 or more perturbation signatures.

In some embodiments, the set of perturbation signatures comprises at least 2, at least 3, at least 4, at least 5, at least 10, at least 15, at least 20, at least 30, at least 40, at least 50, at least 60, at least 70, at least 80, at least 90, at least 100, at least 200, at least 300, at least 400, at least 500, at least 800, at least 1000, at least 2000, or at least 5000 perturbation signatures. In some embodiments, the set of perturbation signatures comprises no more than 10,000, no more than 5000, no more than 1000, no more than 800, no more than 500, no more than 200, no more than 100, no more than 50, or no more than 20 perturbation signatures. In some embodiments, the set of perturbation signatures comprises from 5 to 50, from 2 to 100, from 20 to 500, from 10 to 1000, from 800 to 5000, or from 50 to 2000 perturbation signatures. In some embodiments, the set of perturbation signatures falls within another range starting no lower than 2 perturbation signatures and ending no higher than 10,000 perturbation signatures.

Referring to Block 706, each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound.

In some embodiments, the perturbed state of a respective perturbation signature in the plurality of perturbation signature is represented by control cells that have not been exposed to a compound in the plurality of compounds. In some embodiments, the perturbed state of a respective perturbation signature in the plurality of perturbation signature is represented by an average across unrelated perturbed cells that have been exposed to chemical compounds in the plurality of chemical compounds other than the compound associated with the respective perturbation signature.

In some embodiments, a change in cell state refers to a change between an unaltered cell state and an altered cell state, where the altered cell state occurs through the cellular transition from the unaltered cell state to the altered cell state. Moreover, at least one of (i) the unaltered cell state, (ii) the altered cell state, and (iii) the transition from the unaltered cell state to the altered cell state is associated with the physiological condition of interest.

In some embodiments, a respective perturbation signature in the set of perturbation signatures can be determined, as a non-limiting example, using any of the methods disclosed in U.S. patent application Ser. No. 16/511,691 entitled "Methods of Analyzing Cells," filed Jul. 15, 2019, which is hereby incorporated by reference.

In certain embodiments, covariates of a perturbation (e.g., exposure of cells to a particular chemical composition) may exist. For example, covariates of a chemical composition may include: a specific dose of the chemical composition, a time at which the cells exposed to the chemical composition is measured to quantify cellular constituents, and/or the identity (e.g., cell line) of the cells exposed to the chemical composition. In some embodiments, a perturbation (e.g., exposure of cells to a particular chemical composition) is predicted to affect a particular cellular transition only when a threshold quantity of its covariates is also predicted to affect the particular cellular transition. In other words, in some embodiments, the calculated activation score of a particular perturbation signature is determined at least in part by whether the covariates of the chemical composition of the particular perturbation signature are also predicted to affect the particular cellular transition associated with the physiological condition of interest.

Generally, as described above, the output of a trained model is defined through a process of learning on a training dataset including labels (e.g., numerical activation scores) and adjusting a plurality of parameters until the output of the trained model satisfies a minimum level of performance, such as through a validation step. Training models is further disclosed below in the section entitled, "Model training." Thus, in some such embodiments, the trained model provides, as output, the calculated activation score for a first perturbation signature that indicates an association of the test chemical compound with the physiological condition of interest (e.g., where the first perturbation signature is associated with a cell state transition associated with the physiological condition of interest).

Referring then to Block 708, the method includes identifying the chemical compound with the physiological condition of interest when the respective calculated activation score for a first perturbation signature in the set of perturbation signatures satisfies a first threshold criterion.

Any suitable embodiments of activation scores, as disclosed in the above section entitled "Activation scores," are contemplated for the obtaining one or more calculated activation scores, where each activation score represents a corresponding perturbation signature in a set of perturbation signatures, including any substitutions, modifications, additions, deletions, and/or combinations thereof, as will be apparent to one skilled in the art.

In general, what is sought is a chemical compound that identifies (as demonstrated by having a calculated activation score satisfying the first threshold criterion) with the physiological condition of interest. For instance, in some embodiments, satisfaction of the first threshold requires an activation score above a first predetermined numerical value.

For instance, in some embodiments the activation score is expressed as a normalized value on a continuous scale between "0" and "1" (or some other range "A" to "B" where A and B are two different numbers), where values closer to "1" (e.g., 0.89, 0.90, 0.91, 0.92, etc.) indicate a strong association between a perturbation signature (and the chemical compound the perturbation signature represents) and the physiological condition of interest. Values closer to "0" (e.g., 0.01, 0.02, 0.03, 0.04, etc.) indicate no association between the perturbation signature (and the chemical compound the perturbation signature represents) and the physiological condition of interest. In such instances, a first threshold is chosen between "0" and "1" (or some other range "A" to "B" where A and B are two different numbers) and the perturbation signature (and the chemical structures it represents) is deemed to be associated with the physiological condition of interest when the activation score is above the first threshold whereas the perturbation signature (and the chemical structures it represents) is deemed to not be associated with the physiological condition of interest when the activation score is below the first threshold. In some such embodiments, the activation score is expressed as a normalized value on a continuous scale between "0" and "1" (or some other range "A" to "B" where A and B are two different numbers) and the first threshold is a value between 0 and 1, between 0.10 and 0.90, between 0.20 and 0.80, between 0.30 and 0.70, between 0.50 and 0.99, between 0.60 and 0.99, between 0.70 and 0.99, between 0.80 and 0.99, or between 0.90 and 0.99.

As another example, in some embodiments the activation score is expressed as a normalized value on a continuous scale between "0" and "1" (or some other range "A" to "B" where A and B are two different numbers), where values closer to "1" (e.g., 0.89, 0.90, 0.91, 0.92, etc.) indicate no association between a perturbation signature (and the chemical compound the perturbation signature represents) and the physiological condition of interest. Values closer to "0" (e.g., 0.01, 0.02, 0.03, 0.04, etc.) indicate association between the perturbation signature (and the chemical compound the perturbation signature represents) and the physiological condition of interest. In such instances, a first threshold is chosen between "0" and "1" (or some other range "A" to "B" where A and B are two different numbers) and the perturbation signature (and the chemical structures it represents) is deemed to be associated with the physiological condition of interest when the activation score is below the first threshold whereas the perturbation signature (and the chemical structures it represents) is deemed to not be associated with the physiological condition of interest when the activation score is above the first threshold. In some such embodiments, the activation score is expressed as a normalized value on a continuous scale between "0" and "1" (or some other range "A" to "B" where A and B are two different numbers) and the first threshold is a value between 0 and 1, between 0.10 and 0.90, between 0.20 and 0.80, between 0.30 and 0.70, between 0.50 and 0.99, between 0.60 and 0.99, between 0.70 and 0.99, between 0.80 and 0.99, or between 0.90 and 0.99.

In some embodiments, the first threshold criterion is a requirement that the first perturbation signature have a threshold activation score.

In some embodiments, the first threshold criterion is a requirement that the first perturbation signature have at least a threshold rank, in the set of perturbation signatures, where the set of perturbation signatures is ranked based on a comparison of each perturbation signature in the set of perturbation signatures to a reference signature (e.g., a single-cell transition signature). Methods of comparison of perturbation signatures to a reference signatures (e.g., a single-cell transition signature) suitable for use in associating chemical compounds with physiological conditions are described in further detail below in the section entitled, "Numerical activation scores for perturbation signatures."

In some embodiments, the identifying requires that the respective calculated activation score of each perturbation signature in the set of perturbation signatures satisfy the threshold criterion. In some embodiments, the identifying requires that a measure of central tendency across the respective calculated activation score of each perturbation signature in the set of perturbation signatures satisfy the threshold criterion. In some embodiments, the measure of central tendency is an arithmetic mean, a weighted mean, a midrange, a midhinge, a trimean, a Winsorized mean, a mean, or a mode of each respective calculated activation score of each perturbation signature in the set of perturbation signatures.

In some embodiments, the set of perturbation signatures is between two and 100 perturbation signatures and the identifying requires that the respective calculated activation score of each perturbation signature in the set of perturbation signature satisfy the threshold criterion. In some embodiments, the set of perturbation signatures is between two and 100 perturbation signatures and the identifying requires a measure of central tendency across the respective calculated activation score of each perturbation signature in the set of perturbation signatures satisfy the threshold criterion. In some embodiments, the measure of central tendency is an arithmetic mean, a weighted mean, a midrange, a midhinge, a trimean, a Winsorized mean, a mean, or a mode of each respective calculated activation score of each perturbation signature in the set of perturbation signatures.

In some embodiments, the set of perturbation signatures is a plurality of perturbation signatures, a first subset of the plurality of perturbation signatures, including the first perturbation signature, is associated with the physiological condition of interest, a second subset of the plurality of perturbation signatures is not associated with the physiological condition of interest, and the test chemical compound is identified with the physiological condition of interest when the respective calculated activation score for the first perturbation signature satisfies the first threshold criterion and the respective calculated activation score for a perturbation signature in the second subset of the plurality of perturbation signatures satisfies a second threshold criterion.

In some embodiments, the second threshold criterion is a requirement that the respective calculated activation score for a perturbation signature in the second subset of the plurality of perturbation signatures have a threshold activation score.

In some embodiments, the second threshold criterion is a requirement that the respective calculated activation score for a perturbation signature in the second subset of the plurality of perturbation signatures have at least a threshold rank, in the set of perturbation signatures, where the set of perturbation signatures is ranked based on a comparison of each perturbation signature in the set of perturbation signatures to a reference signature (e.g., a single-cell transition signature).

In some embodiments, the identifying requires that the respective calculated activation score of each perturbation signature in the second subset of perturbation signatures satisfy the second threshold criterion. In some embodiments, the identifying requires that a measure of central tendency across the respective calculated activation score of each perturbation signature in the second subset of perturbation signatures satisfy the second threshold criterion. In some embodiments, the measure of central tendency is an arithmetic mean, a weighted mean, a midrange, a midhinge, a trimean, a Winsorized mean, a mean, or a mode of each respective calculated activation score of each perturbation signature in the set of perturbation signatures.

III. METHODS OF ASSOCIATING CHEMICAL COMPOUNDS WITH A PHYSIOLOGICAL CONDITION OF INTEREST

Model Training.

Another aspect of the present disclosure provides a method 800 of associating chemical compounds with a physiological condition of interest. In some embodiments, the physiological condition of interest is a disease.

Referring to Block 802, the method includes obtaining, in electronic form, a respective fingerprint of a chemical structure of each compound in a plurality of compounds, thereby obtaining a plurality of fingerprints. Any suitable embodiments of physiological conditions, compounds, fingerprints, and/or methods of obtaining fingerprints, as disclosed in the above sections entitled "Physiological conditions" and "Compounds," are contemplated, including any substitutions, modifications, additions, deletions, and/or combinations thereof, as will be apparent to one skilled in the art.

For instance, in some embodiments, the plurality of compounds is between 10 and $1 \times 10^6$ compounds. In some embodiments, the plurality of compounds is between 100 and 100,000 compounds. In some embodiments, the plurality of compounds is between 1000 and 100,000 compounds.

In some embodiments, each chemical compound in the plurality of chemical compounds is an organic compound having a molecular weight of less than 2000 Daltons. In some embodiments, each chemical compound in the plurality of chemical compounds satisfies each of the Lipinski rule of five criteria. In some embodiments, each chemical compound in the plurality of chemical compounds satisfies at least three criteria of the Lipinski rule of five criteria. In some embodiments, each respective fingerprint is generated from the chemical structure using SMILES Transformer, ECFP4, RNNS2S, or GraphConv.

Referring to Block 804, the method includes obtaining, in electronic form, a respective numerical activation score of each cellular constituent module in a set of cellular constituent modules for each compound in the plurality of compounds, where each respective cellular constituent module in the set of cellular constituent modules includes an independent subset of a plurality of cellular constituents. Any suitable embodiments of cellular constituents, cellular constituent modules, and/or methods of identifying cellular constituent modules, as disclosed in the sections entitled, "Cellular constituents and cellular constituent modules," above, and "Identifying cellular constituent modules," below, are contemplated, including any substitutions, modifications, additions, deletions, and/or combinations thereof, as will be apparent to one skilled in the art.

For instance, in some embodiments, the set of cellular constituent modules is a single cellular constituent module. In some embodiments, the set of cellular constituent modules is a plurality of cellular constituent modules. In some embodiments, the set of cellular constituent modules is between two and five hundred cellular constituent modules. In some embodiments, the set of cellular constituent modules consists of a single cellular constituent module. In some embodiments, the set of cellular constituent modules comprises five or more cellular constituent modules. In some embodiments, the set of cellular constituent modules comprises ten or more cellular constituent modules. In some embodiments, the set of cellular constituent modules comprises 100 or more cellular constituent modules. In some embodiments, the set of cellular constituent modules is a plurality of cellular constituent modules, a first subset of the plurality of cellular constituent modules is associated with the physiological condition of interest, and a second subset of the plurality of cellular constituent modules is not associated with the physiological condition of interest.

Figure 2B:
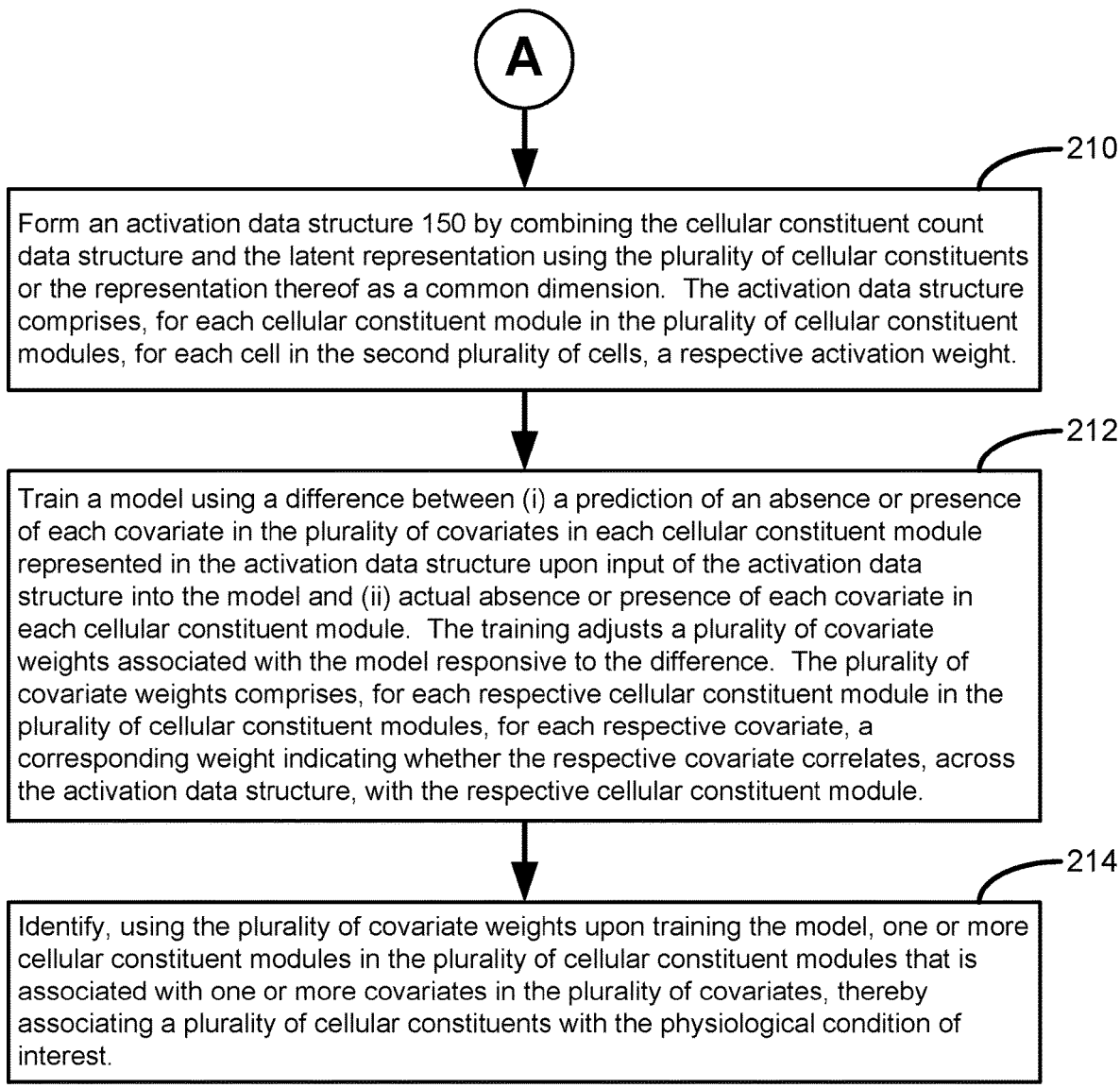

In some embodiments, as illustrated by the example workflow in FIGS. 2A-B, the method further comprises identifying a cellular constituent module in the plurality of cellular constituent modules by a process comprising obtaining one or more first datasets in electronic form, the one or more first datasets comprising or collectively comprising, for each respective cell in a first plurality of cells, where the first plurality of cells comprises twenty or more cells and collectively represents a plurality of annotated cell states, for each respective cellular constituent in the plurality of cellular constituents, where the plurality of cellular constituents comprises 10 or more cellular constituents, a corresponding abundance of the respective cellular constituent in the respective cell. The method thus accesses or forms a plurality of vectors, each respective vector in the plurality of vectors (i) corresponding to a respective cellular constituent in the plurality of constituents and (ii) comprising a corresponding plurality of elements, each respective element in the corresponding plurality of elements having a corresponding count representing the corresponding abundance of the respective cellular constituent in the respective cell in the first plurality of cells. The plurality of vectors is used to identify each candidate cellular constituent module in a plurality of candidate cellular constituent modules. Each candidate cellular constituent module in the plurality of candidate cellular constituent modules includes a subset of the plurality of cellular constituents, where the plurality of cellular constituent modules are arranged in a latent representation dimensioned by (i) the plurality of candidate cellular constituent modules and (ii) the plurality of cellular constituents or a representation thereof, and where the plurality of cellular constituent modules comprises more than ten cellular constituent modules.

One or more second datasets are obtained in electronic form, the one or more second datasets comprising or collectively comprising, for each respective cell in a second plurality of cells, where the second plurality of cells comprises twenty or more cells and collectively represents a plurality of covariates informative of the physiological condition of interest, for each respective cellular constituent in the plurality of cellular constituents, a corresponding abundance of the respective cellular constituent in the respective cell. Thus, a cellular constituent count data structure dimensioned by (i) the second plurality of cells and (ii) the plurality of cellular constituents or the representation thereof is obtained. An activation data structure is formed by combining the cellular constituent count data structure and the latent representation using the plurality of cellular constituents or the representation thereof as a common dimension, where the activation data structure comprises, for each cellular constituent module in the plurality of cellular constituent modules, for each cell in the second plurality of cells, a respective activation weight.

A candidate cellular constituent model is trained using a difference between (i) a prediction of an absence or presence of each covariate in the plurality of covariates in each cellular constituent module represented in the activation data structure upon input of the activation data structure into the candidate model and (ii) actual absence or presence of each covariate in each cellular constituent module, where the training adjusts a plurality of covariate weights associated with the candidate cellular constituent model responsive to the difference, and where the plurality of covariate weights comprises, for each respective cellular constituent module in the plurality of cellular constituent modules, for each respective covariate, a corresponding weight indicating whether the respective covariate correlates, across the activation data structure, with the respective cellular constituent module. Upon training the candidate cellular constituent model, the plurality of covariate weights is used to identify the cellular constituent module in the plurality of candidate cellular constituent modules (e.g., that associates with the physiological condition of interest).

In some embodiments, the physiological condition of interest is a disease, and the first plurality of cells includes cells that are representative of the disease and cells that are not representative of the disease as documented by the plurality of annotated cell states. In some embodiments, an annotated cell state in the plurality of annotated cell states is an exposure of a cell in the first plurality of cells to a compound under an exposure condition. In some embodiments, the exposure condition is a duration of exposure, a concentration of the compound, or a combination of a duration of exposure and a concentration of the compound.

In some embodiments, each cellular constituent in the plurality of cellular constituents is a particular gene, a particular mRNA associated with a gene, a carbohydrate, a lipid, an epigenetic feature, a metabolite, a protein, or a combination thereof. In some embodiments, the corresponding abundance of the respective cellular constituent in the respective cell in the first or second plurality of cells is determined by a colorimetric measurement, a fluorescence measurement, a luminescence measurement, or a resonance energy transfer (FRET) measurement. In some embodiments, the corresponding abundance of the respective cellular constituent in the respective cell in the first or second plurality of cells is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combination thereof. In some embodiments, the plurality of cellular constituents consists of between 100 and 8,000 cellular constituents.

In some embodiments, the using the plurality of vectors to identify each candidate cellular constituent module in the plurality of candidate cellular constituent modules comprises application of a correlation model to the plurality of vectors using each corresponding plurality of elements of each vector in the plurality of vectors. In some embodiments, the correlation model includes graph clustering. In some embodiments, the graph clustering method is Leiden clustering on a Pearson correlation-based distance metric or is Louvain clustering.

In some embodiments, the plurality of cellular constituent modules consists of between 10 and 2000 cellular constituent modules. In some embodiments, each candidate cellular constituent module in the plurality of constituent modules consists of between two and three hundred cellular constituents.

In some embodiments, the plurality of covariates comprises cell batch, cell donor, cell type, disease status, or exposure to a chemical compound.

In some embodiments, the training the candidate cellular constituent model is performed using a categorical cross-entropy loss in a multi-task formulation, in which each covariate in the plurality of covariates corresponds to a cost function in plurality of cost functions and each respective cost function in the plurality of cost functions has a common weighting factor.

Referring to Block 806, the method further includes training an untrained model using, for each respective chemical structure of each respective compound in the plurality of compounds, for each respective cellular constituent module in the set of cellular constituent modules, a respective difference between (i) a respective calculated activation score for the respective cellular constituent module upon input of the fingerprint of the chemical structure of the respective compound into the untrained model and (ii) the respective numerical activation score of the respective cellular constituent module for the respective compound in the set of cellular constituent modules.

In some embodiments, an activation score in the one or more calculated activation scores is a respective activation weight for a respective cellular constituent module corresponding to a respective compound. For instance, in some embodiments, an activation score is an activation weight obtained as described in FIGS. 2A-B and illustrated in the activation data structure in FIG. 5, where the activation score indicates the activation (e.g., inducement and/or differential expression) of the respective (e.g., first) cellular constituent module, correlating to and/or in response to treatment with the respective compound.

Any suitable embodiments of models, such as those disclosed in the above section entitled "Model architectures," are contemplated, and any substitutions, modifications, additions, deletions, and/or combinations thereof, as will be apparent to one skilled in the art. For instance, in some embodiments, the trained model comprises a neural network. In some embodiments, the neural network is a fully connected neural network with ReLU activation. In some embodiments, the neural network is a message passing neural network. In some embodiments, the trained model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the trained model is an ensemble model of a plurality of component models, and the respective calculated activation score is a measure of central tendency of an output of each component model in the plurality of component models. In some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model. In some embodiments, the plurality of component models comprises a plurality of neural networks. In some embodiments, a first neural network in the plurality of neural networks is a fully connected neural network with ReLU activation, and a second neural network in the plurality of neural networks is a message passing neural network.

Referring to Block 808, the training adjusts a plurality of parameters associated with the untrained model responsive to the difference, where the plurality of parameters comprises 100 or more parameters, thereby obtaining a trained model that associates chemical compounds with the physiological condition of interest.

In some embodiments, input to the model includes a plurality of activation scores, each respective activation score corresponding to a respective cellular constituent module in a plurality of cellular constituent modules, for each compound in a plurality of compounds. Activation scores corresponding to each respective cellular constituent module for each respective compound serve as labels (e.g., numerical activation scores indicating an actual presence or absence of association between modules and compounds) for training a multi-task model to identify associations (e.g., weights and/or correlations) between modules and compounds. For instance, as described above, in some embodiments, a first subset of the plurality of cellular constituent modules is associated with the physiological condition of interest, and a second subset of the plurality of cellular constituent modules is not associated with the physiological condition of interest. Thus, in some such embodiments, an actual presence of association can be included in the training dataset using the first subset of the plurality of cellular constituent modules as labels, and an actual absence of association can be included in the training dataset using the second subset of the plurality of cellular constituent modules as labels.

In some embodiments, the plurality of compounds includes at least 5, at least 10, at least 15, at least 20, at least 30, at least 40, at least 50, at least 100, at least 200, at least 300, at least 400, at least 500, at least 800, at least 1000, at least 2000, at least 3000, at least 4000, at least 5000, at least 8000, at least 10,000, at least 20,000, at least 30,000, at least 50,000, at least 80,000, at least 100,000, at least 200,000, at least 500,000, at least 800,000, at least 1 million, or at least 2 million compounds, where for each compound in the plurality of compounds, the input to the model includes a respective activation score, for each respective cellular constituent module in a plurality of cellular constituent modules.

In some embodiments, the plurality of compounds includes no more than 10 million, no more than 5 million, no more than 1 million, no more than 500,000, no more than 100,000, no more than 50,000, no more than 10,000, no more than 8000, no more than 5000, no more than 2000, no more than 1000, no more than 800, no more than 500, no more than 200, or no more than 100 compounds, where for each compound in the plurality of compounds, the input to the model includes a respective activation score, for each respective cellular constituent module in a plurality of cellular constituent modules. In some embodiments, the plurality of compounds consists of from 10 to 500, from 100 to 10,000, from 5000 to 200,000, or from 10,000 to 1 million compounds, where for each compound in the plurality of compounds, the input to the model includes a respective activation score, for each respective cellular constituent module in a plurality of cellular constituent modules.

Figure 5:
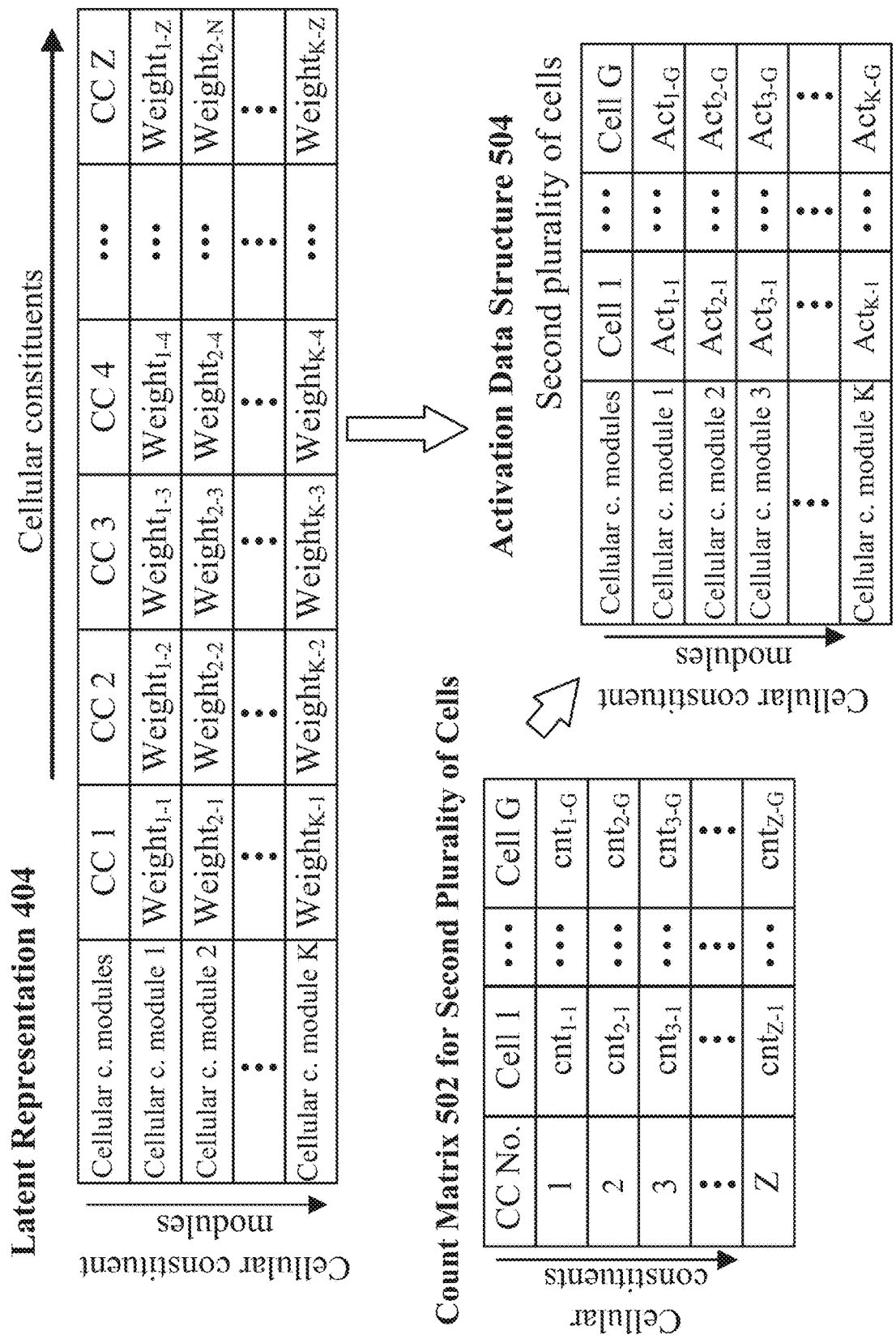
FIG. 5 illustrates an example of a cellular constituent count data structure and an example activation data structure, in accordance with some embodiments of the present disclosure.
Figure 7:
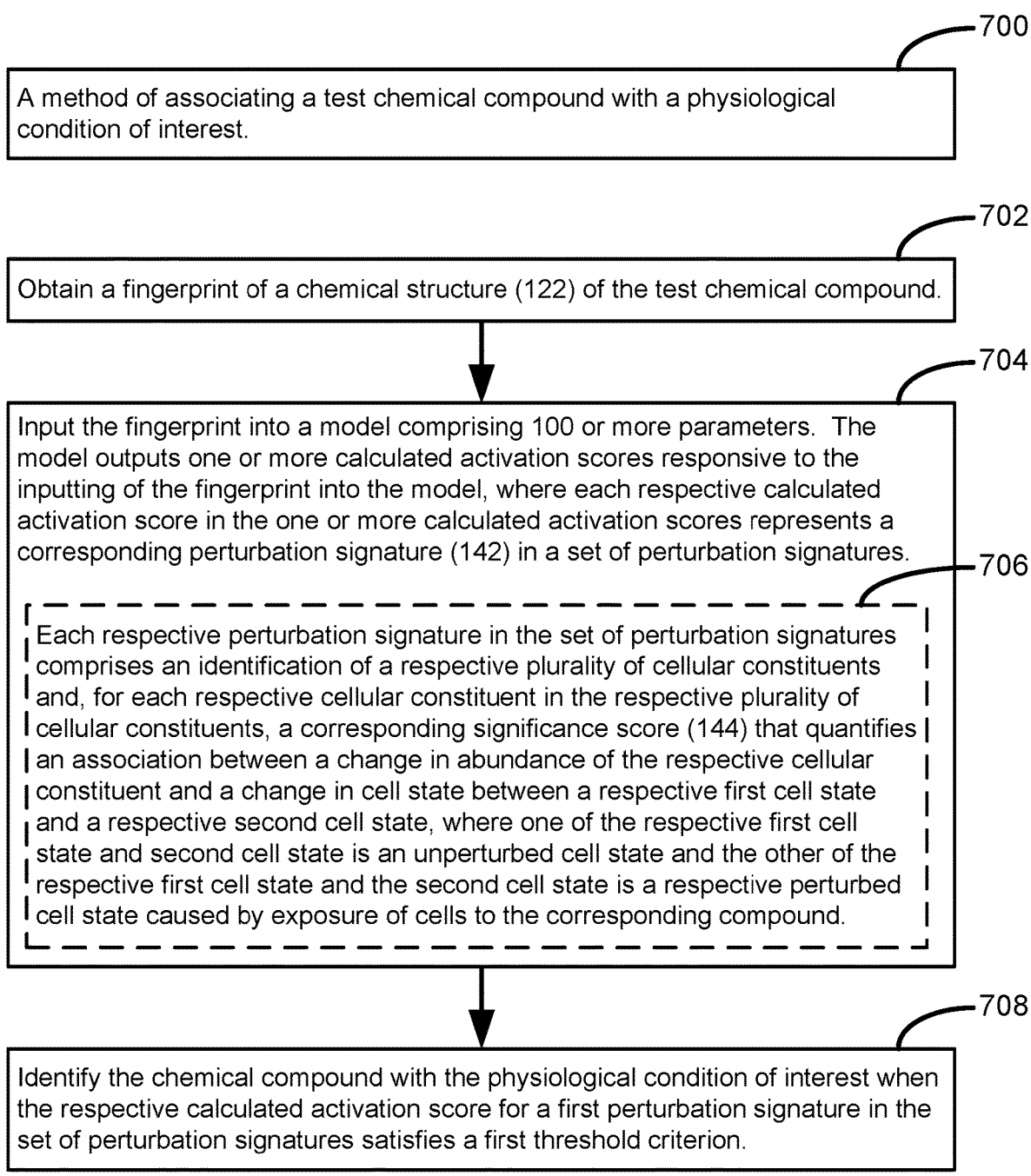
FIG. 7 provides a flow chart of processes and features of an example method for associating a test chemical compound with a physiological condition of interest, in which dashed boxes represent optional elements, in accordance with some embodiments of the present disclosure.
Figure 8:
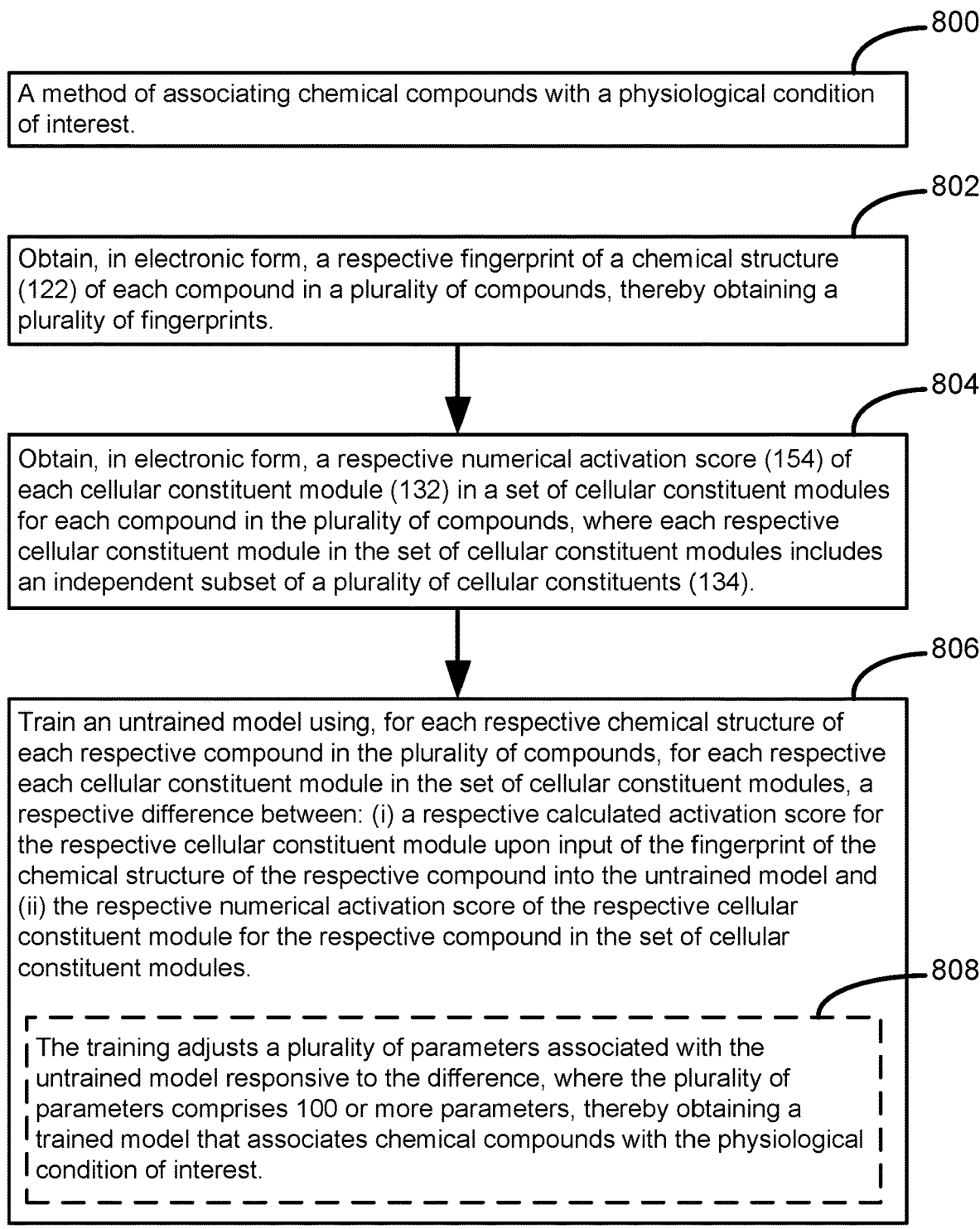
FIG. 8 provides a flow chart of processes and features of an example method for associating chemical compounds with a physiological condition of interest, in which dashed boxes represent optional elements, in accordance with an embodiment of the present disclosure.
Figure 9:
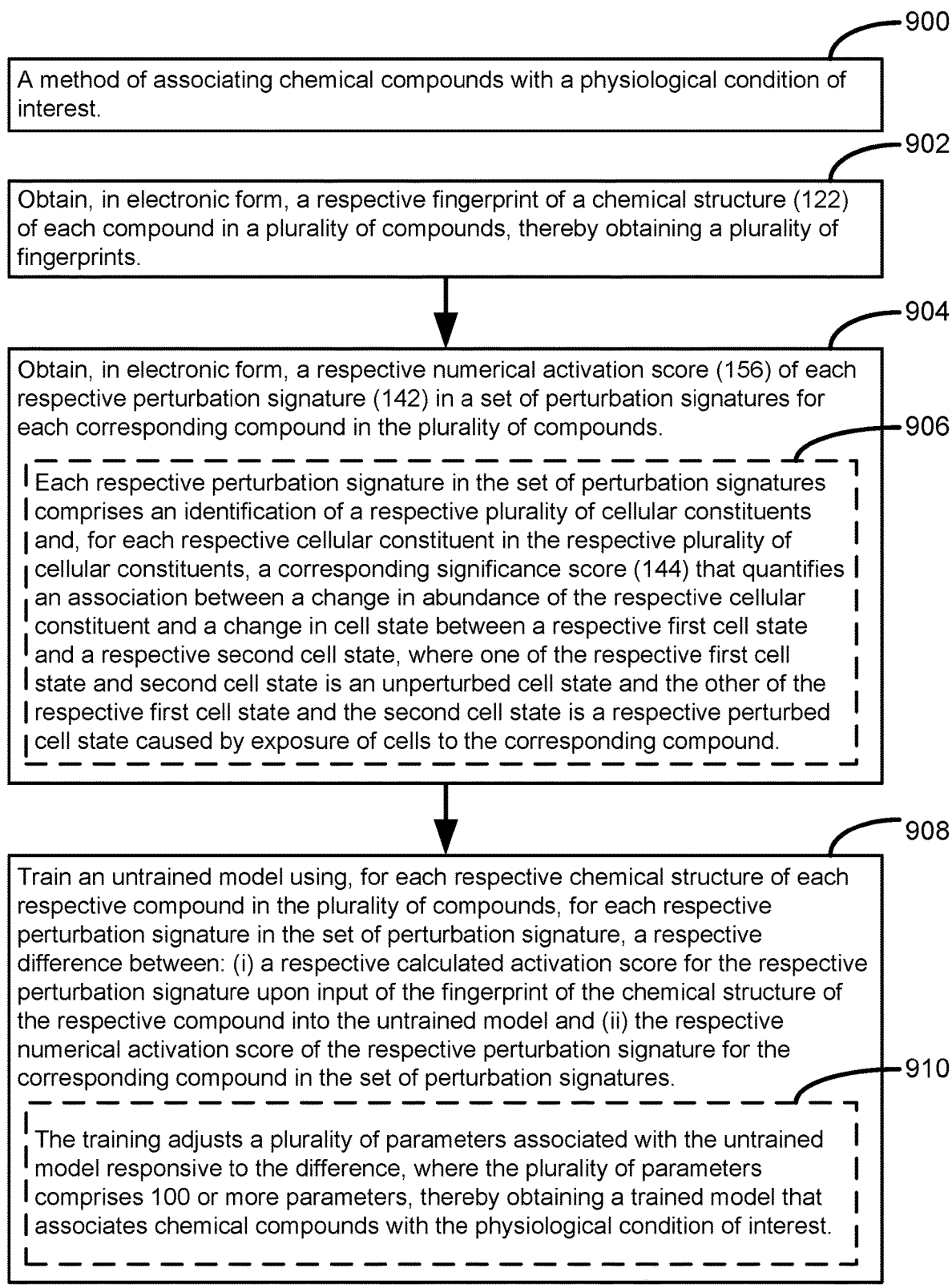
FIG. 9 provides a flow chart of processes and features of an example method for associating chemical compounds with a physiological condition of interest, in which dashed boxes represent optional elements, in accordance with an embodiment of the present disclosure.

In some embodiments, as described above, a respective numerical activation score in the plurality of numerical activation scores is an activation weight, for each respective cellular constituent module in a plurality of cellular constituent modules, for each compound in a plurality of compounds (illustrated, for example, in the activation data structure in FIG. 5).

As described above, in some embodiments, an output of the model includes one or more calculated activation scores indicating whether a respective compound (e.g., a test chemical compound) in a plurality of compounds correlates with a respective one or more cellular constituent module in a plurality of cellular constituent modules.

Generally, training a model (e.g., a neural network) comprises updating the plurality of parameters (e.g., weights) for the respective model through backpropagation (e.g., gradient descent). First, a forward propagation is performed, in which input data (e.g., a plurality of activation scores for each respective compound in a plurality of compounds, for each respective cellular constituent module in a plurality of modules) is accepted into the neural network, and an output is calculated based on the selected activation function and an initial set of parameters (e.g., weights and/or hyperparameters). In some embodiments, parameters (e.g., weights and/or hyperparameters) are randomly assigned (e.g., initialized) for an untrained or partially trained model. In some embodiments, parameters are transferred from a previously saved plurality of parameters or from a pre-trained model (e.g., by transfer learning).

A backward pass is then performed by calculating an error gradient for each respective parameter corresponding to each respective unit in each layer, where the error for each parameter is determined by calculating a loss (e.g., error) based on the network output (e.g., the predicted absence or presence of association between a respective compound and a respective cellular constituent module as a calculated activation score) and the input data (e.g., the expected value or true labels; the actual absence or presence of association between a respective compound and a respective cellular constituent module as a numerical activation score). Parameters (e.g., weights) are then updated by adjusting the value based on the calculated loss, thereby training the model.

For example, in some general embodiments of machine learning, backpropagation is a method of training a network with hidden layers comprising a plurality of weights (e.g., embeddings). The output of an untrained model (e.g., the predicted absence or presence of association as a calculated activation score) is first generated using a set of arbitrarily selected initial weights. The output is then compared with the original input (e.g., the actual absence or presence of association as a numerical activation score) by evaluating an error function to compute an error (e.g., using a loss function). The weights are then updated such that the error is minimized (e.g., according to the loss function). In some embodiments, any one of a variety of backpropagation algorithms and/or methods are used to update the plurality of weights, as will be apparent to one skilled in the art.

In some embodiments, the loss function is mean square error, quadratic loss, mean absolute error, mean bias error, hinge, multi-class support vector machine, and/or cross-entropy. In some embodiments, training an untrained or partially trained model comprises computing an error in accordance with a gradient descent algorithm and/or a minimization function. In some embodiments, training an untrained or partially trained model comprises computing a plurality of errors using a plurality of loss functions. In some embodiments, each loss function in a plurality of loss functions receives a same or a different weighting factor.

FIG. 6 illustrates an example of a method for training a model, in accordance with some embodiments of the present disclosure. The activation data structure (top panel) provides input to the model, including a plurality of activation scores indicating associations between each respective cellular constituent module in the plurality of K cellular constituent modules and each cell in a plurality of G cells, where each cell represents a respective compound in a plurality of compounds. For each respective cellular constituent module in the plurality of cellular constituent modules (middle panel), a corresponding weight is initialized (e.g., to a random weight), prior to the training, for each respective compound in the plurality of compound collectively represented by the plurality of cells (e.g., W compounds). Thus, the plurality of compound weights comprises a compound weight matrix (middle panel). Adjustment of the plurality of compound weights is performed using the difference between (i) a respective calculated activation score for the respective cellular constituent module upon input of the fingerprint of the chemical structure of the respective compound into the untrained model (e.g., predicted) and (ii) the respective numerical activation score of the respective cellular constituent module for the respective compound in the set of cellular constituent modules (e.g., actual) (bottom panel). In some embodiments, actual activations are obtained, for example, using the method for identifying cellular constituent modules described in the section below entitled, "Identifying Cellular Constituent Modules," with reference to FIGS. 2A-B and 14A-D, where the plurality of covariates comprises a plurality of compounds. Training (e.g., adjustment of compound weights) can then be performed until a trained model is formed (e.g., through completion of a minimum number of adjustments and/or satisfaction of a minimum performance threshold).

In some embodiments, the error function is used to update one or more parameters (e.g., weights) in a model (e.g., a neural network) by adjusting the value of the one or more parameters by an amount proportional to the calculated loss, thereby training the model. In some embodiments, the amount by which the parameters are adjusted is metered by a learning rate hyperparameter that dictates the degree or severity to which parameters are updated (e.g., smaller or larger adjustments). Thus, in some embodiments, the training updates all or a subset of the plurality of parameters based on a learning rate. In some embodiments, the learning rate is a differential learning rate.

In some embodiments, training a model (e.g., a neural network) further uses a regularization on the corresponding parameter of each hidden neuron in the corresponding plurality of hidden neurons. For example, in some embodiments, a regularization is performed by adding a penalty to the loss function, where the penalty is proportional to the values of the parameters in the neural network. Generally, regularization reduces the complexity of the model by adding a penalty to one or more parameters to decrease the importance of the respective hidden neurons associated with those parameters. Such practice can result in a more generalized model and reduce over-fitting of the data. In some embodiments, the regularization includes an L1 or L2 penalty. For example, in some preferred embodiments, the regularization includes an L2 penalty on lower and upper parameters. In some embodiments, the regularization comprises spatial regularization (e.g., determined based on a priori and/or experimental knowledge) or dropout regularization. In some embodiments, the regularization comprises penalties that are independently optimized.

In some embodiments, the training process including the adjusting the plurality of compound weights associated with the model (e.g., responsive to the difference between the predicted and actual labels), is repeated for each training instance in a plurality of training instances.

In some embodiments, the plurality of training instances comprises at least 3, at least 4, at least 5, at least 6, at least 7, at least 8, at least 9, at least 10, at least 50, at least 100, at least 500, at least 1000, at least 2000, at least 3000, at least 4000, at least 5000, or at least 7500 training instances. In some embodiments, the plurality of training instances comprises no more than 10,000, no more than 5000, no more than 1000, no more than 500, no more than 100, or no more than 50 training instances. In some embodiments, the plurality of training instances comprises from 3 to 10, from 5 to 100, from 100 to 5000, or from 1000 to 10,000 training instances. In some embodiments, the plurality of training instances falls within another range starting no lower than 3 training instances and ending no higher than 10,000 training instances.

In some such embodiments, the training includes repeating the adjustment of the parameters of the model (e.g., via backpropagation) over a plurality of training instances, therefore increasing the model's accuracy in indicating whether a respective compound correlates with a respective cellular constituent module.

In some embodiments, the training comprises transfer learning. Transfer learning is further described, for example, in the Definitions section (see, "Untrained models," above).

In some embodiments, training an untrained or partially trained model forms a trained model following a first evaluation of an error function. In some such embodiments, the trained model is formed following a first updating of one or more parameters based on a first evaluation of an error function. In some alternative embodiments, the trained model is formed following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function. In some such embodiments, the trained model is formed following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million updatings of one or more parameters based on the at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function.

In some embodiments, the trained model is formed when the model satisfies a minimum performance requirement. For example, in some embodiments, the trained model is formed when the error calculated for the trained model, following an evaluation of an error function (e.g., a difference between a predicted and an actual association between each compound and each cellular constituent module) satisfies an error threshold. In some embodiments, the error calculated by the error function satisfies an error threshold when the error is less than 20 percent, less than 18 percent, less than 15 percent, less than 10 percent, less than 5 percent, or less than 3 percent.

In an example embodiment, the training the model is performed using a categorical cross-entropy loss in a multi-task formulation, in which each covariate in the plurality of covariates corresponds to a cost function in plurality of cost functions and each respective cost function in the plurality of cost functions has a common weighting factor.

In some embodiments, the training adjusts the plurality of parameters associated with the untrained model responsive to each difference associated with each respective compound for each respective cellular constituent module in the set of cellular constituent modules in accordance with a regression model. In some embodiments, the regression model optimizes a least square error of the each difference associated with each respective compound for each respective cellular constituent module in the set of cellular constituent modules.

While the foregoing discussions of model training describe obtaining and using activation scores indicating associations between compounds and cellular constituent modules, in practice, activation scores indicating associations between compounds and any other physiological condition of interest, or any cellular process thereof, are contemplated for use in training and using a model to associate compounds with physiological conditions. For example, as will be described in the following section, another aspect of the present disclosure comprises training the model using perturbation signatures. Specifically, in some embodiments, the model is trained using numerical activation scores for perturbation signatures as training labels. The trained model is then used, as described in method 700, to obtain, as output, one or more calculated activation scores responsive to the inputting of a chemical structure fingerprint into the model, where each respective calculated activation score in the one or more calculated activation scores represents a corresponding perturbation signature in a set of perturbation signatures.

Obtaining Numerical Activation Scores for Perturbation Signatures.

Accordingly, another aspect of the present disclosure provides a method 900 for associating chemical compounds with a physiological condition of interest. In some embodiments, the physiological condition of interest is a disease.

Referring to Block 902, the method includes obtaining, in electronic form, a respective fingerprint of a chemical structure of each compound in a plurality of compounds, thereby obtaining a plurality of fingerprints. Any suitable embodiments of physiological conditions, compounds, fingerprints, and/or methods of obtaining fingerprints, as disclosed in the above sections entitled "Physiological conditions" and "Compounds," are contemplated, including any substitutions, modifications, additions, deletions, and/or combinations thereof, as will be apparent to one skilled in the art.

For instance, in some embodiments, the plurality of compounds is between 10 and $1 \times 10^6$ compounds. In some embodiments, the plurality of compounds is between 100 and 100,000 compounds. In some embodiments, the plurality of compounds is between 1000 and 100,000 compounds. In some embodiments, each chemical compound in the plurality of chemical compounds is an organic compound having a molecular weight of less than 2000 Daltons. In some embodiments, each chemical compound in the plurality of chemical compounds satisfies each of the Lipinski rule of five criteria. In some embodiments, each chemical compound in the plurality of chemical compounds satisfies at least three criteria of the Lipinski rule of five criteria. In some embodiments, each respective fingerprint is generated from the chemical structure using SMILES Transformer, ECFP4, RNNS2S, or GraphConv.

Referring to Block 904, the method includes obtaining, in electronic form, a respective numerical activation score of each respective perturbation signature in a set of perturbation signatures for each corresponding compound in the plurality of compounds. Any suitable embodiments of perturbation signatures as disclosed in the above section entitled "Perturbation signatures" are contemplated, including any substitutions, modifications, additions, deletions, and/or combinations thereof, as will be apparent to one skilled in the art.

For instance, in some embodiments, the set of perturbation signatures is a single perturbation signature. In some embodiments, the set of perturbation signatures is a plurality of perturbation signatures. In some embodiments, the set of perturbation signatures is between two and five hundred perturbation signatures. In some embodiments, the set of perturbation signatures comprises five or more perturbation signatures. In some embodiments, the set of perturbation signatures comprises ten or more perturbation signatures. In some embodiments, the set of perturbation signatures comprises 100 or more perturbation signatures. In some embodiments, the set of perturbation signatures is a plurality of perturbation signature, a first subset of the plurality of perturbation signatures is associated with the physiological condition of interest, and a second subset of the plurality of perturbation signatures is not associated with the physiological condition of interest.

Referring to Block 906, each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound.

In some embodiments, the respective numerical activation score of a respective perturbation signature in the set of perturbation signatures is obtained by a procedure comprising accessing, in electronic form, a single-cell transition signature representing a measure of differential cellular constituent abundance between an unaltered cell state and an altered cell state. The altered cell state occurs through the cellular transition from the unaltered cell state to the altered cell state, where at least one of (i) the unaltered cell state, (ii) the altered cell state, and (iii) the transition from the unaltered cell state to the altered cell state is associated with the physiological condition of interest. The single-cell transition signature comprises an identification of a reference plurality of cellular constituents and, for each respective cellular constituent in the plurality of reference cellular constituents, a corresponding first significance score that quantifies an association between a change in abundance of the respective cellular constituent and a change in cell state between the unaltered cell state and the altered cell state. The single-cell transition signature and the respective perturbation signature are compared in order to determine the respective numerical activation score of the respective perturbation signature.

In some embodiments, the comparing the single-cell transition signature and the perturbation signature to determine the respective numerical activation score of the respective perturbation signature comprises comparing, for each respective cellular constituent in the reference plurality of cellular constituents of the single-cell transition signature, the first significance score of the respective cellular constituent in the single-cell transition signature to the corresponding significance score of the corresponding cellular constituent in the respective perturbation signature.

In some embodiments, the comparing the single-cell transition signature and the perturbation signature to determine the respective numerical activation score of the respective perturbation signature comprises comparing, for each respective cellular constituent in the reference plurality of cellular constituents of the single-cell transition signature, the significance score of each respective cellular constituent in the plurality of reference cellular constituents in the single-cell transition signature to the corresponding significance score of each corresponding cellular constituent in the plurality of cellular constituents in the respective perturbation signature.

In some embodiments, the activation score of the respective perturbation signature is a relative ranking of a relevance of the respective perturbation signature, relative to other perturbation signatures in the set of perturbations signatures, to the single-cell transition signature. In some embodiments, the relative ranking is determined by a Wilcoxon rank-sum test, a t-test, a logistic regression, or a generalized linear model. In some embodiments, the activation score of the respective perturbation signature are not based upon a ranking.

In some embodiments, the activation score of the respective perturbation signature is a measure of central tendency of the corresponding significance score, for each respective cellular constituent in the respective plurality of cellular constituents for the respective perturbation signature. In some embodiments, the measure of central tendency is an arithmetic mean, a weighted mean, a midrange, a midhinge, a trimean, a Winsorized mean, a mean, or a mode of the corresponding significance score, for each respective cellular constituent in the respective plurality of cellular constituents.

In some embodiments, the activation score of the respective perturbation signature is a difference between (i) a measure of central tendency of the corresponding significance score, for each respective cellular constituent in the respective plurality of cellular constituents, for the respective perturbation signature and (ii) a measure of central tendency of the corresponding first significance score, for each respective cellular constituent in the plurality of reference cellular constituents, for the single-cell transition signature.

In some embodiments, the unaltered cell state of the single-cell transition signature is the same as the first cell state or the second cell state of the respective perturbation signature. In some embodiments, the unaltered cell state of the single-cell transition signature is different than both the first cell state and the second cell state of the respective perturbation signature.

In some embodiments, the method further comprises pruning the reference plurality of cellular constituents of the single-cell transition signature and the respective plurality of cellular constituents of the respective perturbation signature to limit the comparing to transcription factors. In some embodiments, the method further comprises pruning the reference plurality of cellular constituents of the single-cell transition signature and the respective plurality of cellular constituents of the respective perturbation signature to limit the comparing to another cellular constituent type (e.g., genes, carbohydrates, lipids, epigenetic features, metabolites, proteins, and/or a combination thereof). In some embodiments, the reference plurality of cellular constituents and the respective plurality of cellular constituents are not pruned.

In some embodiments, the perturbed state of a respective perturbation signature in the plurality of perturbation signature is represented by control cells that have not been exposed to a compound in the plurality of compounds. In some embodiments, the perturbed state of a respective perturbation signature in the plurality of perturbation signature is represented by an average across unrelated perturbed cells that have been exposed to chemical compounds in the plurality of chemical compounds other than the compound associated with the respective perturbation signature.

As discussed, above, in some embodiments, the respective perturbation signature in the set of perturbation signatures can be determined, as a non-limiting example, using any of the methods disclosed in U.S. patent application Ser. No. 16/511,691 entitled "Methods of Analyzing Cells," filed Jul. 15, 2019, which is hereby incorporated by reference.

The respective perturbation signature comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state. One of the respective first cell state and second cell state is an unperturbed cell state while the other is a respective perturbed cell state caused by exposure of cells to the compound corresponding to the respective perturbation signature. Moreover, as discussed above, the respective perturbation signature includes a numerical activation score. In some embodiments, the numerical activation score for the respective perturbation signature is an absolute value on a continuous scale. In some embodiments, the numerical activation score for the respective perturbation signature is a relative ranking, as discussed in more detail below.

In some embodiments, the respective numerical activation score of a respective perturbation signature in the set of perturbation signatures is obtained by a procedure that comprises accessing, in electronic form, a single-cell transition signature representing a measure of differential cellular constituent abundance between an unaltered cell state and an altered cell state. Here, the altered cell state occurs through the cellular transition from the unaltered cell state to the altered cell state. Moreover, at least one of (i) the unaltered cell state, (ii) the altered cell state, and (iii) the transition from the unaltered cell state to the altered cell state is associated with the physiological condition of interest.

The single-cell transition signature comprises an identification of a reference plurality of cellular constituents and, for each respective cellular constituents in the plurality of reference cellular constituents, a corresponding first significance score that quantifies an association between a change in abundance of the respective cellular constituent and a change in cell state between the unaltered cell state and the altered cell state. In some embodiments, the single-cell transition signature is determined using any of the methods disclosed in U.S. patent application Ser. No. 16/511,691 entitled "Methods of Analyzing Cells," filed Jul. 15, 2019, which is hereby incorporated by reference.

Once obtained, the single-cell transition signature is compared to the respective perturbation signature thereby determining the respective numerical activation score of the respective perturbation signature. In some embodiments, any of the methods for comparing the single-cell transition signature to the respective perturbation signature to determine a relative ranking of the respective perturbation signature, relative to other perturbation signatures in a plurality of perturbation signatures disclosed in U.S. patent application Ser. No. 16/511,691 entitled "Methods of Analyzing Cells," filed Jul. 15, 2019 can be used, where, for example, such relative ranking would then be deemed the respective numerical activation score of the respective perturbation signature.

In some embodiments, the comparison of the single-cell transition signature and the perturbation signature to determine the respective numerical activation score of the respective perturbation signature comprises comparing, for each respective cellular constituent in the reference plurality of cellular constituents of the single-cell transition signature, the first significance score of the respective cellular constituent to the corresponding significance score of the corresponding cellular constituent in the respective perturbation signature. In some such embodiments, the activation score of the respective perturbation signature is a relative ranking of a relevance of the respective perturbation signature, relative to other perturbation signatures in the set of perturbations signatures, to the single-cell transition signature. In some such embodiments, the relative ranking is determined by a Wilcoxon rank-sum test, a t-test, a logistic regression, or a generalized linear model. In some embodiments the activation score of the respective perturbation signature is not a relative ranking of a relevance of the respective perturbation signature but rather is determined independent of the rankings of other perturbation signatures to the single-cell transition signature.

In some embodiments, the activation score of the respective perturbation signature are not based upon a ranking. For instance, in some embodiments, the activation score of the respective perturbation signature is a plurality of significance scores, including the corresponding significance score, for each respective cellular constituent in the respective plurality of cellular constituents for the respective perturbation signature.

In some embodiments, the activation score of the respective perturbation signature is a measure of central tendency of the corresponding significance score, for each respective cellular constituent in the respective plurality of cellular constituents for the respective perturbation signature. In some embodiments, the measure of central tendency is an arithmetic mean, a weighted mean, a midrange, a midhinge, a trimean, a Winsorized mean, a mean, or a mode of the corresponding significance score, for each respective cellular constituent in the respective plurality of cellular constituents.

In some embodiments, the activation score of the respective perturbation signature is a difference between (i) a measure of central tendency of the corresponding significance score, for each respective cellular constituent in the respective plurality of cellular constituents, for the respective perturbation signature and (ii) a measure of central tendency of the corresponding first significance score, for each respective cellular constituent in the plurality of reference cellular constituents, for the single-cell transition signature.

In one embodiment, to perform the comparison between the single-cell transition signature and a respective perturbation signature, the cellular constituents of the perturbation signatures are represented as a matrix. Each row of the matrix is associated with a single perturbation (e.g., a single compound in the plurality of compounds). Each column on the matrix is associated with one of the cellular constituents exhibiting differential abundance between respective states. Each entry in the matrix includes a significance score (e.g., a p-value, a t-score) for a cellular constituent identified for a particular perturbation signature. This matrix is filtered to include only the cellular constitutes that are in the single-cell transition signature. This filtering may be accomplished using a threshold p-value, the use of a threshold number of cellular-components, or the like.

Each significance score in the matrix is replaced with a discrete matching score. To replace each significance score with a discrete matching score, the significantly up-regulated cellular constituents for the cellular transition and the significantly down-regulated cellular constituents for the cellular transition are identified. For each of the significantly up-regulated cellular constituents identified by the single-cell transition signature, if the cellular constituent is also significantly up-regulated for the perturbation signature for that perturbation (e.g., chemical composition), the significance score in the matrix for that cellular constituent/perturbation combination is replaced with a discrete matching score of "1". If the cellular constituent is significantly down-regulated for a perturbation signature relative to the single-cell transition signature, the significance score in the matrix for that cellular constituent/perturbation combination is replaced with a discrete matching score of "−2". If the cellular constituent is not significantly up-regulated or down-regulated for a perturbation signature, the significance score in the matrix for the cellular constituent/perturbation combination is replaced with a discrete matching score of "0."

Conversely, for each of the significantly down-regulated cellular constituents identified in the single-cell transition signature, if the cellular-component is also significantly down-regulated for a perturbation, the significance score in the matrix for that cellular constituent/perturbation combination is replaced with a discrete matching score of "−1." If the cellular constituent is significantly up-regulated for a perturbation, the significance score in the matrix for that cellular constituent/perturbation combination is replaced with a discrete matching score of "2." If the cellular constituent is not significantly up-regulated or down-regulated for a perturbation, the significance score in the matrix for that cellular constituent/perturbation combination is replaced with a discrete matching score of "0." One of skill in the art will appreciate that these particular score replacements may be substituted with other numerical values in some embodiments. Moreover, rather than up-regulation or down-regulation, the use of a threshold abundance value for each cellular constituent may be used, where then, a consideration of whether a given cellular constituent is above or below the threshold abundance value is made in assigning the aforementioned class labels (e.g., "−1", "2", "0", etc.) to each element of the matrix.

The result is a matrix with the number of rows given by the number of perturbations (the number of chemical compositions in the plurality of chemical compositions and therefore the number of perturbation signatures in the plurality of perturbation signatures) and the number of columns given by the differential cellular constituents from the single-cell transition with the matrix element entries representing the matching scores described above.

Following replacement of the significance scores in the matrix with the discrete matching scores as described above, the discrete matching scores in each row of the matrix are summed to generate a summed matching score for each row. Then, the rows of the matrix, each corresponding to a perturbation signature, are ranked in order of decreasing summed matching score. The top-ranked rows are associated with the perturbation signatures that are most likely to be associated with the identified cellular transition of the single-cell transition signature. Moreover, the ranking of each of the rows can be used as the activation scores for the perturbation signatures corresponding to each of the rows.

In some embodiments, for the summed matching score of each row in the matrix, an estimation of the false cellular-component discovery rate is estimated as discussed in U.S. patent application Ser. No. 16/511,691 entitled "Methods of Analyzing Cells," filed Jul. 15, 2019, which is hereby incorporated by reference.

In certain embodiments, covariates of a perturbation (e.g., exposure of cells to a particular chemical composition) may exist. For example, covariates of a chemical composition may include: a specific dose of the chemical composition, a time at which the cells exposed to the chemical composition is measured to quantify cellular constituents, and/or the identity (e.g., cell line) of the cells exposed to the chemical composition. In some embodiments, a perturbation (e.g., exposure of cells to a particular chemical composition) is predicted to affect a particular cellular transition only when a threshold quantity of its covariates is also predicted to affect the particular cellular transition. In other words, in some embodiments, the numerical activation score of a particular perturbation signature is determined at least in part by whether the covariates of the chemical composition of the particular perturbation signature are also predicted to affect the particular cellular transition associated with the single-cell transition score.

Alternate methods of comparing a respective perturbation signature to a single cell-transition signature may be used to determine the numerical activation score of the respective perturbation signature. For example, cellular constituents may be matched to a database using a web interface (e.g., such as L1000CDS2. An ultra-fast LINCS L1000 Characteristic Direction Signature Search Engine, on world wide web at amp.pharm.mssm.edu/L1000CDS2/#/index).

In some embodiments, the unaltered cell state of the single-cell transition signature is the same as the first cell state or the second cell state of the respective perturbation signature. In some embodiments, the unaltered cell state of the single-cell transition signature is different than both the first cell state and the second cell state of the respective perturbation signature.

In some embodiments, the method further comprises pruning the reference plurality of cellular constituents of the single-cell transition signature and the respective plurality of cellular constituents of the respective perturbation signature to limit the comparing to transcription factors. In some embodiments, the perturbed state of a respective perturbation signature in the plurality of perturbation signature is represented by control cells that have not been exposed to a compound in the plurality of compounds.

In some embodiments, the perturbed state of a respective perturbation signature in the plurality of perturbation signature is represented by an average across unrelated perturbed cells that have been exposed to chemical compounds in the plurality of chemical compounds other than the compound associated with the respective perturbation signature.

Referring to Block 908, the method further includes training an untrained model using, for each respective chemical structure of each respective compound in the plurality of compounds, for each respective perturbation signature in the set of perturbation signature, a respective difference between: (i) a respective calculated activation score for the respective perturbation signature upon input of the fingerprint of the chemical structure of the respective compound into the untrained model and (ii) the respective numerical activation score of the respective perturbation signature for the corresponding compound in the set of perturbation signatures.

Any suitable embodiments of models, such as those disclosed in the above section entitled "Model architectures," are contemplated, and any substitutions, modifications, additions, deletions, and/or combinations thereof, as will be apparent to one skilled in the art. For instance, in some embodiments, the trained model comprises a neural network. In some embodiments, the neural network is a fully connected neural network with ReLU activation. In some embodiments, the neural network is a message passing neural network. In some embodiments, the trained model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

In some embodiments, the trained model is an ensemble model of a plurality of component models, and the respective calculated activation score is a measure of central tendency of an output of each component model in the plurality of component models. In some embodiments, the plurality of component models comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model. In some embodiments, the plurality of component models comprises a plurality of neural networks. In some embodiments, a first neural network in the plurality of neural networks is a fully connected neural network with ReLU activation, and a second neural network in the plurality of neural networks is a message passing neural network.

Referring to Block 910, the training adjusts a plurality of parameters associated with the untrained model responsive to the difference, where the plurality of parameters comprises 100 or more parameters, thereby obtaining a trained model that associates chemical compounds with the physiological condition of interest.

Any suitable methods and embodiments for training an untrained or partially trained model, such as those disclosed in the above section entitled "Model training," are contemplated, including any substitutions, modifications, additions, deletions, and/or combinations thereof, as will be apparent to one skilled in the art.

For in some embodiments, input to the model includes a plurality of activation scores, each respective activation score corresponding to a respective perturbation signature in a set of perturbation signatures, for each compound in a plurality of compounds. Activation scores corresponding to each respective perturbation signature for each respective compound serve as labels (e.g., numerical activation scores indicating an actual presence or absence of association between perturbation signatures and compounds) for training a multi-task model to identify associations (e.g., weights and/or correlations) between perturbation signatures and compounds. For instance, as described above, in some embodiments, a first subset of the plurality of perturbation signatures is associated with the physiological condition of interest, and a second subset of the plurality of perturbation signatures is not associated with the physiological condition of interest. Thus, in some such embodiments, an actual presence of association can be included in the training dataset using the first subset of the plurality of perturbation signatures as labels, and an actual absence of association can be included in the training dataset using the second subset of the plurality of perturbation signatures as labels.

In some embodiments, the training adjusts the plurality of parameters associated with the untrained model responsive to each difference associated with each corresponding compound for each respective perturbation signature in the set of perturbation signatures s in accordance with a regression model. In some embodiments, the regression model optimizes a least square error of the each difference associated with each corresponding compound for each respective perturbation signature in the set of perturbation signatures.

In some embodiments, the model is trained and/or used for associating compounds with physiological conditions of interest based on activation scores for cellular constituent modules, perturbation signatures, or both. In some embodiments, the model is trained and/or used for associating compounds with physiological conditions of interest based on activation scores for a plurality of domains (e.g., label types, such as modules and/or perturbation signatures) and/or data types (e.g., analytes and/or cellular constituents, such as gene expression profiles, metabolomics, proteomics, epigenetics, etc.). In some embodiments, the model is trained and/or used for associating compounds with physiological conditions of interest based on activation scores for any one or more physiological conditions of interest (e.g., toxicity of a compound, resolution of a disease state, etc.). In some embodiments, the model is trained across a plurality of systems, where systems refer to any one or more physiological conditions, any one or more domains, and/or any one or more data types disclosed herein, or any substitutions, modifications, additions, deletions, and/or combinations that will be apparent to one skilled in the art. For instance, in some embodiments, the model is jointly trained to collectively determine associations between a test chemical compound, activations of a gene module characteristics of toxicity, and a perturbation signature indicative of disease resolution.

ADDITIONAL EMBODIMENTS

Another aspect of the present disclosure provides a computer system, comprising one or more processors and memory, the memory storing instructions for performing a method for associating a test chemical compound with a physiological condition of interest. The method comprises obtaining a fingerprint of a chemical structure of the test chemical compound and inputting the fingerprint into a model, where the model comprises 100 or more parameters, the model outputs one or more calculated activation scores responsive to the inputting of the fingerprint into the model, each respective calculated activation score in the one or more calculated activation scores represents a corresponding cellular constituent module in a set of cellular constituent modules, each respective cellular constituent module in the set of cellular constituent modules includes an independent subset of a plurality of cellular constituents, and a first cellular constituent module in the set of cellular constituent modules is associated with the physiological condition of interest. The method further comprises identifying the chemical compound with the physiological condition of interest when the respective calculated activation score for the first cellular constituent module satisfies a first threshold criterion.

Another aspect of the present disclosure provides a non-transitory computer-readable medium storing one or more computer programs, executable by a computer, for associating a test chemical compound with a physiological condition of interest, the computer comprising one or more processors and a memory, the one or more computer programs collectively encoding computer executable instructions that perform a method. The method comprises obtaining a fingerprint of a chemical structure of the test chemical compound and inputting the fingerprint into a model, where the model comprises 100 or more parameters, the model outputs one or more calculated activation scores responsive to the inputting of the fingerprint into the model, each respective calculated activation score in the one or more calculated activation scores represents a corresponding cellular constituent module in a set of cellular constituent modules, each respective cellular constituent module in the set of cellular constituent modules includes an independent subset of a plurality of cellular constituents, and a first cellular constituent module in the set of cellular constituent modules is associated with the physiological condition of interest. The method further comprises identifying the chemical compound with the physiological condition of interest when the respective calculated activation score for the first cellular constituent module satisfies a first threshold criterion.

Still another aspect of the present disclosure provides a computer system, comprising one or more processors and memory, the memory storing instructions for performing a method for associating a test chemical compound with a physiological condition of interest. The method comprises obtaining a fingerprint of a chemical structure of the test chemical compound and inputting the fingerprint into a model, where the model comprises 100 or more parameters. The model outputs one or more calculated activation scores responsive to the inputting of the fingerprint into the model. Each respective calculated activation score in the one or more calculated activation scores represents a corresponding perturbation signature in a set of perturbation signatures. Each respective perturbation signature in the set of perturbation signature comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound. The method further comprises identifying the chemical compound with the physiological condition of interest when the respective calculated activation score for a first perturbation signature in the set of perturbation signatures satisfies a first threshold criterion.

Another aspect of the present disclosure provides a non-transitory computer-readable medium storing one or more computer programs, executable by a computer, for associating a test chemical compound with a physiological condition of interest, the computer comprising one or more processors and a memory, the one or more computer programs collectively encoding computer executable instructions that perform a method. The method comprises obtaining a fingerprint of a chemical structure of the test chemical compound and inputting the fingerprint into a model, where the model comprises 100 or more parameters. The model outputs one or more calculated activation scores responsive to the inputting of the fingerprint into the model. Each respective calculated activation score in the one or more calculated activation scores represents a corresponding perturbation signature in a set of perturbation signatures. Each respective perturbation signature in the set of perturbation signature comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound. The method further comprises identifying the chemical compound with the physiological condition of interest when the respective calculated activation score for a first perturbation signature in the set of perturbation signatures satisfies a first threshold criterion.

Still another aspect of the present disclosure provides a computer system, comprising one or more processors and memory, the memory storing instructions for performing a method for associating chemical compounds with a physiological condition of interest. The method comprises obtaining, in electronic form, a respective fingerprint of a chemical structure of each compound in a plurality of compounds, thereby obtaining a plurality of fingerprints. The method includes obtaining, in electronic form, a respective numerical activation score of each cellular constituent module in a set of cellular constituent modules for each compound in the plurality of compounds, where each respective cellular constituent module in the set of cellular constituent modules includes an independent subset of a plurality of cellular constituents. The method further includes training an untrained model using for each respective chemical structure of each respective compound in the plurality of compounds, for each respective cellular constituent module in the set of cellular constituent modules, a respective difference between (i) a respective calculated activation score for the respective cellular constituent module upon input of the fingerprint of the chemical structure of the respective compound into the untrained model and (ii) the respective numerical activation score of the respective cellular constituent module for the respective compound in the set of cellular constituent modules. The training adjusts a plurality of parameters associated with the untrained model responsive to the difference, where the plurality of parameters comprises 100 or more parameters, thereby obtaining a trained model that associates chemical compounds with the physiological condition of interest.

Another aspect of the present disclosure provides a non-transitory computer-readable medium storing one or more computer programs, executable by a computer, for associating chemical compounds with a physiological condition of interest, the computer comprising one or more processors and a memory, the one or more computer programs collectively encoding computer executable instructions that perform a method. The method comprises obtaining, in electronic form, a respective fingerprint of a chemical structure of each compound in a plurality of compounds, thereby obtaining a plurality of fingerprints. The method further comprises obtaining, in electronic form, a respective numerical activation score of each cellular constituent module in a set of cellular constituent modules for each compound in the plurality of compounds, where each respective cellular constituent module in the set of cellular constituent modules includes an independent subset of a plurality of cellular constituents. The method further includes training an untrained model using for each respective chemical structure of each respective compound in the plurality of compounds, for each respective cellular constituent module in the set of cellular constituent modules, a respective difference between (i) a respective calculated activation score for the respective cellular constituent module upon input of the fingerprint of the chemical structure of the respective compound into the untrained model and (ii) the respective numerical activation score of the respective cellular constituent module for the respective compound in the set of cellular constituent modules. The training adjusts a plurality of parameters associated with the untrained model responsive to the difference, where the plurality of parameters comprises 100 or more parameters, thereby obtaining a trained model that associates chemical compounds with the physiological condition of interest.

Still another aspect of the present disclosure provides a computer system, comprising one or more processors and memory, the memory storing instructions for associating chemical compounds with a physiological condition of interest, the method comprising obtaining, in electronic form, a respective fingerprint of a chemical structure of each compound in a plurality of compounds, thereby obtaining a plurality of fingerprints. The method further includes obtaining, in electronic form, a respective numerical activation score of each respective perturbation signature in a set of perturbations signatures for each corresponding compound in the plurality of compounds. Each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound. The method includes training an untrained model using, for each respective chemical structure of each respective compound in the plurality of compounds, for each respective perturbation signature in the set of perturbation signature, a respective difference between: (i) a respective calculated activation score for the respective perturbation signature upon input of the fingerprint of the chemical structure of the respective compound into the untrained model and (ii) the respective numerical activation score of the respective perturbation signature for the corresponding compound in the set of perturbation signatures. The training adjusts a plurality of parameters associated with the untrained model responsive to the difference, where the plurality of parameters comprises 100 or more parameters, thereby obtaining a trained model that associates chemical compounds with the physiological condition of interest.

Another aspect of the present disclosure provides a non-transitory computer-readable medium storing one or more computer programs, executable by a computer, for associating chemical compounds with a physiological condition of interest, the computer comprising one or more processors and a memory, the one or more computer programs collectively encoding computer executable instructions that perform a method comprising obtaining, in electronic form, a respective fingerprint of a chemical structure of each compound in a plurality of compounds, thereby obtaining a plurality of fingerprints. The method further includes obtaining, in electronic form, a respective numerical activation score of each respective perturbation signature in a set of perturbations signatures for each corresponding compound in the plurality of compounds. Each respective perturbation signature in the set of perturbation signatures comprises an identification of a respective plurality of cellular constituents and, for each respective cellular constituent in the respective plurality of cellular constituents, a corresponding significance score that quantifies an association between a change in abundance of the respective cellular constituent and a change in cell state between a respective first cell state and a respective second cell state, where one of the respective first cell state and second cell state is an unperturbed cell state and the other of the respective first cell state and the second cell state is a respective perturbed cell state caused by exposure of cells to the corresponding compound. The method further comprises training an untrained model using, for each respective chemical structure of each respective compound in the plurality of compounds, for each respective perturbation signature in the set of perturbation signature, a respective difference between: (i) a respective calculated activation score for the respective perturbation signature upon input of the fingerprint of the chemical structure of the respective compound into the untrained model and (ii) the respective numerical activation score of the respective perturbation signature for the corresponding compound in the set of perturbation signatures. The training adjusts a plurality of parameters associated with the untrained model responsive to the difference, where the plurality of parameters comprises 100 or more parameters, thereby obtaining a trained model that associates chemical compounds with the physiological condition of interest.

Still another aspect of the present disclosure provides a computer system having one or more processors, and memory storing one or more programs for execution by the one or more processors, the one or more programs comprising instructions for performing any of the methods and/or embodiments disclosed herein. In some embodiments, any of the presently disclosed methods and/or embodiments are performed at a computer system having one or more processors, and memory storing one or more programs for execution by the one or more processors.

Another aspect of the present disclosure provides a non-transitory computer readable storage medium storing one or more programs configured for execution by a computer, the one or more programs comprising instructions for carrying out any of the methods disclosed herein.

IV. IDENTIFYING CELLULAR CONSTITUENT MODULES

In some embodiments, cellular constituent modules 132 associated with the physiological condition of interest are identified. Such methods are discussed here in conjunction with FIGS. 2 and 14. In particular, with reference to Block 1500 of FIGS. 14A-14D, in some embodiments, the method further comprises identifying a first cellular constituent module 132 associated with a physiological condition of interest.

An example workflow of a method 200 for associating cellular constituents with a physiological condition of interest, in accordance with some embodiments of the present disclosure, is provided with reference to FIGS. 2A-B.

Figure 14A:
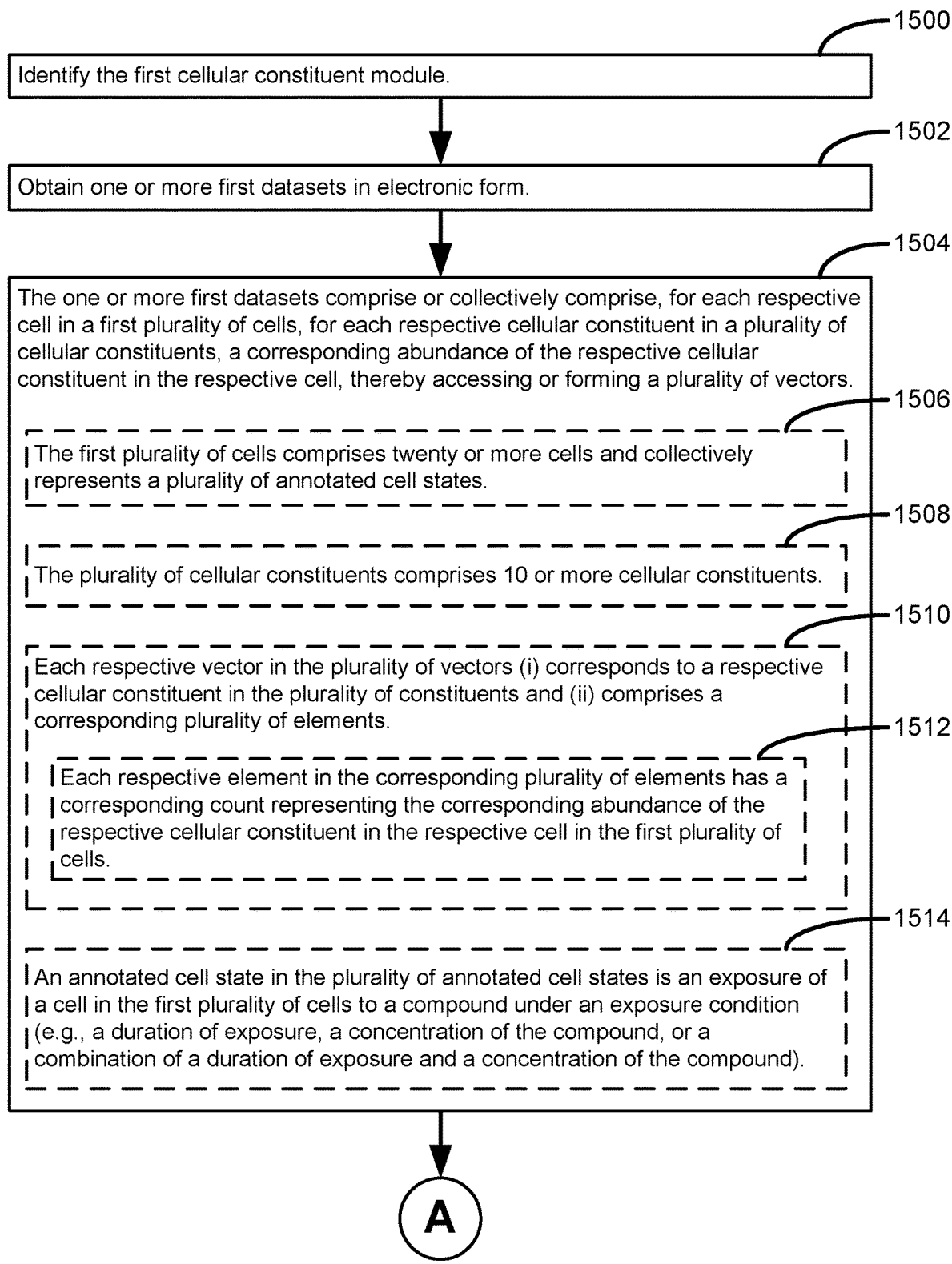
FIGS. 14A, 14B, 14C, and 14D provide a flow chart of identifying a cellular constituent module in which optional elements are indicated by dashed boxes.

Referring to Block 202 of FIG. 2A and Block 1502 of FIG. 14A, the method includes obtaining one or more first datasets in electronic form. Referring to Block 1504 of FIG. 14B, the one or more first datasets comprising or collectively comprise, for each respective cell in a first plurality of cells, for each respective cellular constituent in the plurality of cellular constituents, a corresponding abundance of the respective cellular constituent in the respective cell. In this way a plurality of vectors is obtained.

In some embodiments, the physiological condition of interest is a disease, and the first plurality of cells includes cells that are representative of the disease and cells that are not representative of the disease as documented by the plurality of annotated cell states.

In some embodiments, the physiological condition of interest of Block 300 of FIG. 3A is an aberrant cell process associated with a disease, and the first plurality of cells includes cells that are representative of the disease and cells that are not representative of the disease as documented by the plurality of annotated cell states.

In some embodiments, the physiological condition of interest of Block 300 of FIG. 3A is an aberrant cell process associated with a disease, and the first plurality of cells includes cells that are representative of a disease state and cells that are representative of a healthy or control state as documented by the plurality of annotated cell states.

In some embodiments, the physiological condition of interest of Block 300 of FIG. 3A is an aberrant cell process associated with a plurality of diseases, and the first plurality of cells includes a plurality of subsets of cells, each respective subset of cells representative of a respective disease in the plurality of diseases as documented by the plurality of annotated cell states.

Figure 14B:
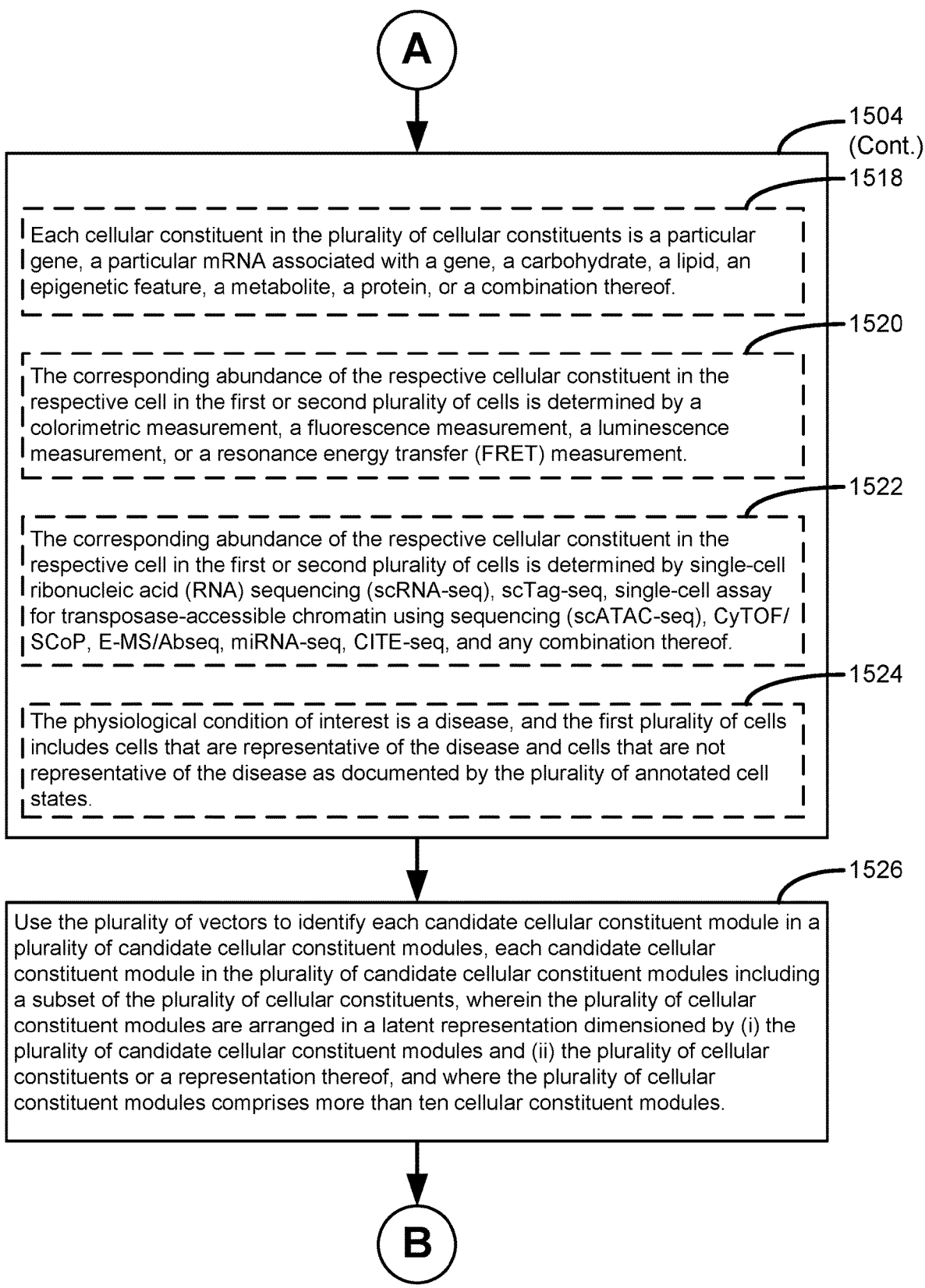

Referring to Block 1506 of FIG. 14B, in some embodiments, the first plurality of cells comprises 2, 3, 4, 5, 6, 7, 8, 9, 10, 11, 12, 13, 14, 15, 16, 17, 18, 19, 20, 30, 40, 50, 60, 70, 80, 100, 200, or 1000 or more cells and collectively represents a plurality (e.g., 2, 3, 4, 5, 6, 7, 8, 9, 10, 11, 12, 13, 14, 15, 16, 17, 18, 19, 20, 30, 40, 50, 60, 70, 80, 100, 200, or 1000) of annotated cell states.

Referring to Block 1508 of FIG. 14B, in some embodiments, the plurality of cellular constituents comprises 2, 3, 4, 5, 6, 7, 8, 9, 10, 15, 20, 25, 30, 35, 50, 100, 500, 1000, 5000, 10,000 or more cellular constituents. In some embodiments, the plurality of cellular constituents consists of between 2 and 10,000 or cellular constituents. In some embodiments, the plurality of cellular constituents consists of between 100 and 10,000 or cellular constituents.

Referring to Block 204 of FIG. 2A, the method includes accessing or forming a plurality of vectors. Referring to Block 1510 of FIG. 14A, each respective vector in the plurality of vectors (i) corresponds to a respective cellular constituent in the plurality of constituents and (ii) comprises a corresponding plurality of elements. Referring to Block 1512 of FIG. 14A, each respective element in the corresponding plurality of elements has a corresponding count representing the corresponding abundance of the respective cellular constituent in the respective cell in the first plurality of cells.

Referring to Block 206, the plurality of vectors is used to identify each candidate cellular constituent module in a plurality of candidate cellular constituent module. Each candidate cellular constituent module in the plurality of candidate cellular constituent modules includes a subset of the plurality of cellular constituents. The plurality of cellular constituent modules is arranged in a latent representation dimensioned by (i) the plurality of candidate cellular constituent modules and (ii) the plurality of cellular constituents or a representation thereof, where the plurality of cellular constituent modules comprises more than ten cellular constituent modules.

Referring to Block 1514 of FIG. 14B, in some embodiments an annotated cell state in the plurality of annotated cell states is an exposure of a cell in the first plurality of cells to a compound under an exposure condition (e.g., a duration of exposure, a concentration of the compound, or a combination of a duration of exposure and a concentration of the compound).

Referring to Block 1518 of FIG. 14B, in some embodiments each cellular constituent in the plurality of cellular constituents is a particular gene, a particular mRNA associated with a gene, a carbohydrate, a lipid, an epigenetic feature, a metabolite, a protein, or a combination thereof.

Referring to Block 1520 of FIG. 14B, in some embodiments the corresponding abundance of the respective cellular constituent in the respective cell in the first or second plurality of cells is determined by a colorimetric measurement, a fluorescence measurement, a luminescence measurement, or a resonance energy transfer (FRET) measurement.

Referring to Block 1522 of FIG. 14B, in some embodiments the corresponding abundance of the respective cellular constituent in the respective cell in the first or second plurality of cells is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, or any combination thereof.

Referring to Block 1524 of FIG. 14B, some embodiments the physiological condition of interest is a disease, and the first plurality of cells includes cells that are representative of the disease and cells that are not representative of the disease as documented by the plurality of annotated cell states.

Referring to Block 1526 of FIG. 14B, the plurality of vectors are used to identify each candidate cellular constituent module in a plurality of candidate cellular constituent modules, each candidate cellular constituent module in the plurality of candidate cellular constituent modules including a subset of the plurality of cellular constituents. The plurality of cellular constituent modules are arranged in a latent representation dimensioned by (i) the plurality of candidate cellular constituent modules and (ii) the plurality of cellular constituents or a representation thereof, and where the plurality of cellular constituent modules comprises more than ten cellular constituent modules.

Figure 14C:
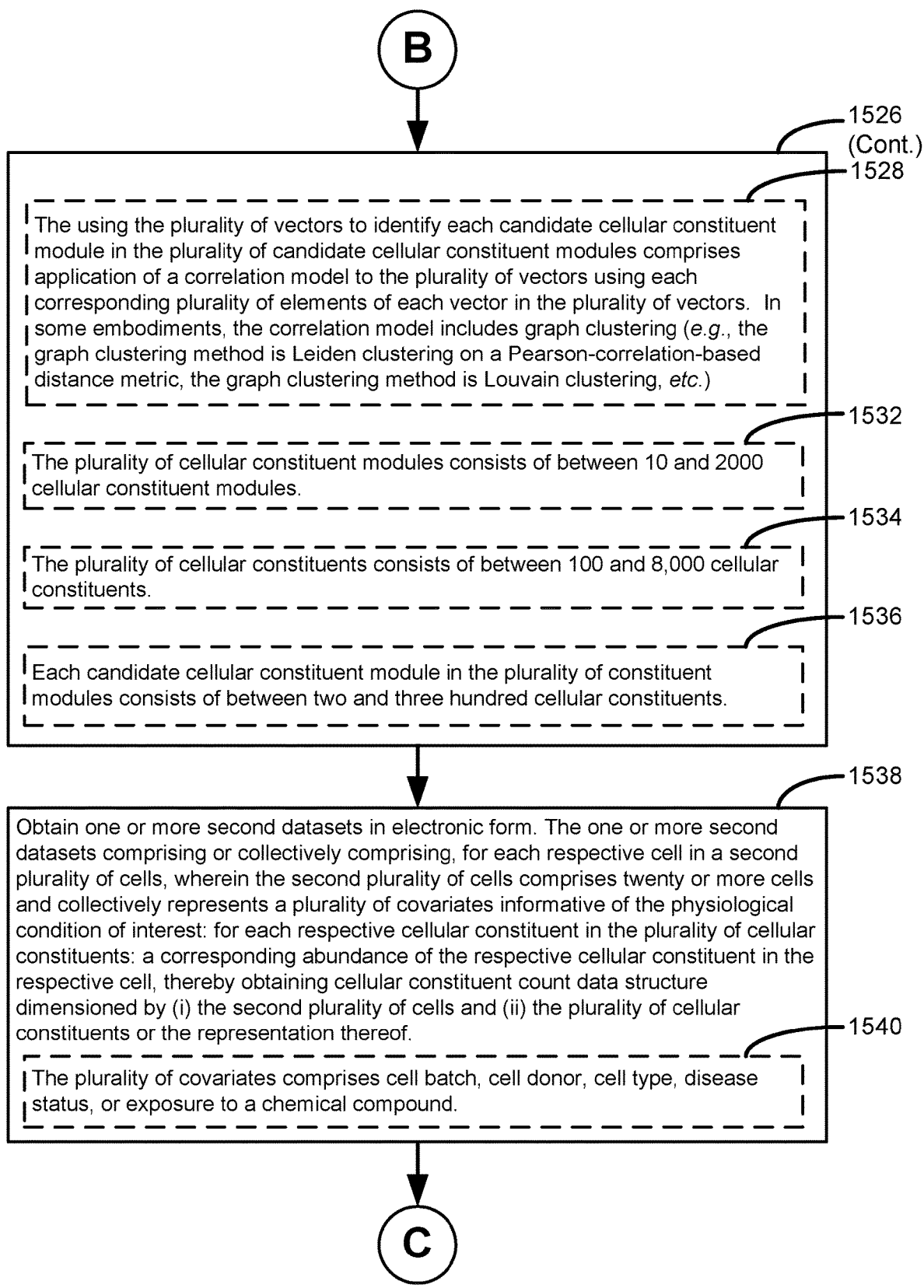

Referring to Block 1528 of FIG. 14C, in some embodiments the using the plurality of vectors to identify each candidate cellular constituent module in the plurality of candidate cellular constituent modules comprises application of a correlation model to the plurality of vectors using each corresponding plurality of elements of each vector in the plurality of vectors. In some embodiments, the correlation model includes a graph clustering algorithm (e.g., the graph clustering method is Leiden clustering on a Pearson-correlation-based distance metric, the graph clustering method is Louvain clustering, etc.).

Referring to Block 1532 of FIG. 14C, in some embodiments, the plurality of cellular constituent modules consists of between 10 and 2000, between 100 and 10000, between 20 and 5000, between 2 and 15,000, between 80 and 5000, between 100 and 500 cellular constituent modules. In some embodiments the plurality of cellular constituent modules is between 2 and 500 cellular constituent modules.

Referring to Block 1534 of FIG. 14C, in some embodiments, the plurality of cellular constituents consists of between 10 and 2000, between 100 and 10000, between 20 and 5000, between 2 and 15,000, between 80 and 5000, between 100 and 500 cellular constituents. In some embodiments the plurality of cellular constituents is between 2 and 500 cellular constituents.

Referring to Block 1536 of FIG. 14C, in some embodiments each candidate cellular constituent module in the plurality of constituent modules consists of between two and three hundred cellular constituents.

Referring to Block 208 of FIG. 2A and Block 1538 of FIG. 14C, the method includes obtaining one or more second datasets in electronic form. The one or more second datasets comprise or collectively comprise, for each respective cell in a second plurality of cells, where the second plurality of cells comprises twenty or more cells and collectively represents a plurality of covariates informative of the physiological condition of interest, for each respective cellular constituent in the plurality of cellular constituents, a corresponding abundance of the respective cellular constituent in the respective cell. Thus, a cellular constituent count data structure is obtained, where the cellular constituent count data structure is dimensioned by (i) the second plurality of cells and (ii) the plurality of cellular constituents or the representation thereof.

Referring to Block 1540 of FIG. 14C, in some embodiments, the plurality of covariates comprises cell batch, cell donor, cell type, disease status, or exposure to a chemical compound.

Figure 14D:
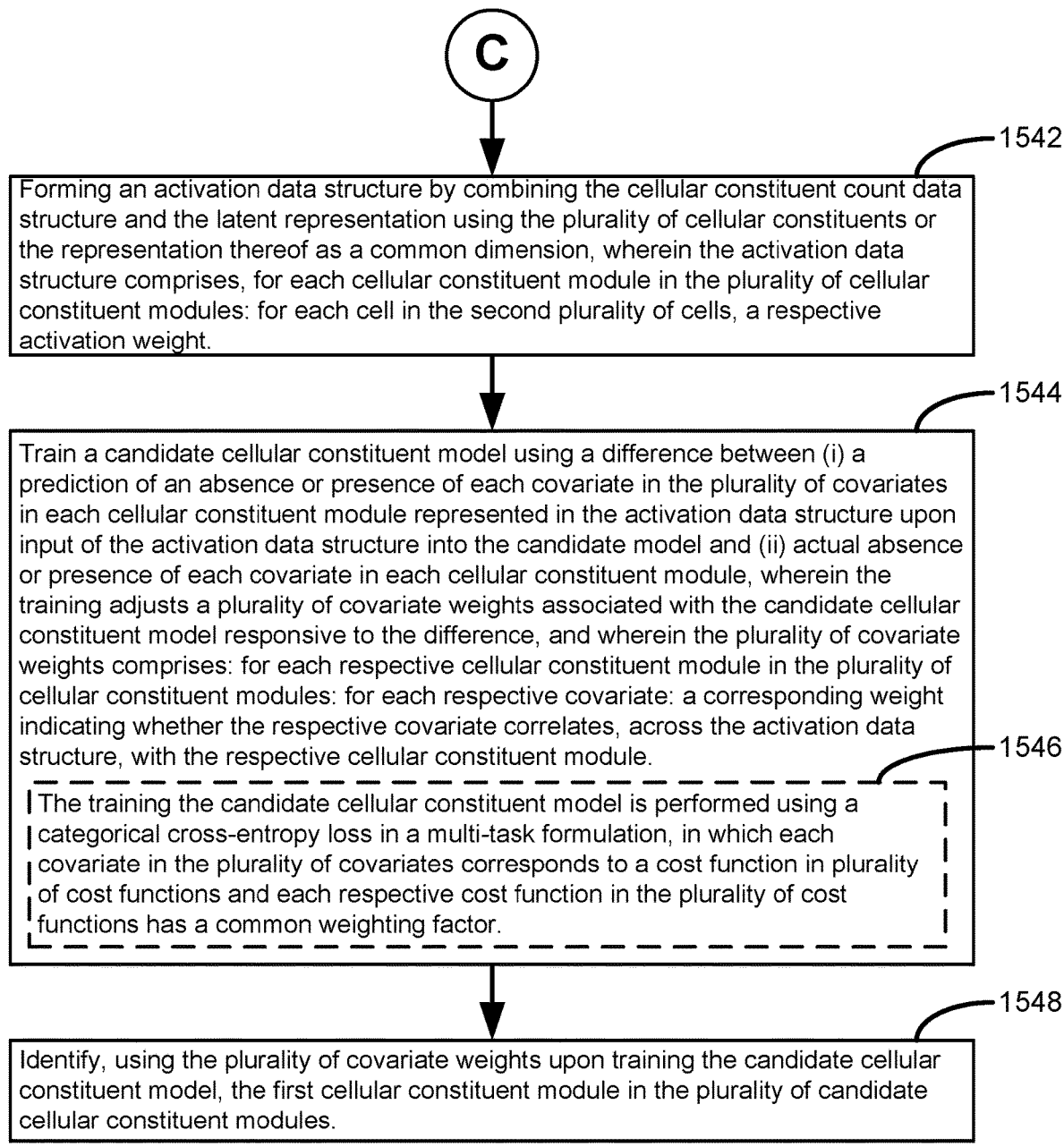

Referring to Block 210 of FIG. 2B and Block 1542 FIG. 14D, an activation data structure is formed by combining the cellular constituent count data structure and the latent representation using the plurality of cellular constituents or the representation thereof as a common dimension. The activation data structure comprises, for each cellular constituent module in the plurality of cellular constituent modules, for each cell in the second plurality of cells, a respective activation weight.

Referring to Block 212 of FIG. 2B and Block 1544 of FIG. 14D, the method further comprises training a candidate cellular constituent model using a difference between (i) a prediction of an absence or presence of each covariate in the plurality of covariates in each cellular constituent module represented in the activation data structure upon input of the activation data structure into the candidate model and (ii) actual absence or presence of each covariate in each cellular constituent module. The training adjusts a plurality of covariate weights associated with the candidate cellular constituent model responsive to the difference, where the plurality of covariate weights comprises, for each respective cellular constituent module in the plurality of cellular constituent modules, for each respective covariate, a corresponding weight indicating whether the respective covariate correlates, across the activation data structure, with the respective cellular constituent module.

Referring to Block 1546 of FIG. 14D, the training the candidate cellular constituent model is performed using a categorical cross-entropy loss in a multi-task formulation, in which each covariate in the plurality of covariates corresponds to a cost function in plurality of cost functions and each respective cost function in the plurality of cost functions has a common weighting factor.

Thus, referring to Block 214 of FIG. 2C and block 1548 of FIG. 14D, the plurality of covariate weights is used, upon training the candidate cellular constituent model, to identify the first cellular constituent module in the plurality of candidate cellular constituent modules, where the first cellular constituent module in the plurality of candidate cellular constituent modules is associated with the physiological condition of interest.

In some embodiments, the first and/or the second plurality of cells comprises at least 5, at least 10, at least 15, at least 20, at least 30, at least 40, at least 50, at least 100, at least 200, at least 300, at least 400, at least 500, at least 1000, at least at least 2000, at least 3000, at least 4000, at least 5000, at least 10,000, at least 20,000, at least 30,000, at least 50,000, at least 80,000, at least 100,000, at least 500,000, or at least 1 million cells. In some embodiments, the first and/or the second plurality of cells comprises no more than 5 million, no more than 1 million, no more than 500,000, no more than 100,000, no more than 50,000, no more than 10,000, no more than 5000, no more than 1000, no more than 500, no more than 200, no more than 100, or no more than 50 cells. In some embodiments, the first and/or the second plurality of cells comprises from 5 to 100, from 10 to 50, from 20 to 500, from 200 to 10,000, from 1000 to 100,000, from 50,000 to 500,000, or from 10,000 to 1 million cells. In some embodiments, the first and/or the second plurality of cells falls within another range starting no lower than 5 cells and ending no higher than 5 million cells.

In some embodiments, the second plurality of cells does not include any cells included in the first plurality of cells. In some embodiments, the second plurality of cells includes some or all of the cells included in the first plurality of cells.

In some embodiments, the plurality of annotated cell states comprises one or more of a cell phenotype, cellular behavior, disease state, genetic mutation, perturbations of genes or gene products (e.g., knockdowns, silencing, over-expression, etc.), and/or exposure to a compound. In some embodiments, an annotated cell state in the plurality of annotated cell states is an exposure of a cell in the first plurality of cells to a compound under an exposure condition. For example, an exposure of a cell includes any treatment of the cell with one or more compounds. In some embodiments, the one or more compounds includes, for example, a small molecule, a biologic, a therapeutic, a protein, a protein combined with a small molecule, an ADC, a nucleic acid (e.g., an siRNA, interfering RNA, cDNA over-expressing wild-type and/or mutant shRNA, cDNA over-expressing wild-type and/or mutant guide RNA (e.g., Cas9 system or other cellular-component editing system), etc.), and/or any combination of any of the foregoing. In some embodiments, the exposure condition is a duration of exposure, a concentration of the compound, or a combination of a duration of exposure and a concentration of the compound. In some embodiments, the compound is any of the embodiments described herein, such as in the section entitled "Compounds," above.

In some embodiments, the plurality of annotated cell states comprises one or more indications of cell batch, cell donor, cell type, cell line, disease status, time points, replicates, and/or relevant metadata. In some embodiments, the plurality of annotated cell states comprises experimental data (e.g., flow cytometry readouts, imaging and microscopy annotations, cellular constituent data, etc.). In some embodiments, the plurality of annotated cell states comprises one or more genetic markers (e.g., copy number variations, single nucleotide variants, multiple nucleotide polymorphisms, insertions, deletions, gene fusions, microsatellite instability status, amplifications, and/or isoforms). In some embodiments, the plurality of annotated cell states includes any of the covariates disclosed herein and/or any of the physiological conditions of interest disclosed herein, such as in the section entitled, "Physiological conditions," above.

Any cellular constituent disclosed herein and/or any cellular constituent module, and any embodiments, substitutions, modifications, additions, deletions, and/or combinations thereof are contemplated for the identification of cellular constituent modules, as described in the section entitled, "Cellular constituents and cellular constituent modules," above. For example, in some embodiments, each cellular constituent in the plurality of cellular constituents is a particular gene, a particular mRNA associated with a gene, a carbohydrate, a lipid, an epigenetic feature, a metabolite, a protein, or a combination thereof. In some embodiments, the plurality of cellular constituents consists of between 100 and 8,000 cellular constituents. In some embodiments, the plurality of cellular constituent modules consists of between 10 and 2000 cellular constituent modules. In some embodiments, each candidate cellular constituent module in the plurality of constituent modules consists of between two and three hundred cellular constituents.

In some embodiments, the corresponding abundance of a respective cellular constituent comprises an abundance of any of the cellular constituents disclosed above.

Any one of a number of abundance counting techniques (e.g., cellular constituent measurement techniques) may be used to obtain the corresponding abundance for each respective cellular constituent in each respective cell. For instance, Table 1 lists non-limiting techniques for single-cell cellular constituent measurement, in accordance with some embodiments of the present disclosure.

In some embodiments, the corresponding abundance of the respective cellular constituent is determined using one or more methods including microarray analysis via fluorescence, chemiluminescence, electric signal detection, polymerase chain reaction (PCR), reverse transcriptase polymerase chain reaction (RT-PCR), digital droplet PCR (ddPCR), solid-state nanopore detection, RNA switch activation, a Northern blot, and/or a serial analysis of gene expression (SAGE). In some embodiments, the corresponding abundance of the respective cellular constituent in the respective cell in the first and/or second plurality of cells is determined by a colorimetric measurement, a fluorescence measurement, a luminescence measurement, or a resonance energy transfer (FRET) measurement.

In some embodiments, gene expression in a respective cell in the first and/or the second plurality of cells can be measured by sequencing the cell and then counting the quantity of each gene transcript identified during the sequencing. In some embodiments, the gene transcripts sequenced and quantified include RNA, such as mRNA. In some embodiments, the gene transcripts sequenced and quantified include a downstream product of mRNA, such as a protein (e.g., a transcription factor). In general, as used herein, the term "gene transcript" may be used to denote any downstream product of gene transcription or translation, including post-translational modification, and "gene expression" may be used to refer generally to any measure of gene transcripts.

In some embodiments, the corresponding abundance of the respective cellular constituent is RNA abundance (e.g., gene expression), and the abundance of the respective cellular constituent is determined by measuring polynucleotide levels of one or more nucleic acid molecules corresponding to the respective gene. The transcript levels of the respective gene can be determined from the amount of mRNA, or polynucleotides derived therefrom, present in the respective cell in the first and/or second plurality of cells. Polynucleotides can be detected and quantitated by a variety of methods including, but not limited to, microarray analysis, polymerase chain reaction (PCR), reverse transcriptase polymerase chain reaction (RT-PCR), Northern blot, serial analysis of gene expression (SAGE), RNA switches, RNA fingerprinting, ligase chain reaction, Qbeta replicase, isothermal amplification method, strand displacement amplification, transcription based amplification systems, nuclease protection assays (Si nuclease or RNAse protection assays), and/or solid-state nanopore detection. See, e.g., Draghici, Data Analysis Tools for DNA Microarrays, Chapman and Hall/CRC, 2003; Simon et al., Design and Analysis of DNA Microarray Investigations, Springer, 2004; Real-Time PCR: Current Technology and Applications, Logan, Edwards, and Saunders eds., Caister Academic Press, 2009; Bustin A-Z of Quantitative PCR (IUL Biotechnology, No. 5), International University Line, 2004; Velculescu et al., (1995) Science 270: 484-487; Matsumura et al., (2005) Cell. Microbiol. 7: 11-18; Serial Analysis of Gene Expression (SAGE): Methods and Protocols (Methods in Molecular Biology), Humana Press, 2008; each of which is hereby incorporated herein by reference in its entirety.

In some embodiments, the corresponding abundance of the respective cellular constituent is obtained from expressed RNA or a nucleic acid derived therefrom (e.g., cDNA or amplified RNA derived from cDNA that incorporates an RNA polymerase promoter) from a respective cell in the first and/or second plurality of cells, including naturally occurring nucleic acid molecules, as well as synthetic nucleic acid molecules. Thus, in some embodiments, the corresponding abundance of the respective cellular constituent is obtained from such non-limiting sources as total cellular RNA, poly(A)+ messenger RNA (mRNA) or a fraction thereof, cytoplasmic mRNA, or RNA transcribed from cDNA (e.g., cRNA). Methods for preparing total and poly(A)+RNA are well known in the art, and are described generally, e.g., in Sambrook, et al., Molecular Cloning: A Laboratory Manual (3rd Edition, 2001). RNA can be extracted from a cell of interest using guanidinium thiocyanate lysis followed by CsCl centrifugation (see, e.g., Chirgwin et al., 1979, Biochemistry 18:5294-5299), a silica gel-based column (e.g., RNeasy (Qiagen, Valencia, Calif.) or StrataPrep (Stratagene, La Jolla, Calif)), or using phenol and chloroform, as described in Ausubel et al., eds., 1989, Current Protocols In Molecular Biology, Vol. III, Green Publishing Associates, Inc., John Wiley & Sons, Inc., New York, at pp. 13.12.1-13.12.5). Poly(A)+RNA can be selected, e.g., by selection with oligo-dT cellulose or, alternatively, by oligo-dT primed reverse transcription of total cellular RNA. RNA can be fragmented by methods known in the art, e.g., by incubation with ZnCl2, to generate fragments of RNA.

In some embodiments, the corresponding abundance of the respective cellular constituent in the respective cell in the first and/or second plurality of cells is determined by sequencing. In some embodiments, the corresponding abundance of the respective cellular constituent in the respective cell in the first and/or second plurality of cells is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combination thereof.

The cellular constituent abundance measurement technique can be selected based on the desired cellular constituent to be measured. For instance, scRNA-seq, scTag-seq, and miRNA-seq can be used to measure RNA expression. Specifically, scRNA-seq measures expression of RNA transcripts, scTag-seq allows detection of rare mRNA species, and miRNA-seq measures expression of micro-RNAs. CyTOF/SCoP and E-MS/Abseq can be used to measure protein expression in the cell. CITE-seq simultaneously measures both gene expression and protein expression in the cell, and scATAC-seq measures chromatin conformation in the cell. Table 1 below provides example protocols for performing each of the cellular constituent abundance measurement techniques described above.

TABLE 1

Example Measurement Protocols

| Technique | Protocol |
| --- | --- |
| RNA-seq | Olsen et al., (2018), "Introduction to Single-Cell RNA Sequencing," Current protocols in molecular biology 122(1), pg. 57. |
| Tag-seq | Rozenberg et al., (2016), "Digital gene expression analysis with sample multiplexing and PCR duplicate detection: A straightforward protocol," BioTechniques, 61(1), pg. 26. |
| ATAC-seq | Buenrostro et al., (2015), "ATAC-seq: a method for assaying chromatin accessibility genome-wide," Current protcols in molecular biology, 109(1), pg. 21. |
| miRNA-seq | Faridani et al., (2016), "Single-cell sequencing of the small-RNA transcriptome," Nature biotechnology, 34(12), pg. 1264. |
| CyTOF/ SCoPE-MS/ Abseq | Bandura et al., (2009), "Mass cytometry: technique for real time single cell multitarget immunoassay based on inductivitely coupled plasma time-of-flight mass spectrometry," Analystic chemistry, 81(16), pg. 6813. Budnik et al., (2018), "SCoPE-ME: mass scpectrometry of single mammalian cells quantifies proteome heterogenity during cell differentiation," Genome biology, 19(1), pg. 161. Shahi et al., (2017), "Abseq: Ultrahigh-throughoutput single cell protein profiling with droplep microfluidic barcoding," Scientific reports, 7, pg. 44447. |
| CITE-seq | Stoeckius et al., (2017), "Simultaneous epitope and transcritome measurement in single cells," Nature Methods, 14(9), pg. 856. |

In some embodiments, the plurality of cellular constituents is measured at a single time point. In some embodiments, the plurality of cellular constituents is measured at multiple time points. For instance, in some embodiments, the plurality of cellular constituents is measured at multiple time points throughout a cell state transition (e.g., a differentiation process, a response to an exposure to a compound, a developmental process, etc.).

It is to be understood that this is by way of illustration and not limitation, as the present disclosure encompasses analogous methods using measurements of other cellular constituents obtained from cells (e.g., single cells). It is to be further understood that the present disclosure encompasses methods using measurements obtained directly from experimental work carried out by an individual or organization practicing the methods described in this disclosure, as well as methods using measurements obtained indirectly, e.g., from reports of results of experimental work carried out by others and made available through any means or mechanism, including data reported in third-party publications, databases, assays carried out by contractors, or other sources of suitable input data useful for practicing the disclosed methods.

In some embodiments, the corresponding abundances for the plurality of cellular constituents in the first and/or the second plurality of cells (e.g., the one or more first datasets and/or the one or more second datasets) are preprocessed. In some embodiments, the preprocessing includes one or more of filtering, normalization, mapping (e.g., to a reference sequence), quantification, scaling, deconvolution, cleaning, dimension reduction, transformation, statistical analysis, and/or aggregation.

For example, in some embodiments, the plurality of cellular constituents is filtered based on a desired quality, e.g., size and/or quality of a nucleic acid sequence, or a minimum and/or maximum abundance value for a respective cellular constituent. In some embodiments, filtering is performed in part or in its entirety by various software tools, such as Skewer. See, Jiang, H. et al., BMC Bioinformatics 15(182):1-12 (2014). In some embodiments, the plurality of cellular constituents is filtered for quality control, for example, using a sequencing data QC software such as AfterQC, Kraken, RNA-SeQC, FastQC, or another similar software program. In some embodiments, the plurality of cellular constituents is normalized, e.g., to account for pull-down, amplification, and/or sequencing bias (e.g., mappability, GC bias etc.). See, for example, Schwartz et al., PLoS ONE 6(1):e16685 (2011) and Benjamini and Speed, Nucleic Acids Research 40(10):e72 (2012), the contents of which are hereby incorporated by reference, in their entireties, for all purposes. In some embodiments, the preprocessing removes a subset of cellular constituents from the plurality of cellular constituents. In some embodiments, the preprocessing the corresponding abundances for the plurality of cellular constituents improves (e.g., lowers) a high signal-to-noise ratio.

In some embodiments, the preprocessing comprises performing a comparison of a corresponding abundance of a respective cellular constituent in a respective cell to a reference abundance. In some embodiments, the reference abundance is obtained from, e.g., a normal sample, a matched sample, a reference dataset comprising reference abundance values, a reference cellular constituent such as a housekeeping gene, and/or a reference standard. In some embodiments, this comparison of cellular constituent abundances is performed using any differential expression test including, but not limited to, a difference of means test, a Wilcoxon rank-sum test (Mann Whitney U test), a t-test, a logistic regression, and a generalized linear model. Those of skill in the art will appreciate that other metrics are also possible for comparison and/or normalization of cellular constituent abundances.

Thus, in some embodiments, the corresponding abundance of a respective cellular constituent in a respective cell in the one or more first datasets and/or in the one or more second datasets comprises any one of a variety of forms, including, without limitation, a raw abundance value, an absolute abundance value (e.g., transcript number), a relative abundance value (e.g., relative fluorescent units, transcriptome analysis, and/or gene set expression analysis (GSEA)), a compound or aggregated abundance value, a transformed abundance value (e.g., log 2 and/or log 10 transformed), a change (e.g., fold- or log-change) relative to a reference (e.g., a normal sample, matched sample, reference dataset, housekeeping gene, and/or reference standard), a standardized abundance value, a measure of central tendency (e.g., mean, median, mode, weighted mean, weighted median, and/or weighted mode), a measure of dispersion (e.g., variance, standard deviation, and/or standard error), an adjusted abundance value (e.g., normalized, scaled, and/or error-corrected), a dimension-reduced abundance value (e.g., principal component vectors and/or latent components), and/or a combination thereof. Methods for obtaining cellular constituent abundances using dimension reduction techniques are known in the art and further detailed below, including but not limited to principal component analysis, factor analysis, linear discriminant analysis, multi-dimensional scaling, isometric feature mapping, locally linear embedding, hessian eigenmapping, spectral embedding, t-distributed stochastic neighbor embedding, and/or any substitutions, additions, deletions, modification, and/or combinations thereof as will be apparent to one skilled in the art. See, for example, Sumithra et al., 2015, "A Review of Various Linear and Non Linear Dimensionality Reduction Techniques," Int J Comp Sci and Inf Tech, 6(3), 2354-2360, which is hereby incorporated herein by reference in its entirety.

In some embodiments, the using the plurality of vectors to identify each candidate cellular constituent module in the plurality of candidate cellular constituent modules comprises application of a correlation model to the plurality of vectors using each corresponding plurality of elements of each vector in the plurality of vectors.

In some embodiments, the correlation model includes a clustering method (e.g., a clustering model). In some embodiments, the correlation model includes a graph clustering method (e.g., model) and/or a non-graph clustering method. In some embodiments, the graph clustering method is Leiden clustering on a Pearson-correlation-based distance metric. In some embodiments, the graph clustering method is Louvain clustering.

For example, in some implementations, the method comprises application of a correlation-based cost function. Optimizing a correlation-based cost function includes computing a nearest-neighbor graph defining neighborhood relations among cellular constituents (e.g., genes), representing each cellular constituent by a vector formed by storing the abundance counts (e.g., expression values) for the cellular constituent in each cell, and computing correlations among cellular constituents. Cellular constituents with high correlations among one another are determined to be nearest neighbors and are used to form a cellular constituent module by clustering the graph using a graph clustering method (e.g., Leiden and/or Louvain).

Any one of a number of clustering techniques can be used, examples of which include, but are not limited to, hierarchical clustering, k-means clustering, and density based clustering. In an embodiment, a hierarchical density based clustering is used (referred to as HDBSCAN, see, e.g., Campello et al., (2015). Hierarchical density estimates for data clustering, visualization, and outlier detection. *ACM Trans Knowl Disc Data*, 10(1), 5). In another embodiment, a community detection based clustering is used, such as Louvain clustering (see, e.g., Blondel et al., (2008). Fast unfolding of communities in large networks. *J stat mech: theor exp*, 2008(10), P10008). In yet another embodiment, Leiden clustering is used. The Leiden algorithm proceeds by moving individual nodes between communities to determine partitions, refining partitions, and creating aggregate networks based on the refined partitions. Aggregate networks are further partitioned based on the unrefined partitions determined in earlier steps of the process, and new partitions are refined by moving individual nodes within each aggregate network. See, e.g., Traag et al., (2019), "From Louvain to Leiden: guaranteeing well-connected communities," *Sci Rep* 9:5233, doi: 10.1038/s41598-019-41695-z. In still another embodiment, a diffusion path algorithm is used.

Generally, clustering such as Louvain clustering and/or Leiden clustering uses hard partitioning techniques, in which each element (e.g., each cellular constituent) is uniquely assigned to a single cluster without overlapping. However, and without being bound to any one particular theory, cellular processes (e.g., associated with a physiological condition of interest) may be characterized by complex and dynamic interactions between networks of cellular constituents within the cell, where a single gene, for instance, can play a role in two, three, four, or more cellular processes within a cell, in combination with any number of other genes that similarly function in any number of the same or different processes and pathways. Thus, in paralleling the complexity of intracellular activity, the clustering of cellular constituents into a first module need not necessarily be exclusive of any other module. In some embodiments, therefore, the identification of cellular constituent modules comprises obtaining modules with overlapping subsets of cellular constituents.

Alternatively or in addition to employing a hard partitioning technique using a correlation-based model, in some embodiments, the using the plurality of vectors to identify each cellular constituent module in a plurality of cellular constituent modules comprises a dictionary learning model that produces the representation of the plurality of cellular constituents as a plurality of dimension reduction components. In some embodiments, the dictionary learning model is L0-regularized autoencoder. An advantage of these models is that they do not enforce a 1:1 correspondence between modules and cellular constituents but allow cellular constituents to appear in several modules at the same time.

For example, in some implementations, the method comprises application of a spare autoencoder cost function. In some such instances, optimizing a sparse autoencoder cost function includes training a one-layer autoencoder with L0 regularization of its weights, and a reconstruction loss, using standard training as implemented in pytorch or tensorflow.

Other methods of overlapping partitioning algorithms are possible, including, but not limited to, fuzzy K-means, overlapping K-means (OKM), weighted OKM (WOKM), overlapping partitioning cluster (OPC), and multi-cluster overlapping K-means extension (MCOKE), and/or any variations or combinations thereof.

In some embodiments, statistical techniques can be used to compress high dimensional data (e.g., abundances of a plurality of cellular constituents across a plurality of cellular constituent modules, for each cell in the first plurality of cells collectively representing a plurality of annotated cell states) to a lower dimensional space, while preserving the shape of the latent information encoded in the one or more first datasets. For instance, as illustrated in the top panel of FIG. 4, a count matrix comprises, for each cell in the first plurality of cells, for each cellular constituent in the plurality of cellular constituents, a corresponding count (e.g., abundance). The count matrix can be transformed into the latent representation illustrated in the bottom panel of FIG. 4, where the data is reduced to a lower dimensional space representing the clustering of cellular constituents across the first plurality of cells, based on similarities of their corresponding abundances under conditions of different annotated cell states (e.g., cell types, exposure conditions, diseases, etc.). The clustered cellular constituents are thus represented as cellular constituent modules, which in the latent representation encode the similarity in behavior across the plurality of cell states.

Referring again to the latent representation illustrated in FIG. 4, the values in the entries at each row-column grouping are determined by the dimensionality reduction based on the original input datasets. For instance, each entry can include an indication of membership, for each respective cellular constituent represented by the respective column, in the subset of the plurality of cellular constituents included in the respective cellular constituent module represented by the respective row (e.g., $weight_{1\text{-}1}$, $weight_{1\text{-}2}$, etc.). In particular, in some embodiments, each entry is a weight indicating whether the respective cellular constituent is included in the respective module. In some implementations, a weight is a binary indication of membership (e.g., presence or absence in a respective module is indicated by a 1 or a 0, respectively). In some implementations, a weight is scaled to indicate a relative importance of a cellular constituent to a respective module (e.g., a probability of membership and/or a correlation).

In some embodiments, a respective dimension in the latent representation corresponds to a representation of a respective cellular constituent. Representations of cellular constituents can arise, for example, from nonlinear representations of cellular constituents, such as where a respective entry (e.g., weight) in a latent representation matrix corresponds to a plurality of cellular constituents. Other embodiments comprising representations of cellular constituent include latent representations obtained using principal component analysis, in which each principal component represent variance and/or other transformations of the data corresponding to the plurality of cellular constituents.

In some embodiments, dimensionality reduction techniques result in some lossy compression of the data. However, the resulting latent representation (e.g., latent representation 118) is smaller in computational storage size, and therefore requires less computing processing power to analyze in conjunction with other downstream techniques such as model training. The arrangement of the plurality of cellular constituent modules in a latent representation thus increases the computational feasibility of the presently disclosed method, using computing devices of the current era.

A variety of dimensionality reduction techniques may be used. In some embodiments, the dimension reduction is principal components (PCA), random projection, an independent component analysis, feature selection, factor analysis, Sammon mapping, curvilinear components analysis, stochastic neighbor embedding (SNE), an Isomap, maximum variance unfolding, locally linear embedding, t-SNE, non-negative matrix factorization, a kernel principal component analysis, a graph-based kernel principal component analysis, linear discriminant analysis (LDA), generalized discriminant analysis, uniform manifold approximation and projection (UMAP), LargeVis, a Laplacian Eigenmap, a diffusion map, a network (e.g., neural network) technique, and/or a Fisher's linear discriminant analysis. See, for example, Fodor, 2002, "A survey of dimension reduction techniques," Center for Applied Scientific Computing, Lawrence Livermore National, Technical Report UCRL-ID-148494; Cunningham, 2007, "Dimension Reduction," University College Dublin, Technical Report UCD-CSI-2007-7, Zahorian et al., 2011, "Nonlinear Dimensionality Reduction Methods for Use with Automatic Speech Recognition," Speech Technologies. doi:10.5772/16863. ISBN 978-953-307-996-7; and Lakshmi et al., 2016, "2016 IEEE 6th International Conference on Advanced Computing (IACC)," pp. 31-34. doi:10.1109/IACC.2016.16, ISBN 978-1-4673-8286-1, each of which is hereby incorporated by reference. Accordingly, in some embodiments, the dimension reduction is principal component analysis (PCA), and each respective extracted dimension reduction component comprises a respective principal component derived by PCA. In such embodiments, the number of principal components in the plurality of principal components can be limited to a threshold number of principal components calculated by PCA. The threshold number of principal components can be, for example, at least 5, at least 10, at least 20, at least 50, at least 100, at least 1000, at least 1500, or any other number. In some embodiments, each principal component calculated by PCA is assigned an eigenvalue by PCA, and the corresponding subset of the first plurality of extracted features is limited to the threshold number of principal components assigned the highest eigenvalues. For each respective cellular constituent vector in the plurality of cellular constituent vectors, the plurality of dimension reduction components are applied to the respective cellular constituent vector to form a corresponding dimension reduction vector that includes a dimension reduction component value for each respective dimension reduction component in the plurality of dimension reduction components. This forms, from the plurality of cellular constituent vectors, a corresponding plurality of dimension reduction vectors, thereby forming a plurality of cellular constituent modules arranged in a latent representation.

In some embodiments, the method further includes performing manifold learning using the plurality of cellular constituent modules arranged in a latent representation. Generally, manifold learning is used to describe the low-dimensional structure of high-dimensional data by determining maximal variations in a dataset. Examples include, but are not limited to, force-directed layout (Fruchterman, T. M., & Reingold, E. M. (1991). Graph drawing by force-directed placement. *Software: Practice and experience,* 21(11), 1129-1164) (e.g., Force Atlas 2), t-distributed stochastic neighbor embedding (t-SNE), locally linear embedding (Roweis, S. T., & Saul, L. K. (2000). Nonlinear dimensionality reduction by locally linear embedding. *Science,* 290(5500), 2323-2326), local linear isometric mapping (ISOMAP, Tenenbaum, J. B., De Silva, V., & Langford, J. C. (2000). A global geometric framework for nonlinear dimensionality reduction. *Science,* 290(5500), 2319-2323), kernel PCA, graph-based kernel PCA, Potential of Heat-Diffusion for Affinity Based Trajectory Embedding (PHATE), generalized discriminant analysis (GDA), Uniform Manifold Approximation and Projection (UMAP), or kernel discriminant analysis. Discriminant analysis may be used particularly where some information is known in advance as to the specific cell type of each cell. Force-directed layouts are useful in various particular embodiments because of their ability to identify new, lower dimensions that encode non-linear aspects of the underlying data which arise from underlying cellular processes. Force directed layouts use physics-based models as mechanisms for determining a reduced dimensionality that best represents the data. As an example, a force directed layout uses a form of physics simulation in which, in this embodiment, each cell in the one or more first datasets is assigned a "repulsion" force and there exists a global "gravitation force" that, when computed over the first plurality of cells, identifies sectors of the data that "diffuse" together under these competing "forces." Force directed layouts make few assumptions about the structure of the data, and do not impose a de-noising approach.

Manifold learning is further described, for example, in Wang et al., 2004, "Adaptive Manifold Learning," Advances in Neural Information Processing Systems 17, which is hereby incorporated herein by reference in its entirety.

In some embodiments, the plurality of covariates comprises cell batch, cell donor, cell type, disease status, or exposure to a chemical compound. In some embodiments, the plurality of covariates comprises one or more indications of time points, replicates, and/or relevant metadata related to one or more cells in the second plurality of cells. In some embodiments, the plurality of covariates comprises experimental data (e.g., flow cytometry readouts, imaging and microscopy annotations, cellular constituent data, etc.). In some embodiments, the plurality of covariates comprises one or more genetic markers characteristic of one or more cells in the second plurality of cells (e.g., copy number variations, single nucleotide variants, multiple nucleotide polymorphisms, insertions, deletions, gene fusions, microsatellite instability status, amplifications, and/or isoforms). In some embodiments, the plurality of covariates comprises one or more of a cell phenotype, cellular behavior, disease state, genetic mutation, perturbations of genes or gene products (e.g., knockdowns, silencing, overexpression, etc.), and/or exposure condition for one or more cells in the second plurality of cells.

For example, in some embodiments, a covariate is an exposure or a response to an exposure of a cell in the second plurality of cells to a compound under an exposure condition. In some embodiments, an exposure of a cell includes any treatment of the cell with one or more compounds. In some embodiments, the one or more compounds includes, for example, a small molecule, a biologic, a therapeutic, a protein, a protein combined with a small molecule, an ADC, a nucleic acid (e.g., an siRNA, interfering RNA, cDNA over-expressing wild-type and/or mutant shRNA, cDNA over-expressing wild-type and/or mutant guide RNA (e.g., Cas9 system or other cellular-component editing system), etc.), and/or any combination of any of the foregoing. In some embodiments, the exposure condition is a duration of exposure, a concentration of the compound, or a combination of a duration of exposure and a concentration of the compound.

In some embodiments, a covariate is a compound applied to one or more cells that induces a cell state transition and/or a perturbation signature in the one or more cells (e.g., a perturbagen).

In some embodiments, a covariate is a knowledge term (e.g., an annotation) associated with a cellular constituent in the plurality of cellular constituents, or with a cell in the second plurality of cells. For instance, in some embodiments, a covariate is a genome-wide association study (GWAS) annotation, a gene set enrichment assay (GSEA) annotation, a gene ontology annotation, a functional and/or signaling pathway annotation, and/or a cellular signature annotation. In some embodiments, a covariate is obtained from any public knowledge database known in the art, including, but not limited to, NIH Gene Expression Omnibus (GEO), EBI ArrayExpress, NCBI, BLAST, EMBL-EBI, GenBank, Ensembl, the KEGG pathway database, and/or any disease-specific database. In some embodiments, a covariate is obtained from a database providing perturbation (e.g., small-molecule) induced gene expression signatures, such as the Library of Integrated Network-based Cellular Signatures (LINCS) L1000 dataset. See, e.g., Duan, 2016, "L1000CDS$^2$: An ultra-fast LINCS L1000 Characteristic Direction Signature Search Engine," Systems Biology and Applications 2, article 16015, which is hereby incorporated herein by reference in its entirety.

In some embodiments, the plurality of covariates comprises at least 3, at least 5, at least 10, at least 15, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, or at least 3000 covariates. In some embodiments, the plurality of covariates comprises no more than 5000, no more than 1000, no more than 500, no more than 200, no more than 100, no more than 50, or no more than 20 covariates. In some embodiments, the plurality of covariates comprises from 3 to 10, from 10 to 50, from 20 to 500, from 200 to 1000, or from 1000 to 5000 covariates. In some embodiments, the plurality of covariates falls within another range starting no lower than 3 covariates and ending no higher than 5000 covariates.

In some embodiments, each covariate in the plurality of covariates is a compound applied to one or more cells that induces a cell state transition and/or a perturbation signature, and the plurality of covariates is a plurality of compounds. In some embodiments, the plurality of covariates consists of the plurality of compounds, as disclosed in the section entitled, "Compounds," above.

FIG. 5 illustrates an example activation data structure formed by combining the cellular constituent count data structure (e.g., obtained using the second plurality of cells collectively representing the plurality of covariates informative of the physiological condition of interest) and the latent representation using the plurality of cellular constituents or the representation thereof as a common dimension. To accomplish this, in some embodiments, a count matrix for the second plurality of cells (e.g., similar in structure to the count matrix for the first plurality of cells illustrated in FIG. 4) and the latent representation are multiplied together, such that the weights of the latent representation matrix are multiplied by the normalized counts of the count matrix. Generally, two matrices can be multiplied together by a common dimension (e.g., the x-axis of a first matrix and the y-axis of a second matrix). Matrix multiplication of the first and second matrices by their common dimension yields a third matrix of auxiliary data that can be applied, alternatively or in addition to the first matrix and/or the second matrix, to an untrained or partially trained model.

Thus, in some such embodiments, the count matrix has the dimensions n_cells×n_genes, and the latent representation has the dimensions n_genes×n_modules, where n_cells is the number of cells in the second plurality of cells, n_genes is the number of cellular constituents (e.g., genes), or the representation thereof, in the plurality of cellular constituents, and n_modules is the number of modules in the plurality of cellular constituent modules. This maps the abundances of the cellular constituents in the count matrix into a space in which each cell (e.g., corresponding to one or more covariates of interest) is characterized by its module activations, and in which the resulting matrix representation (e.g., the activation data structure) has dimensions n_cells× n_modules (e.g., after multiplying by a common dimension of n_genes).

Combination of the latent representation and the cellular constituent count data structure using, e.g., matrix multiplication, and the resulting activation data structure in matrix form, are collectively illustrated in FIG. 5. The latent representation (illustrated in the top panel of FIG. 5) has the dimensions Z×K, where Z is the number of cellular constituents or the representation thereof and K is the number of cellular constituent modules. The cellular constituent count data structure (illustrated in the lower left panel) has the dimensions G×Z, where G is the number of cells in the second plurality of cells and, as for the latent representation, Z is the number of cellular constituents or the representation thereof. Combination by matrix multiplication, using Z (the number of cellular constituents or the representation thereof) as a common dimension, generates the resulting activation data structure having dimensions G×K. Each entry for each respective column in each respective row is an activation weight indicating the activation of each respective cellular constituent module in the respective cell in the second plurality of cells corresponding to the respective column. Thus, as illustrated in FIG. 5, the counts corresponding to module 1 includes activation weight$_{1-1}$ corresponding to cell 1, activation weight$_{1-G}$ corresponding to cell G, and so on.

In some embodiments, the plurality of activation weights in the activation data structure comprises differential module activations. In some embodiments, differential module activations (e.g., differential activation weights of a respective module between cells in the second plurality of cells in the activation data structure) are obtained by computing v-scores using the function (mu_1−mu_2)/(var_1+ var_2)$^{-0.5}$, where mu_i denotes means of module activations across cells with a respective condition i (e.g., covariate i), and var_i denotes the variance of module activation in condition i. V-scores can be described as t-scores that are not normalized by the number of cells in the denominator.

In some embodiments, each respective cell in the second plurality of cells in the activation data structure represents a respective covariate. In some embodiments, each respective cell in the second plurality of cells in the activation data structure represents a respective compound applied to one or more cells that induces a cell state transition and/or a perturbation signature.

Thus, in some embodiments, the activation data structure indicates the activations (e.g., the level or degree of activation) of a respective cellular constituent module corresponding to (e.g., correlated to and/or in response to) an exposure to each compound in the plurality of compounds represented by the second plurality of cells. For instance, in some embodiments where each respective cell in the second plurality of cells represents a respective perturbagen (e.g., a compound to which one or more cells are exposed and/or a compound that induces a cell state transition and/or a perturbation signature), the activation data structure includes a respective activation weight, for each respective cellular constituent module in the plurality of cellular constituent modules, indicating the activation (e.g., inducement and/or differential expression) of the respective cellular constituent module, correlating to and/or in response to treatment with the respective compound.

In some embodiments, the candidate cellular constituent model comprises any of the model architectures disclosed herein, as described in the section entitled "Model architectures," above.

In some embodiments, the candidate cellular constituent model is an autoencoder, a sparse autoencoder, and/or a sparse multi-readout, knowledge-coupled autoencoder. In some embodiments, the candidate cellular constituent model is a semi-supervised model. In some embodiments, the candidate cellular constituent model is a one-layer neural network (e.g., a SoftMax and/or logistic regression model). In some embodiments, the candidate cellular constituent model is a one-dimensional Huber Outlier Regressor model.

In some embodiments, the candidate cellular constituent model is a sparse multi-readout, knowledge-coupled autoencoder comprising a plurality of layers, where the first layer is used to obtain the latent representation and the second layer is used to obtain the cellular constituent module knowledge construct (e.g., a covariate weight matrix).

In some embodiments, the training the candidate cellular constituent model is performed using a categorical cross-entropy loss in a multi-task formulation, in which each covariate in the plurality of covariates corresponds to a cost function in plurality of cost functions and each respective cost function in the plurality of cost functions has a common weighting factor.

In some embodiments, training the candidate cellular constituent model trains the model to identify the first cellular constituent module in the set of cellular constituent modules that is associated with the physiological condition of interest. Methods for training models are described in further detail herein. Any of the methods and/or embodiments disclosed herein are contemplated for use in training the candidate cellular constituent model, as described in the section entitled "Model training," above.

V. EXAMPLES

Provided herein are example performance measures and therapeutic applications of models for associating compounds with physiological conditions.

Example 1. Predicting Chemical Structure for Activation of Fatty Acid-Related Cellular Processes In this example, cellular constituent modules were first defined. This was done by obtaining expression data for cells where the cells represented different states associated with a physiological condition of interest. This tracks claim 27 as originally filed. Cellular constituent abundance values are measured from each of the cells and this data is used to cluster the cellular constituents. Those cellular constituents whose expression values are correlated with each other across the various states represented by the cells are grouped into cellular constituent modules. This results in several cellular constituent modules, each of which includes a different subset of the cellular constituents samples. In some embodiments, while each cellular constituent module has a different subset of cellular constituents, it is possible that there is overlap between the cellular constituents in one cellular constituent module and the cellular constituents in another cellular constituent module.

Further in the example, additional training data is obtained in the form of a second training set. This second training set also comprises single cell abundance data for cellular constituents. However, in this second training set, each cell has been exposed to a different chemical compound in a plurality of training chemical compounds. In this training set, the known quantities are the fingerprints of the respective different chemical compounds, and the resulting cellular constituent abundance data of cells exposed to such compounds. The data for the second dataset can be arranged as count matrix 502 (illustrated in FIG. 5), with a first axis for cellular constituent identity and a second axis for cell identity. Thus, each element in count matrix 502 is the abundance of a given cellular constituent in a given cell. Moreover, each respective column in count matrix 502 (which corresponds to a particular cell) is labeled with the particular compound to which the particular cell was exposed. Thus, each column of count matrix 502 is labeled with a particular compound (e.g., training compound), while each element is the count of a corresponding cellular constituent (Y-axis) for a corresponding cell (X-axis).

As illustrated in FIG. 5, the data from the first dataset (latent representation 404) and the second dataset (count matrix 502) is combined to form an activation data structure (e.g., activation data structure 504 as illustrated in FIG. 5). For instance, one way to accomplish this is to arrange the cellular constituent modules as rows in latent representation 404 so that a first axis represents cellular constituent modules and a second axis represents each of the cellular constituents. In this way, to produce activation data structure 504, the latent representation 404 and the count matrix 502 are multiplied by their common axis, cellular constituent number, via matrix multiplication to arrive at the activation data structure 504. Activation data structure 504 retains the cell identity axis from the count matrix 502 and the cellular constituent module axis from the latent representation 504. Different activation structures can be formed for different cell types. That is, the cells used to form count matrix 502 can represent a particular disease state of interest. Thus, different activation data structures 504 can be formed for different disease states or other phenotypes of interest.

Turning to FIG. 6, in some instances, each row of activation data structure 504 (from FIG. 5 and now at the top of FIG. 6) serves as training data for a different model 601. For instance, consider the case where model 601 includes the weights of row 604-1 (Weight$_{1-1}$ through Weight$_{1-W}$) to represent the extent to which compound 1 through W respectively activate cellular constituent module 1. This model 601 is trained on the elements of row 640 of activation data structure 504, which provide the extent to which each of the training compounds 1, . . . , G activate cellular constituent module 1. In this training, first a fingerprint representation of the compound that cell 1 was exposed to is inputted into the model 601. Responsive to this input, the model 601 for cellular constituent module 1 outputs an activation value, termed Pred. Value$_1$ in the nomenclature of FIG. 6. This output activation value is compared to the actual activation value, which is Act$_{1-1}$ of activation data structure 504. Next, a fingerprint representation of the compound that cell 2 was exposed to is inputted into the model 601. In response to this input, the model outputs an activation value (Pred. Value$_2$). This output activation value is compared to the actual activation value for compound 2, which is Act$_{1-2}$ of activation data structure 504. This process proceeds through cell G. A fingerprint representation of the compound that cell G was exposed to is inputted into the model 601. In response to this, the model will output an activation value (Pred. Value$_G$). This output activation value is compared to the actual activation value for cell G, which is Act$_{1-G}$ of activation data structure 504. In this example, W and G have the same value. In this way, there is a resulting prediction (Pred. Value) for each compound in the training set of compounds used to derive the activation data structure as outlined in FIG. 5 for cellular constituent module 1. The above-described calculated predictions (of the activation value) are compared to the above-described actual activation values for each of these compounds and the differences between the predicted and actual activation values are used to further train the model 601 using back-propagation and related model refinement techniques.

Thus, the result is a series of trained models 601, one for each cellular constituent module. A fingerprint of a test compound can be inputted into each of the trained models and each respective trained model 601 outputs a predicted activation value, the magnitude of which indicates whether the cellular constituent module corresponding the respective trained model is activated by the test compound. Now that an overview of the process has been described, each of the steps is described in conjunction with the experimental data used in this example.

Identify a first cellular constituent module (FIG. 1, FIG. 4 132-1) by the following process. Obtain one or more first datasets in electronic form. The one or more first datasets comprise data for a first plurality of cells (e.g., twenty or more cells) that collectively represent a plurality of annotated (e.g, labeled or known) cell states. The first dataset comprises, for each respective cell in the first plurality of cells, for each respective cellular constituent in a plurality of cellular constituents (e.g., 10 or more cellular constituents): a corresponding abundance of the respective cellular constituent in the respective cell. For instance transcriptional data for each cell. In this way a plurality of vectors is accessed or formed. Each respective vector in the plurality of vectors corresponds to a respective cellular constituent in the plurality of constituents and comprises a corresponding plurality of elements. Each respective element in the corresponding plurality of elements of a vector has a corresponding count representing the corresponding abundance of the respective cellular constituent in the respective cell in the first plurality of cells. Thus, in some such embodiments, transcriptional data for each cell state in a plurality of cells states is obtained.

To illustrate, a count matrix 402 of the form illustrated in FIG. 4 is formed. For this example, a small molecule perturbagen known to induce metabolically active processes in preadipocytes was used. Aliquots of preadipocyte cell line were exposed to the perturbagen for 24 hours and scRNA-seq readouts were obtained for the exposed aliquots of the cell line in the perturbed condition. scRNA-seq readouts were also obtained for aliquots of the cell line that has not been exposed to the perturbagen and these readouts represent the control condition. In this way, in accordance with block 1504 of FIG. 14A, a first dataset was obtained that comprised, for each respective cell in a first plurality of cells, for each respective cellular constituent in a plurality of cellular constituents, a corresponding abundance of the respective cellular constituent in the respective cell, thereby accessing or forming a plurality of vectors. That is, the expression values of each cellular constituent (e.g., gene) measured in both the cells that were exposed to the perturbagen and the cells that were not exposed to the perturbagen (control cells) formed the elements of a count matrix 402 illustrated in FIG. 4. As illustrated in FIG. 4 and noted in Block 1510 of FIG. 14A, the count matrix 402 includes a vector for each cellular constituent and thus there are a plurality of vectors. Each respective vector in the plurality of vectors (i) corresponds to a respective cellular constituent in the plurality of constituents and (ii) comprises a corresponding plurality of elements.

For instance, for the cellular constituent 1 (e.g., gene 1), the counts 1-1, . . . , counts 1-N, are the measurement of the expression of gene 1 in cells 1 through N, where some of the N cells have been exposed to the perturbagen and some have not, and these counts form the elements of the vector for cellular constituent 1. That is, in accordance with Block 1512 of FIG. 14A, each respective element in the corresponding plurality of elements of the vector for cellular constituent 1 has a corresponding count representing the corresponding abundance of the respective cellular constituent in the respective cell in a first plurality of cells. While this example includes two states (exposed to the perturbagen or not), in principal any number of states could be encompassed, such as different concentrations of perturbagen, exposure times, and the like.

In accordance with Block 1514 of FIG. 14A, there are two annotated states in this Example 1: control (no exposure to the perturbagen) and exposure of the perturbagen. That is, one annotated cell state in the plurality of annotated cell states is an exposure of a cell in the first plurality of cells to a compound (here, the perturbagen) under an exposure condition (e.g., a duration of exposure, here 24 hours). While this example consist of two states (exposed to the perturbagen or not), in principal any number of states could be encompassed, such as different concentrations of perturbagen, exposure times, and the like.

The count matrix 402 was pre-processed through filtering and normalization steps resulting in a pre-processed count matrix that contained several genes with a high signal-to-noise ratio.

Use the plurality of vectors to identify each candidate cellular constituent module in a plurality of candidate cellular constituent modules. Each candidate cellular constituent module in the plurality of candidate cellular constituent modules includes a subset of the plurality of cellular constituents. The plurality of cellular constituent modules are arranged in a latent representation dimensioned by (i) the plurality of candidate cellular constituent modules and (ii) the plurality of cellular constituents or a representation thereof and where the plurality of cellular constituent modules comprises more than ten cellular constituent modules.

In some embodiments, each candidate cellular constituent module is a candidate transcriptional fingerprint.

In this example, the count matrix 402 was used to identify cellular constituent modules 132. This was done in accordance with Block 1526 of FIG. 14B: use the plurality of vectors (each row of the count matrix 402 of FIG. 4) to identify each candidate cellular constituent module in a plurality of candidate cellular constituent modules, each candidate cellular constituent module in the plurality of candidate cellular constituent modules including a subset of the plurality of cellular constituents.

This resulted in a latent representation dimensioned by (i) the plurality of candidate cellular constituent modules and (ii) the plurality of cellular constituents or a representation thereof, where the plurality of candidate cellular constituent modules comprises more than ten cellular constituent modules. An example of this latent representation is latent representation 404 of FIG. 4, where, for each respective candidate cellular constituent module 132 there is an indication of which cellular constituents are in the respective candidate cellular constituent module.

The latent representation 404 was formed in accordance with block 1528 of FIG. 14C: the plurality of vectors (the cellular constituent vectors of the count matrix 402) were used to identify each candidate cellular constituent module in the plurality of candidate cellular constituent modules (of latent representation 404) by application of a correlation model to the plurality of vectors using each corresponding plurality of elements of each vector in the plurality of vectors. In particular, a correlation-based cost function was optimized, which amounted to computing a nearest-neighbor graph defining neighborhood relations among the cellular constituent vectors, and computing correlations among the cellular constituent vectors of count matrix 402. Cellular constituents (here genes) with a high correlation with each other across the plurality of cells ended up being nearest neighbors, and formed a cellular constituent module within the latent representation 402 by clustering the graph using Leiden or any other graph clustering method. Optimizing the sparse autoencoder cost function amounted to training a one-layer autoencoder with L0 regularization of its weights, and a reconstruction loss, using standard training as implemented in pytorch or tensorflow). In this example, this resulted in 108 cellular constituent modules being learned during training. That is, the latent representation 404 of FIG. 4 had 108 cellular constituent modules 132, each with an independent subset of the cellular constituents for which expression data was available in count matrix 402.

Of the 108 cellular modules, a cellular constituent module 132 termed "Module 78" displayed the strongest activation when averaging t-scores for each cellular constituent, computed across perturbed and control samples. In other words, the expression data in the count matrix data was used to validate the cellular constituents by performing, for each respective cellular constituent module in the latent representation 404, a t-score on the differential expression of each cellular constituent in the respective cellular constituent module between the cells that had been exposed to the perturbagen and the cells that had not been exposed to the perturbagen. Moreover, Module 78 is enriched with cellular constituents implicated in fatty-acid and lipid associated biological processes. In sum, Module 78 consists of 28 genes, including FABP3, a marker of metabolic activity.

In addition to the cellular constituent modules, what is needed is cell based cellular constituent response data upon exposure of cells to training compounds.

Thus, one or more second datasets was obtained in electronic form. The one or more second datasets comprises data from a second plurality of cells. The second plurality of cells comprises twenty or more cells. The second plurality of cells collectively represented a plurality of covariates informative of the physiological condition of interest. For instance, the plurality of covariates is training compounds in some instances. Then, for each cell in the second plurality of cells, for each respective cellular constituent in the plurality of cellular constituents: a corresponding abundance of the respective cellular constituent in the respective cell is acquired, thereby obtaining a cellular constituent count data structure dimensioned by (i) the second plurality of cells and (ii) the plurality of cellular constituents or the representation thereof.

This is in accordance with block 1538 of FIG. 14C, which states that a second dataset was obtained in electronic form comprising, for each respective cell in a second plurality of cells, where the second plurality of cells comprises twenty or more cells and collectively represents a plurality of covariates (here a plurality of different chemical compounds) informative of the physiological condition of interest: for each respective cellular constituent in the plurality of cellular constituents: a corresponding abundance of the respective cellular constituent in the respective cell, thereby obtaining a cellular constituent count data structure dimensioned by (i) the second plurality of cells and (ii) the plurality of cellular constituents or the representation thereof.

An illustration of the form of this count matrix is count matrix 502 of FIG. 5. As illustrated in count matrix 502 of FIG. 5, for each respective cellular constituent (e.g., gene), there is expression data for each cell in the second plurality of cells. For instance, the transcriptional activity of each of a plurality of genes is measured across the second plurality of cells. Each of the cells has been exposed to a covariate, here a training chemical compound.

Form an activation data structure by combining the cellular constituent count data structure and the latent representation using the plurality of cellular constituents or the representation thereof as a common dimension, where the activation data structure comprises, for each cellular constituent module in the plurality of cellular constituent modules, for each cell in the second plurality of cells, a respective activation weight.

Count matrix 502 was matrix multiplied by the latent representation 404 to obtain the activation data structure 504 illustrated in FIG. 5. The activation data structure 504 has, for each respective cellular constituent module, for each cell in the second plurality of cells, an activation value $Act_{K-G}$, the value of which is determined by the corresponding matrix multiplication of latent representation 404 by count matrix 502.

Train a candidate cellular constituent model using a difference between (i) a prediction of an absence or presence of each covariate in the plurality of covariates in each cellular constituent module represented in the activation data structure upon input of the activation data structure into the candidate model and (ii) actual absence or presence of each covariate in each cellular constituent module, where the training adjusts a plurality of covariate weights associated with the candidate cellular constituent model responsive to the difference.

Activation data structure 502 served as the training data (label data) for model 601 of FIG. 6, which is itself a latent representation 602 of dimensions N compounds×M cellular constituent modules. In this example, 8000 different compounds and 108 cellular constituent modules were considered. Thus, in the nomenclature of FIG. 5, Z was 108 and G was 8000. The activation data structure was split into a training and a test set in two ways. First, a "random split" was chosen which grouped 1200 compounds into a test set and the remaining 6800 compounds into a training set. Also, a "cross-scaffold split" was defined using functions in the open-source software package RDKit that ensure that the test set contains compounds with different scaffolds than the training set.

As illustrated in FIG. 6, each respective row of activation data structure 504 is a vector that represents which compounds likely induces the cellular constituents of the corresponding cellular constituent module represented by the respective row. Each instance of model 601 was trained on a row of activation data structure 504. Activation data structure 504 was formed using the 6800 training compounds. For a given model 601, the fingerprint of a particular chemical compound is inputted into the model 601 and, responsive to this input, a predicted activation values for the corresponding cellular constituent module is computed. This predicted activation value can be directly compared to the actual activation value in the corresponding element in activation data structure 504. Thus, in this way, a difference between (i) a prediction of an absence or presence of each compound in the training compounds for each cellular constituent module represented in the activation data structure 504 upon input of the activation data structure 504 into model 601 and (ii) actual absence or presence of each compound, for each cellular constituent module can be computed and used to train the model 601 by adjusting the plurality of covariate weights 604 associated with the candidate cellular constituent model responsive to the difference. As illustrated in FIG. 6, the plurality of covariate weights comprises, for each respective cellular constituent module in the plurality of cellular constituent modules: for each respective covariate: a corresponding weight indicating whether the respective covariate correlates, across the activation data structure, with the respective cellular constituent module. In some embodiments, there was a different model 601 for each cellular constituent module. In other words, referencing FIG. 6, in some embodiments, each row 604 is in a different model 601. Thus, in such embodiments, each such model 601 is trained using the corresponding row in the activation data structure (e.g., the row that corresponds to the same cellular constituent module as the respective model 601).

As illustrated in FIG. 6, the trained model 601 (or models) offers weights for each covariate (here training chemical compositions). That is, latent representation 602 of model 601 provides a weight (e.g., $weight_{1-1}$ or row 604-1 of FIG. 6) describing how much each covariate (chemical composition) associates with the activation of a cellular constituent module. Such weights are considered the respective numerical activation scores of the respective cellular constituent modules for the respective compound in the set of cellular constituent modules. In embodiments where a different model 601 is formed for each cellular constituent module, the latent representation 602 is the aggregate latent representation of each model 601. In some embodiments, each weight in representation is categorical (e.g., compound affects the cellular constituent module "0" or compound does not affect the cellular constituent module "1". In other embodiments, each weight is on a continuous scale where one end of the scale indicates the training compound greatly affects the cellular constituent module and the other end of the scale indicates the training compound does not affect the cellular constituent module. As used here, the term "affect" is application dependent, but generally means that absence or presence of the compounds changes the abundance of the cellular constituents in the cellular constituent module.

For training of the model 601, in this example, the SMILES representations of compounds represented in activation data structure 504 of FIG. 6 are transformed into an ECFP4 fingerprint representation, and additionally a graph representation. Subsequentially two models are trained. That is, the model 601 is an ensemble of two different models in this example: A) a fully connected neural network architecture is used to train on ECFP4 representation, B) a message-passing neural network (MPNN) is used to train on graph representations. Open source software packages pytorch and DGL were used to perform this training. The untrained model 601 is trained using, for each respective chemical structure of each respective compound in the training set, for each respective cellular constituent module in the set of cellular constituent modules, a respective difference between: (i) a respective calculated activation score for the respective cellular constituent module upon input of the fingerprint of the chemical structure of the respective compound into the untrained model and (ii) the respective numerical activation score of the respective cellular constituent module for the respective compound in the set of cellular constituent modules (obtained from the activation data structure 504), where the training adjusts a plurality of parameters associated with the untrained model 601 responsive to the difference, and where the plurality of parameters comprises 100 or more parameters, thereby obtaining a trained model.

As noted above, in this example, model 601 is an ensemble of (i) a fully connected network on standard fingerprints of the SMILES strings, where the network architecture is a 3-layer network with ReLU activations and (ii) an MPNN network out of the DGL library. Upon input of the chemical structural information, model 601 provides the activation score of each cellular constituent module 132 that it was trained on.

In fact, in some embodiments, there is a separate ensemble model 601 for each cellular constituent module in this example. In other words, the model 601 was a multi-task encoder that provides separate activation scores for each of a plurality of cellular constituent modules upon input of a chemical structure. Further still, in some embodiments, as discussed above, there is a separate model 601 for each respective cellular constituent module. In such embodiments, each such respective model 601 includes the activations weight for each compound with respect to a corresponding cellular constituent model.

Each respective model 601, now trained, provides an activation score for its corresponding cellular constituent module, for any compound, whether part of the training set or not. That is, each model 601 is capable of reporting out whether its corresponding cellular constituent module is associated with a test compound. If it is, the model outputs a score that indicates that its corresponding cellular constituent module is associated with a test compound. In some embodiments, this score is categorical (e.g. a "1" if the corresponding cellular constituent module is associated with a test compound" and a "0" if it is not). In some embodiments, this score is a probability or likelihood, e.g., on a scale of 0 to 1 where numbers closer to 1 (e.g., 0.85) indicate the likelihood that the corresponding cellular constituent module is associated with a test compound. In some embodiments, this score is on a continuous scale in a between "A" to "B", where A and B are two different numbers. Since there are several models 601, each corresponding to a different cellular constituent module, the test compound is run against several different models 601 to determine which cellular constituent modules are activated by (associated with) the compound. In each instance, the chemical structure is converted to a fingerprint as discussed above and it is this fingerprint that is applied to each model. Note, from a biological perspective, it can be expected that a given test compound may activate any number of different cellular constituent modules (e.g., 1, 2, 3, 4, 5, or more). Moreover, the approach described in the present disclosure can be validated by testing compounds that the models 601 have not been trained on, but for which it is known which cellular constituent modules should be activated by the test compounds. That was done in this example as set forth below. In particular, the trained models 601, for associating compounds with physiological conditions, was validated 4-fold in this example. This testing tracks claim 1 as originally filed.

Figure 10A:
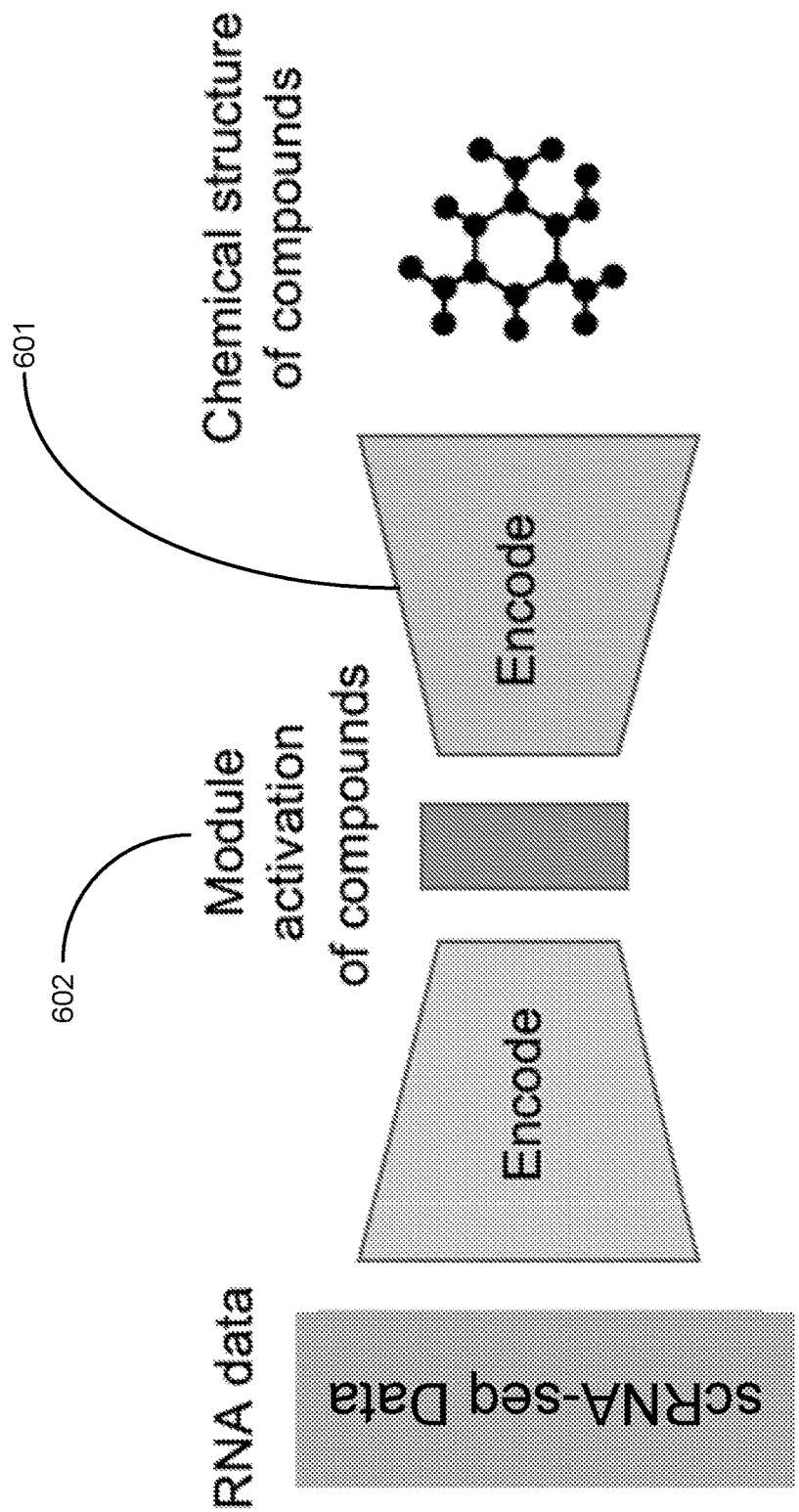
Figure 10B:
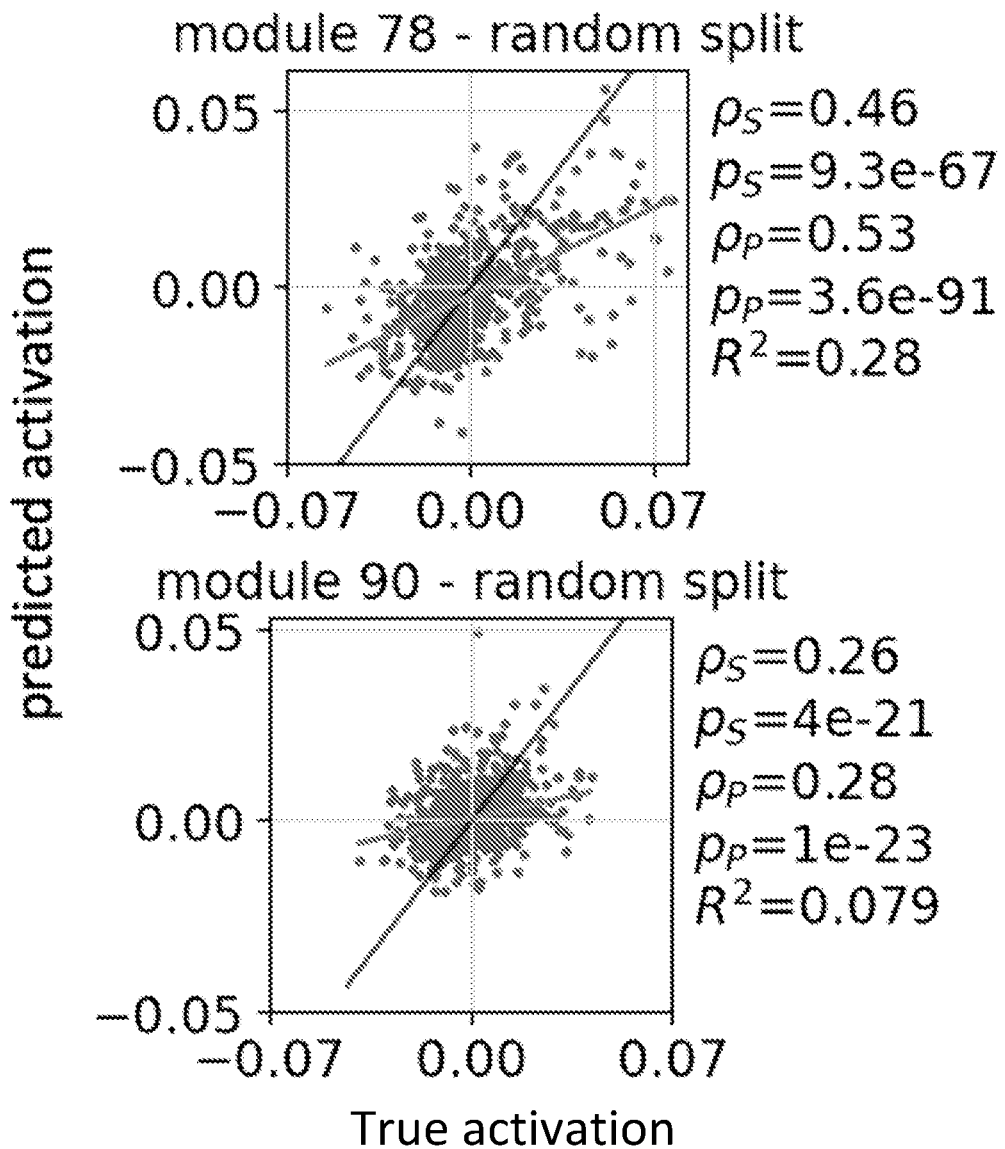

First, model predictions from models 601 were obtained for the activation of fatty acid generation-related cellular constituent modules induced by the above-described 1200 randomly selected unseen compounds from a high-throughput screen, and by the above described 1200 compounds with non-overlapping scaffolds to the 6800 compound training set. Respective model 601 predictions (predicted cellular constituent activation scores) obtained for randomly selected compounds are illustrated in FIG. 10B. That is, FIG. 10B shows the results from two different models 601, one for cellular constituent module 78 "Module 78" and one for cellular constituent module "90". Module 78 represents a fatty acid-related cellular process important for cellular metabolism, and its corresponding trained model 601 exhibited a high coefficient of determination ($R^2=0.28$). In contrast, the trained model 601 for the cellular constituent 'Module 90," which is unrelated to a cellular metabolism (the cellular constituents in Module 90 do not relate to a fatty acid-related process), learned from the same scRNA-seq dataset, had a low coefficient of determination ($R^2=0.08$). All benchmarks yielded highly significant correlation (Pearson correlation coefficient $p_s$=~0.5 and ~0.2, respectively).

In the language of claim 1 as originally filed, this first validation approach provides a method of associating a test chemical compound (one of the described 1200 randomly selected unseen compounds from a high-throughput screen, and by the above described 1200 compounds with non-overlapping scaffolds to the 6800 compound training set) with a physiological condition of interest (here, in this example, a fatty acid-related cellular process important for cellular metabolism). The method comprises, at a computer system comprising a memory and one or more processors, obtaining a fingerprint of a chemical structure of the test chemical compound. Thus, a fingerprint of a chemical structure of the test chemical compound is obtained and that is what is inputted into each model 601 of FIG. 1 in this example. In the context of claim 1 as originally filed, the model is referred to as a model. This model encompasses an ensemble model, in which each component model in the ensemble model includes a single row of the parameters listed for model 601 of FIG. 6, the row being the parameters for the weights for the given cellular constituent module associated with the component model. It will be appreciated that while in FIG. 6 such weights are represented as a single row, there is no requirement that they be in row format in the component model of the ensemble model, any equivalent thereof is within the scope of the present disclosure. Moreover, while model 601 of FIG. 6 includes a single weight for each compound it was trained against, which is suitable in models 601 based on regression, in some embodiments there is no clear relationship between the number of weights in the model 601 and the number of compounds a model was trained against. In some embodiments, the model 601 includes 100 or more, 1000 or more, 10,000 or more, or 100,000 or more parameters.

In accordance with claim 1 as originally filed, the fingerprint of the test compound is inputted into the model. As noted in claim 1 as originally filed, the model comprises 100 or more parameters. In other words, the calculation of the model output, upon inputting the fingerprint of the test compound, cannot be mentally performed. The model outputs one or more calculated activation scores responsive to the inputting of the fingerprint into the model. Each respective calculated activation score in the one or more calculated activation scores represents a corresponding cellular constituent module in a set of cellular constituent modules. In this example, the model is an ensemble of models 601, each representing a different cellular constituent module and thus each model 601 in the ensemble outputs a calculated activation score in the one or more calculated activation scores representing a single corresponding cellular constituent module in a set of cellular constituent modules. In this regard, and as noted above, each respective cellular constituent module in the set of cellular constituent modules includes an independent subset of a plurality of cellular constituents. Moreover, at least a first cellular constituent module in the set of cellular constituent modules is associated with the physiological condition of interest. In this example, Module 78 is associated with the physiological condition of interest. As illustrated in FIG. 10B, those compounds that correctly activate Module 78 and thus are associated with the physiological condition of interest of Module 78 (fatty acid-related cellular process important for cellular metabolism) are identified (e.g., by the respective calculated activation score for the first cellular constituent module satisfying a first threshold criterion).

Figure 10D:
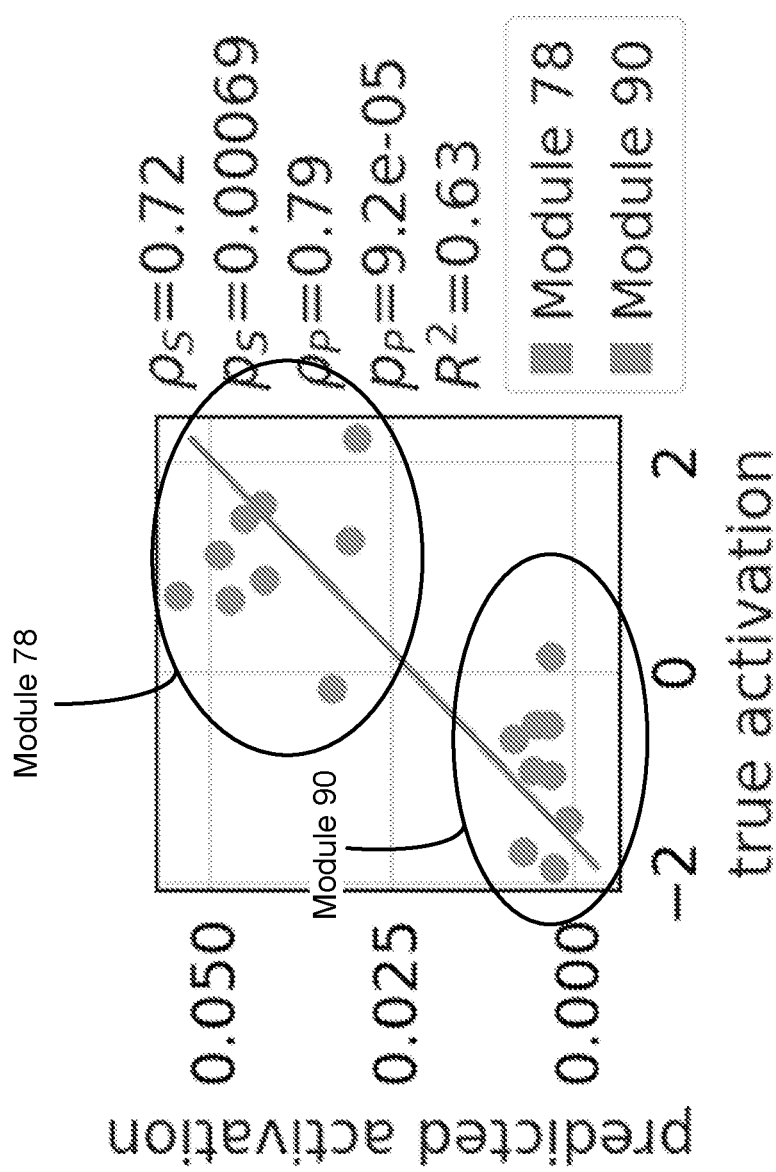

As a second validation of the claimed approach, the respective trained models for Modules 78 and 90 were then applied to an scRNA-seq characterization of certain small molecule "Synthetic Hits" exposed to pre-adipocytes, another test set that had not been introduced to model 601 of FIG. 6 during training. FIG. 10D illustrates a high correlation and faithful prediction of activation indicated by the trained model 601 for Module 78 by the Synthetic Hits, compared to little or no activation by indicated by the trained model 601 for Module 90 by the Synthetic Hits.

Figure 10E:
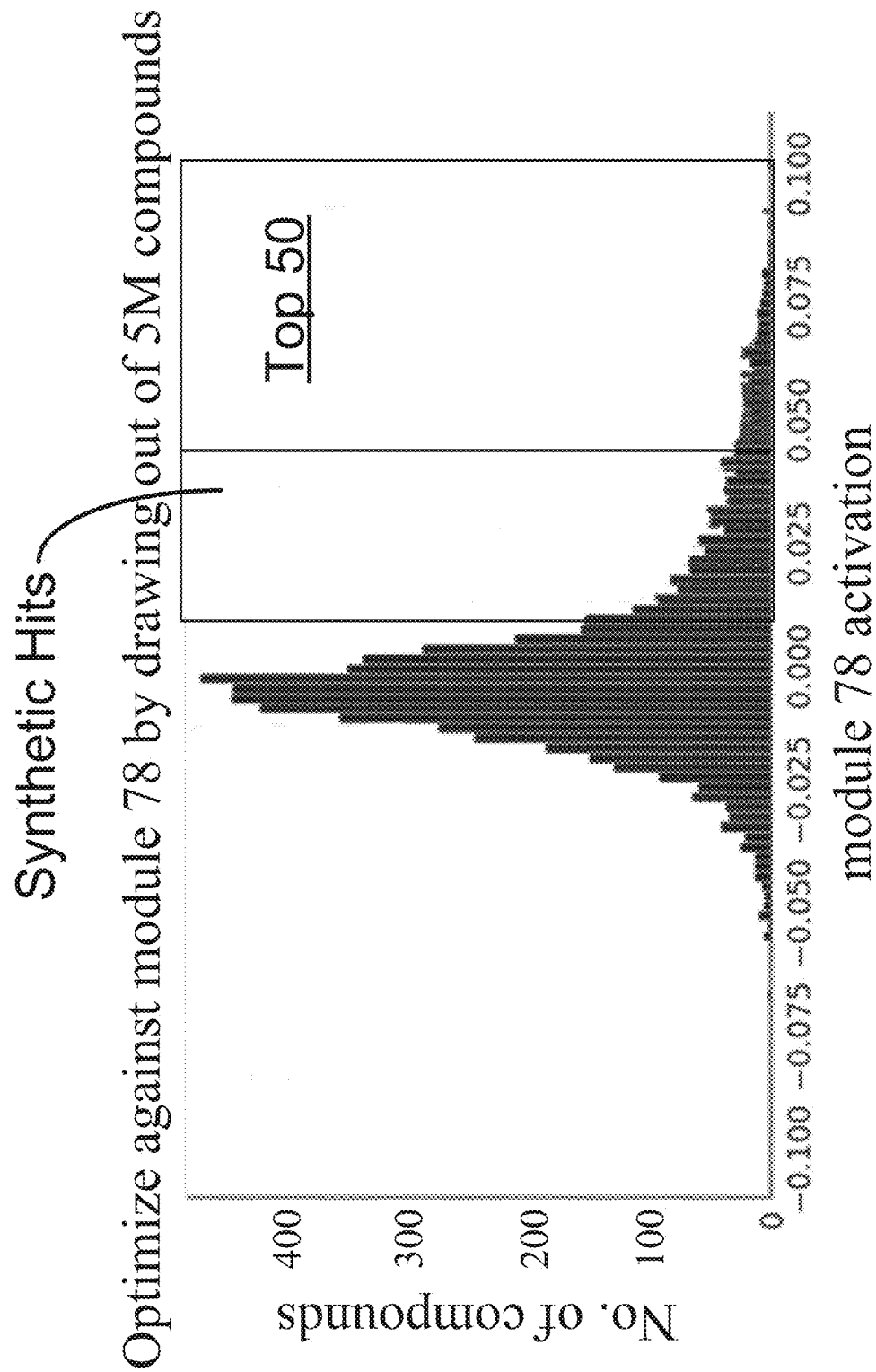

Third, the trained model 601 for Module 78 was used to predict cellular constituent activation scores for cellular constituent module 78 (Module 78) for a random subset of 200,000 compounds sampled from five million compounds in a public database. From this, the top 50 compounds predicted to highly activate cellular constituent module 78 were selected and compared to a set of compounds in a database including compounds from the LINCS L1000 dataset and Synthetic Hit analogs derived from the chemical structure of a known compound, referred to herein as the Known Piperidine-Containing Compound ("KPCC"). The distribution of this comparison is illustrated in FIG. 10E. At the tail end of the distribution, the predictions obtained for the trained model 601 for cellular constituent module 78 identified a compound that significantly exceeded all compounds in LINCS and the Synthetic Hits. This approach highlights a method for optimizing chemical structure against specific desired cellular processes.

Fourth, the chemical structures identified in the top 50 predictions were visually inspected and found to contain evident chemical structures that represent a known adipose tissue-targeting pharmacophore) and thus rightfully activate the cellular constituent module associated with Module 78.

This first example also tracks claim 58 as originally filed. The difference between claim 1 and claim 58 is one of perturbation signatures versus cellular constituent modules. A perturbation signature is obtained by comparing the expression of cells that have been subjected to a perturbation versus cells that have not. Thus, the small molecule perturbagen known to induce metabolically active processes in preadipocytes can be used. A preadipocyte cell line is exposed to the perturbagen for 24 hours and scRNA-seq readouts can be obtained for a perturbed and a control condition. From this, a perturbation signature can be obtained. Alternatively, a separate perturbation signature can be obtained by comparing cell expression of cells that have been exposed to any one of the chemical covariates used for the second dataset. In fact, a separate perturbation signature can be obtained in this manner for each of the chemical covariates used for the second dataset. Each such perturbation signature has the form of a row in the latent representation 404 with the exception being that each such weight is now on a continuous scale, not a binary scale. For instance, in some embodiments each weight is a value on a continuous scale between 0 and 1 (or some other range "A" to "B", where A and B are two different numbers, such as $-100$ and $100$). From there, the process of training is identical to that discussed above with regard to use of the latent representation 404, count matrix 502, activation data structure, and training of component models 601, where each such model now represents a different perturbation signature in a set of perturbation signatures.

Example 2. Predicting Chemical Structures for Activating a Fetal Erythropoiesis Program and Blocking T-Cell Exhaustion In two additional examples, two models on two scRNA-seq datasets related to fetal erythropoiesis and to T cell exhaustion were trained.

For fetal erythropoiesis, CD34 hematopoietic stem cells were treated with the tool compound CLT-AAA-12, for which it has previously been established that endpoint markers of fetal erythropoiesis are induced, in particular, the number of F cells in the assay as readout with flow cytometry.

For T cell exhaustion, naïve T cells were treated with an exhaustion inducing medium.

Both cell systems are characterized with scRNA-seq. Subsequently, a drug reflector model (see, U.S. patent application Ser. No. 16/511,691 entitled "Methods of Analyzing Cells," filed Jul. 15, 2019, which is hereby incorporated by reference), was applied to the scRNA-seq datasets, by inputting cell state transitions defined by the perturbed versus control cells in their respective samples. The drug reflector assigns a cell state activation score for each of the 8000 compounds in the Drug Reflector latent representation. This gives rise to two vectors with cell state activation scores for both transitions (fetal hemoglobin and T cell exhaustion). These two vectors serve as the training data for the model 601.

This model was used to predict compounds that activate fetal erythropoiesis in hematopoietic stem cells and T-cell exhaustion. Fetal erythropoiesis in hematopoietic stem cells are a cellular process that, in recent years, have led to a breakthrough CRISPR therapy for sickle cell disease, while T-cell exhaustion is a key mechanism preventing broader success of checkpoint inhibitor therapies for cancer.

Figure 11:
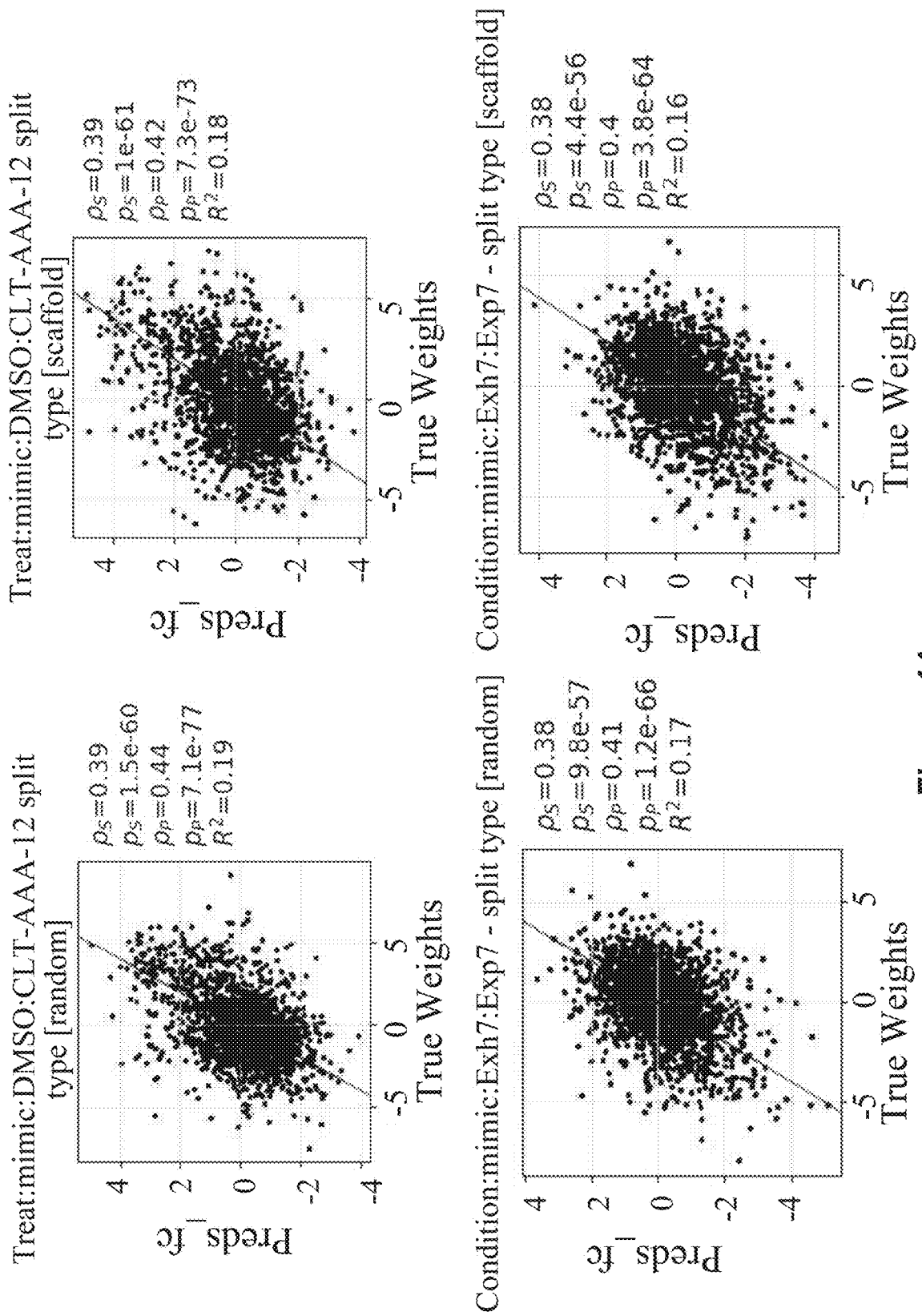
FIG. 11 illustrates validation of an example method for predicting chemical structures for the activation of cellular behaviors relating to fetal erythropoiesis and T-cell exhaustion, in accordance with an embodiment of the present disclosure.
Figure 12:
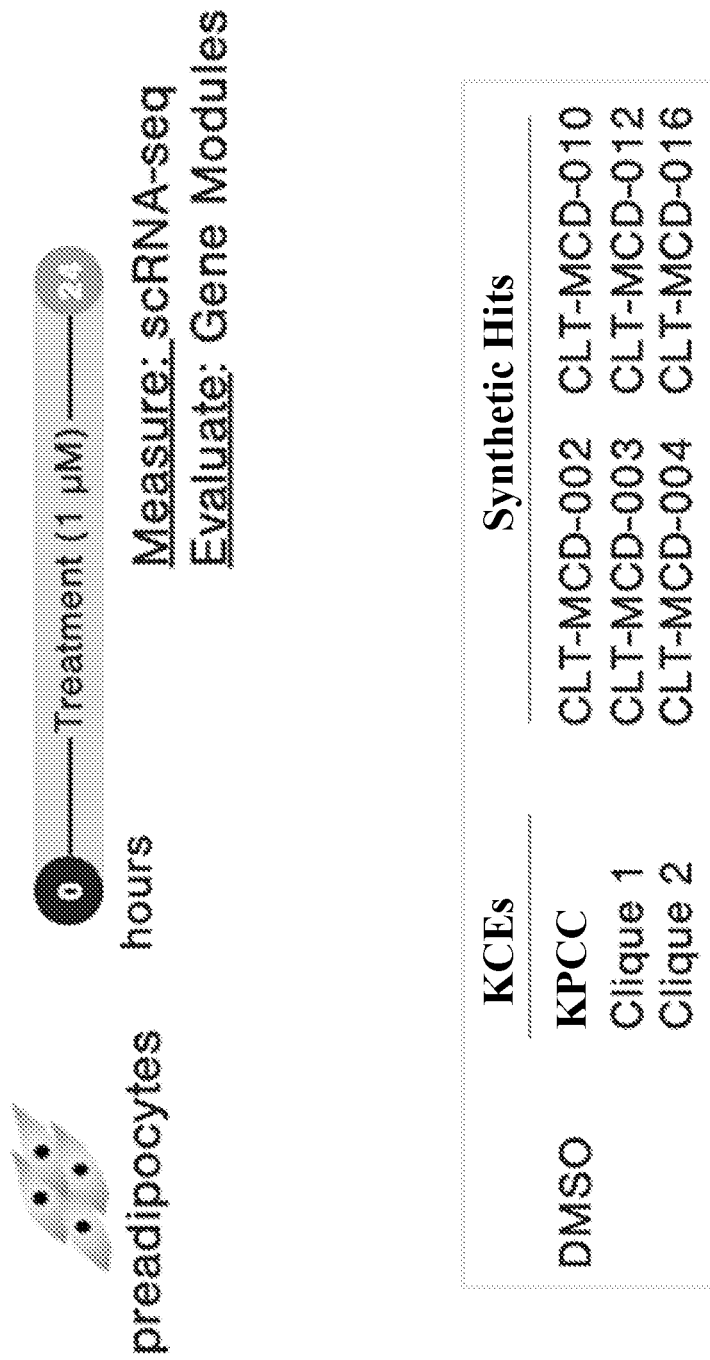
FIG. 12 illustrates a schematic of an example method for evaluating the impact of a Known Piperidine-Containing Compound ("KPCC") and six newly synthesized hits "Synthetic Hits") on human preadipocytes gene module activation using single cell RNA sequencing (scRNA-seq), in accordance with an embodiment of the present disclosure.

Predictions were performed using subsets of 2,000 compounds sampled from the 5 million compounds in a public database, where subsets were split randomly or on scaffolds. The top panel of FIG. 11 shows the performance of the model of this example on a test set of 2,000 compounds, split randomly and on scaffolds, showing significant $R^2$ and correlation coefficients $p_s$ of sampled compounds with the perturbation signature of a hit compound CLT-AAA-12 relating to fetal erythropoiesis in hematopoietic stem cells. The bottom panel of FIG. 11 shows performance of a test set of 2,000 compounds, split randomly and on scaffolds, showing significant $R^2$ and correlation coefficients $p_s$ of sampled compounds with a cell transition signature relating to T-cell exhaustion. Thus, FIG. 11 demonstrates that the model 601 is able to predict new scaffolds that induce the same cellular behavior effects as perturbation signatures and/or cell transition signatures of interest.

Example 3. Feature Attribution Based on Disease-Critical Cell Behaviors: Predicting Pharmacophores for the Design of New Molecules As described in Example 1, the chemical structures predicted in accordance with the systems and methods disclosed herein can be used to identify molecular features, such as pharmacophores, that are potentially related to a physiological condition of interest (e.g., adipose tissue-targeting). As in Example 1, these pharmacophores can be validated by known chemical structures, or can present novel structures for further validation. For instance, an example use case of an algorithm based on pharmacophores includes leveraging a database of pharmacophores with functional meanings previously described in literature, including the Base of Bioisosterically Exchangeable Replacements (BoBER) database. Another example of a use case includes applying expert knowledge, such as by a medicinal chemist, to obtain intuitions regarding the role of an identified pharmacophore in the complex response of a system to a perturbation.

A model for predicting pharmacophores for the design of new molecules was performed, where the model included featurization of small molecules from an intervention library selected based on scores using Teversky similarity to achieve a representation denoting whether the pharmacophore was contained in the chemical structure. This representation (chemical fingerprint) was inputted into the model 601 for Module 78 of Example 1. Using the fat-targeting pharmacophore identified in Example 1, the model for Module 78 of Example 1 was used to determine associations of the fat-targeting pharmacophore of a known piperidine-containing compound ("KPCC") and in isolation with an observed transcriptional activation of a fatty acid module with activation scores ranging from 0.04064 to 0.04633.

Example 4. Generation of Synthetic Hit Compounds Based on Latent Cell Behaviors

As a test case, six of the newly synthesized small molecule hits, referred to herein as "Six Synthetic Hits", were designed based on in vitro and in vivo validated adipocyte beigeing compounds and latent space representations thereof. Each of the Six Synthetic Hits elicited the desired cell behavior change on human preadipocytes. First, pharmacophores of the KPCC cluster were identified. Molecules were then designed by their enrichment of pharmacophores in this cluster, along with the incorporation of novel bioisosteres, leading to the final design of the Six Synthetic Hits. The goal for these Six structurally diverse Synthetic Hits was to induce the same cell behavior effect as known chemical entities (KCEs) including KPCC. As illustrated by the schematic in FIG. 13, cell behavior effects were determined by treating human preadipocytes with 1 μM KPCC and the Six Synthetic Hits for 24 hours, measuring gene expression using scRNA-seq, and evaluating cell responses as expressed by changes in the fat metabolism gene module described in Example 1 above (module 78). For example, genes in the fat metabolism module included FABP3, FDPS, and LPIN1, among others.

Figure 13:
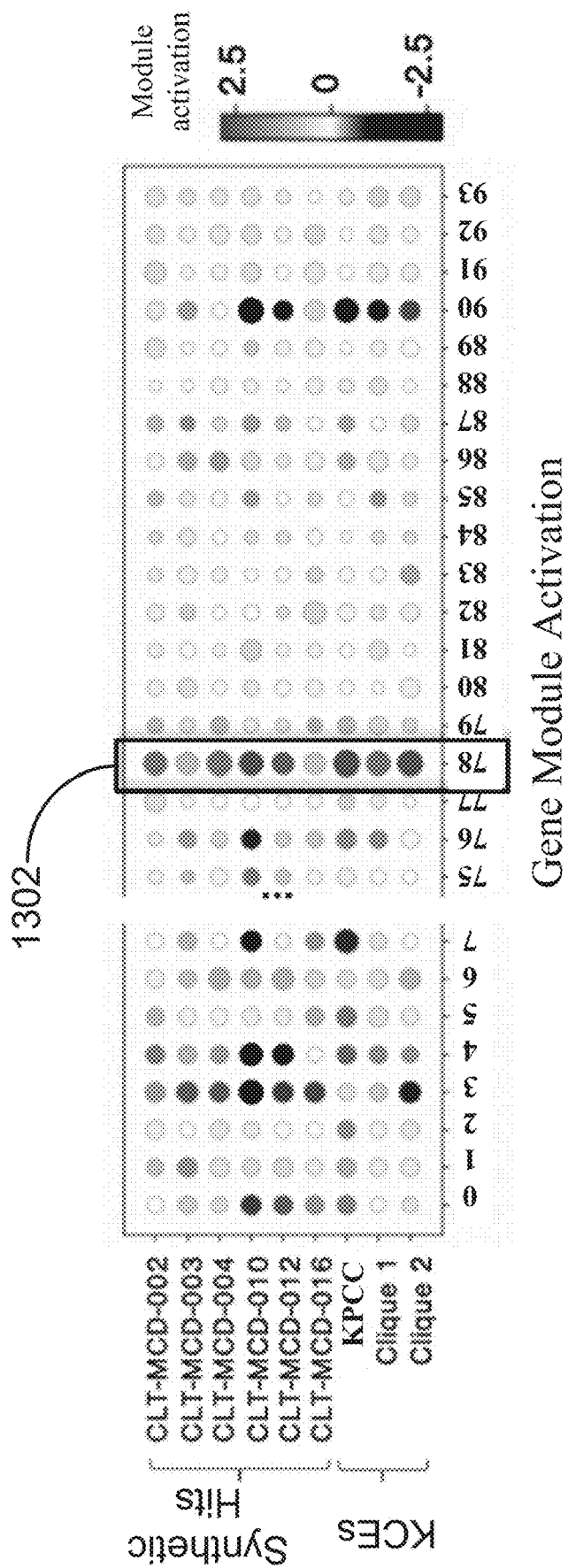
FIG. 13 illustrates the effect of KPCC and the Six Synthetic Hits on activation of a desired transcriptional change, in accordance with an embodiment of the present disclosure.

Evaluation of the impact of these compounds on preadipocytes revealed that each Synthetic Hit activated the same fat metabolism gene module as KPCC (FIG. 13; module 78 highlighted in box 1302). That is, the highlighted box 1302 shows the activation scores outputted by the model for Module 78 of Example 1 upon input of the fingerprints of the compounds into the model listed on the Y-axis of the chart in FIG. 13. These results provide high confidence in the ability to generate Synthetic Hits based on the model platform that predictably target the desired cell behaviors. In particular, the models 601 of the present disclosure (e.g., the model 601 for Module 78 of Example 1) can be used to predict Synthetic Hits that target gene modules associated with physiological conditions without the need for high-throughput screening, molecular target-based identification or optimization, or the synthesis of hundreds or thousands of new compounds for validation.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIGS. 1-3, and 7-9. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of associating a test chemical compound with a physiological condition of interest, the method comprising:
at a computer system, comprising one or more processors and memory:
(A) accessing, in electronic form, a set of cellular constituent modules, a latent representation, and a count data structure, wherein
each respective cellular constituent module in the set of cellular constituent modules includes a respective independent subset of a plurality of cellular constituents,
a corresponding plurality of cell-based assay abundance values for each respective independent subset of the plurality of cellular constituents separately correlate across a plurality of different states associated with the physiological condition,
a first cellular constituent module in the set of cellular constituent modules is associated with the physiological condition of interest and includes a first subset of cellular constituents that represent the physiological condition,
the latent representation comprises a plurality of weights, each respective weight $w_{x\text{-}y}$ in the plurality of weights corresponding to both (i) a corresponding cellular constituent module x in the set of cellular constituent modules and (ii) a corresponding cellular constituent y in the plurality of cellular constituents, wherein each respective weight $w_{x\text{-}y}$ in the plurality of weights is formed from single cell expression data for the set of cellular constituents from a first plurality of at least 500 cells that collectively represent the plurality of different states associated with the physiological condition, and
the count data structure is formed from single cell abundance data for the plurality of cellular constituents from a second plurality of at least 500 cells, wherein each cell in the second plurality of cells is exposed to a training compound n in the plurality of training compounds, and wherein the count data structure comprises a count $cnt_{c\text{-}y}$ for each combination of (i) a cell c in the second plurality of at least 500 cells and (ii) a cellular constituent y in the plurality of cellular constituents;
(B) determining, for each respective training compound n in the plurality of training compounds, for each respective cellular constituent module x in the set of cellular constituent modules, a corresponding activation score $act_{n\text{-}x}$ wherein, $$act_{n\text{-}x} = \Sigma_{y=1}^{Q} w_{x\text{-}y} * cnt_{c\text{-}y}$$

wherein,
c is a cell in the plurality of cells that has been exposed to the respective training compound n, and
Q is a total number of cellular constituents in the plurality of cellular constituents;
(C) obtaining a model comprising 1000 or more parameters, wherein for each respective training compound in the plurality of training compounds, upon input of a fingerprint of a chemical structure of the respective training compound n into the model, the 1000 or more parameters are applied against the fingerprint of the chemical structure to produce a predicted activation score that has concordance with the corresponding activation score $act_{n\text{-}x}$ of the respective training compound for the first cellular constituent module;
(D) obtaining, in electronic form, a fingerprint of a chemical structure of the test chemical compound;
(E) responsive to inputting the fingerprint of the chemical structure of the test chemical compound into the model, retrieving, as output from the model, a calculated activation score for the test chemical compound for the first cellular constituent module; and
(F) associating the test chemical compound with the physiological condition of interest when the calculated activation score for the test chemical compound for the first cellular constituent module satisfies a first threshold criterion.

2. The method of claim 1, wherein the corresponding plurality of cell-based assay abundance values are of cells of an organ, of a tissue, of a plurality of stem cells, of a plurality of primary human cells, of umbilical cord blood, in peripheral blood, in bone marrow, in a solid tissue, or of a plurality of differentiated cells.

3. The method of claim 1, wherein the corresponding plurality of cell-based assay abundance values is single-cell ribonucleic acid (RNA) sequencing (scRNA-seq) data of a plurality of cells.

4. The method claim 3, wherein the plurality of different states associated with the physiological condition is derived by exposing different aliquots of cells to one or more reference compounds known to affect the physiological condition in addition to a control state in which an aliquot of cells is not free of exposure to a compound known to affect the physiological condition.

5. The method of claim 1, wherein the set of cellular constituent modules consists of the first cellular constituent module.

6. The method of claim 1, the method further comprising calculating the fingerprint of the chemical structure from a simplified molecular-input line-entry system (SMILES) string representation of the test chemical compound.

7. The method of claim 1, wherein the set of cellular constituent modules comprises a plurality of cellular constituent modules and the model is an ensemble model comprising a plurality of component models, and wherein each respective component model in the plurality of component models provides an activation score for a different cellular constituent module in the set of cellular constituent modules responsive to inputting the fingerprint of the chemical structure into the respective component model.

8. The method of claim 7, wherein each component model in the plurality of component models is a corresponding neural network.

9. The method of claim 8, wherein
the corresponding neural network is a combination of a corresponding fully connected neural network and a corresponding message passing neural network,
a first output of the corresponding fully connected neural network and a second output of the corresponding message passing neural network is combined, responsive to inputting the fingerprint of the chemical structure into the corresponding fully connected neural network and the corresponding message passing neural network, to determine the activation score for the test chemical compound for the different cellular constituent module in the set of cellular constituent modules.

10. The method of claim 7, wherein a component model in the plurality of component models is a logistic regression model, a neural network model, a support vector machine model, a Naive Bayes model, a nearest neighbor model, a boosted trees model, a random forest model, a decision tree model, a multinomial logistic regression model, a linear model, or a linear regression model.

11. The method of claim 1, wherein
the set of cellular constituent modules is a plurality of cellular constituent modules,
a first subset of the plurality of cellular constituent modules, including the first cellular constituent module, is associated with the physiological condition of interest,
a second subset of the plurality of cellular constituent modules is not associated with the physiological condition of interest, and
the test chemical compound is identified with the physiological condition of interest when the respective calculated activation score for the first cellular constituent module satisfies the first threshold criterion and the respective calculated activation score for a cellular constituent module in the second subset of the plurality of cellular constituent modules satisfies a second threshold criterion, other than the first threshold criterion.

12. The method of claim 1, the method further comprising identifying the first cellular constituent module by a process comprising:
obtaining one or more first datasets in electronic form, the one or more first datasets comprising or collectively comprising:
for each respective cell in the first plurality of cells:
for each respective cellular constituent in the plurality of cellular constituents, wherein the plurality of cellular constituents comprises 10 or more cellular constituents:
a corresponding abundance of the respective cellular constituent in the respective cell,
thereby accessing or forming a plurality of vectors, each respective vector in the plurality of vectors (i) corresponding to a respective cellular constituent in the plurality of constituents and (ii) comprising a corresponding plurality of elements, each respective element in the corresponding plurality of elements having a corresponding count representing the corresponding abundance of the respective cellular constituent in the respective cell in the first plurality of cells;
using the plurality of vectors to identify each candidate cellular constituent module in a plurality of candidate cellular constituent modules, each candidate cellular constituent module in the plurality of candidate cellular constituent modules including a subset of the plurality of cellular constituents, wherein the plurality of cellular constituent modules are arranged in the latent representation, and wherein the plurality of cellular constituent modules comprises more than ten cellular constituent modules;
obtaining one or more second datasets in electronic form, the one or more second datasets comprising or collectively comprising:
for each respective cell in the second plurality of cells, wherein the second plurality of cells collectively represents a plurality of covariates informative of the physiological condition of interest:
for each respective cellular constituent in the plurality of cellular constituents:
a corresponding abundance of the respective cellular constituent in the respective cell,
thereby obtaining the count matrix dimensioned by (i) the second plurality of cells and (ii) the plurality of cellular constituents or a representation thereof;

forming an activation data structure by combining the count matrix and the latent representation using the plurality of cellular constituents or the representation thereof as a common dimension, wherein the activation data structure comprises, for each cellular constituent module in the plurality of cellular constituent modules:
for each cell in the second plurality of cells, a respective activation weight; and
training a candidate cellular constituent model using, for each respective covariate in the plurality of covariates, a difference between (i) a calculated activation against each cellular constituent module represented by the candidate cellular constituent model upon input of a fingerprint of the covariate into the candidate cellular constituent model and (ii) actual activation against each cellular constituent module represented by the candidate cellular constituent model, wherein the training adjusts a plurality of covariate parameters associated with the candidate cellular constituent model responsive to the difference.

13. The method of claim 12, wherein the plurality of covariate parameters comprises:
for each respective cellular constituent module in the plurality of cellular constituent modules:
for each respective covariate:
a corresponding parameter indicating whether the respective covariate correlates, across the second plurality of cells, with the respective cellular constituent module; and the method further comprises:
identifying, using the plurality of covariate parameters upon training the candidate cellular constituent model, the first cellular constituent module in the plurality of candidate cellular constituent modules.

14. The method of claim 12, wherein a cell state in the plurality of different cell states is an exposure of a cell in the first plurality of cells to a training compound in the plurality of training compounds under an exposure condition.

15. The method of claim 14, wherein the exposure condition is a duration of exposure, a concentration of the training compound, or a combination of a duration of exposure and a concentration of the training compound.

16. The method of claim 12, wherein
each cellular constituent in the plurality of cellular constituents is a particular gene, a particular mRNA associated with a gene, a carbohydrate, a lipid, an epigenetic feature, a metabolite, a protein, or a combination thereof, and
the corresponding abundance of the respective cellular constituent in the respective cell in the first or second plurality of cells is determined by a colorimetric measurement, a fluorescence measurement, a luminescence measurement, or a resonance energy transfer (FRET) measurement.

17. The method of claim 12, wherein using the plurality of vectors to identify each candidate cellular constituent module in the plurality of candidate cellular constituent modules comprises application of a correlation model to the plurality of vectors using each corresponding plurality of elements of each vector in the plurality of vectors.

18. The method of claim 17, wherein the correlation model includes a graph clustering.

19. The method of claim 18, wherein the graph clustering is Leiden clustering on a Pearson-correlation-based distance metric or a Louvain clustering.

20. The method of claim 12, wherein
the model comprises $1 \times 10^6$ or more parameters,
the respective independent subset of a plurality of cellular constituents comprises at least 5 cellular constituents,
the set of cellular constituent modules comprises five or more cellular constituent modules, and
the plurality of cellular constituents comprises 1000 or more cellular constituents.

21. The method of claim 1, wherein each cellular constituent in the plurality of cellular constituents is a particular gene, a particular mRNA associated with a gene, a carbohydrate, a lipid, an epigenetic feature, a metabolite, a protein, or a combination thereof.

22. The method of claim 1, wherein the test chemical compound is an organic compound having a molecular weight of less than 2000 Daltons.

23. The method claim 1, wherein the model comprises a logistic regression model, a neural network model, a support vector machine model, a Naive Bayes model, a nearest neighbor model, a boosted trees model, a random forest model, a decision tree model, a multinomial logistic regression model, a linear model, or a linear regression model.

24. The method of claim 1, the method further comprising generating the fingerprint from a chemical structure of the test chemical compound using Daylight, BCI, ECFP4, EcFC, MDL, APFP, TTFP, UNITY 2D fingerprint, RNNS2S, or GraphConv.

25. The method of claim 1, wherein the independent subset of the plurality of cellular constituents in the respective cellular constituent module comprises five or more cellular constituents.

26. The method of claim 1, wherein the independent subset of the plurality of cellular constituents in the respective cellular constituent module consists of between two and 20 cellular constituents in a molecular pathway associated with the physiological condition of interest.

27. The method of claim 1, wherein the model comprises $1 \times 10^6$ or more parameters.

28. The method of claim 1, wherein the 1000 or more parameters comprises a different set of weights for each cellular constituent module in the set of cellular constituent models.

29. The method of claim 1, wherein the fingerprint is a graph representation of the chemical structure, wherein the graph representation comprises a plurality of nodes and a plurality of edges, wherein each respective node in the plurality of nodes represents an atom in the chemical structure and each respective edge in the plurality of edges represents a bond in the chemical structure.

30. The method of claim 1, wherein the model comprises 10,000 or more parameters.

* * * * *